(12) United States Patent
Sakon et al.

(10) Patent No.: US 11,624,060 B2
(45) Date of Patent: Apr. 11, 2023

(54) COLLAGEN-BINDING AGENT COMPOSITIONS AND METHODS OF USING THE SAME

(71) Applicants: THE BOARD OF TRUSTEES OF THE UNIVERSITY OF ARKANSAS, Little Rock, AR (US); THE KITASATO INSTITUTE, Tokyo (JP)

(72) Inventors: Joshua Sakon, Fayetteville, AR (US); Jeffrey Roeser, Texarkana, TX (US); Ryan Bauer, Fayetteville, AR (US); Katarzyna Janowska, Chapel Hill, NC (US); Keisuke Tanaka, Chiba (JP); Osamu Matsushita, Okayama (JP); Kentaro Uchida, Tokyo (JP)

(73) Assignees: The Board of Trustees of the University of Arkansas, Little Rock, AR (US); The Kitasato Institute, Tokyo (JP)

( * ) Notice: Subject to any disclaimer, the term of this patent is extended or adjusted under 35 U.S.C. 154(b) by 88 days.

(21) Appl. No.: 16/485,290

(22) PCT Filed: Feb. 9, 2018

(86) PCT No.: PCT/US2018/017665
§ 371 (c)(1),
(2) Date: Aug. 12, 2019

(87) PCT Pub. No.: WO2018/148573
PCT Pub. Date: Aug. 16, 2018

(65) Prior Publication Data
US 2019/0376053 A1 Dec. 12, 2019

Related U.S. Application Data

(60) Provisional application No. 62/457,410, filed on Feb. 10, 2017.

(51) Int. Cl.
| | | |
|---|---|---|
| *A61K 38/18* | (2006.01) | |
| *A61K 38/16* | (2006.01) | |
| *C07K 14/50* | (2006.01) | |
| *A61P 19/08* | (2006.01) | |
| *C12N 9/52* | (2006.01) | |
| *A61P 19/00* | (2006.01) | |
| *A61K 8/64* | (2006.01) | |
| *A61K 8/66* | (2006.01) | |
| *A61Q 7/00* | (2006.01) | |
| *C07K 14/635* | (2006.01) | |

(52) U.S. Cl.
CPC ............ *C12N 9/52* (2013.01); *A61K 8/64* (2013.01); *A61K 8/66* (2013.01); *A61K 38/16* (2013.01); *A61K 38/1825* (2013.01); *A61P 19/00* (2018.01); *A61P 19/08* (2018.01); *A61Q 7/00* (2013.01); *C07K 14/50* (2013.01); *C07K 14/503* (2013.01); *C07K 14/635* (2013.01); *C12Y 304/24003* (2013.01); *C07K 2319/00* (2013.01)

(58) Field of Classification Search
CPC ............ A61K 38/1825; A61K 47/6415; C07K 14/475; C07K 14/503; C07K 2319/00
See application file for complete search history.

(56) References Cited

U.S. PATENT DOCUMENTS

| | | |
|---|---|---|
| 5,914,126 A | 6/1999 | Li et al. |
| 6,362,163 B1 | 3/2002 | Gardella et al. |
| 7,396,664 B2 | 7/2008 | Daly |
| 8,030,448 B2 | 10/2011 | Koide et al. |
| 8,450,273 B2 | 5/2013 | Sakon et al. |
| 8,617,543 B2 | 12/2013 | Huang et al. |
| 9,062,300 B2 | 6/2015 | Gensure et al. |
| 9,248,164 B2 | 2/2016 | Uchida et al. |
| 9,354,240 B2 | 5/2016 | Yamagata et al. |
| 9,526,765 B2 | 12/2016 | Ponnapakkam et al. |
| 9,528,099 B2 | 12/2016 | Gensure et al. |
| 9,579,273 B2 | 2/2017 | Ponnapakkam et al. |
| 9,757,435 B2 | 9/2017 | Herber |
| 10,046,040 B2 | 8/2018 | Galen |
| 10,047,404 B2 | 8/2018 | Bergeron |
| 10,111,983 B2 | 10/2018 | Shimp |
| 10,202,434 B2 | 2/2019 | Gensure et al. |
| 10,213,488 B2 | 2/2019 | Ponnapakkam et al. |
| 10,358,471 B2 | 7/2019 | Gensure et al. |
| 10,507,230 B2 | 12/2019 | Yamamoto |
| 10,519,213 B2 | 12/2019 | Gensure |

(Continued)

FOREIGN PATENT DOCUMENTS

| | | |
|---|---|---|
| EP | 207751 | 1/1987 |
| JP | 200258485 | 2/2002 |

(Continued)

OTHER PUBLICATIONS

Nishida et al., Nat. Struct. Biol., 2003, vol. 10(1):53-58.*

(Continued)

*Primary Examiner* — Xiaozhen Xie
(74) *Attorney, Agent, or Firm* — Quarles & Brady LLP

(57) ABSTRACT

The invention generally relates to collagen-binding agent compositions and methods of using the same. More specifically, the invention relates in part to new collagen-binding agent compositions and methods that may be used to treat damaged collagen within tissues or used to specifically target therapeutics to tissues containing undamaged or damaged collagen.

9 Claims, 14 Drawing Sheets
(1 of 14 Drawing Sheet(s) Filed in Color)
Specification includes a Sequence Listing.

(56) References Cited

U.S. PATENT DOCUMENTS

| | | | |
|---|---|---|---|
| 10,519,236 | B2 | 12/2019 | Koide |
| 2002/0102709 | A1 | 8/2002 | Ishikawa et al. |
| 2002/0164719 | A1 | 11/2002 | Hall et al. |
| 2003/0187232 | A1 | 10/2003 | Hubbell et al. |
| 2004/0053368 | A1 | 3/2004 | Ishikawa et al. |
| 2004/0220094 | A1 | 11/2004 | Skinner |
| 2005/0119183 | A1 | 6/2005 | Wells |
| 2005/0124537 | A1 | 6/2005 | Kostenuik et al. |
| 2005/0180986 | A1 | 8/2005 | Rich et al. |
| 2006/0014687 | A1 | 1/2006 | Crine et al. |
| 2006/0257376 | A1 | 11/2006 | Scadden et al. |
| 2008/0108562 | A1 | 5/2008 | Riviere et al. |
| 2009/0305352 | A1 | 12/2009 | Dai et al. |
| 2010/0129341 | A1 | 5/2010 | Sakon et al. |
| 2010/0159564 | A1 | 6/2010 | Dwulet et al. |
| 2013/0287759 | A1 | 10/2013 | Muñoz Montano |
| 2013/0337017 | A1 | 12/2013 | Gensure et al. |
| 2014/0335146 | A1 | 11/2014 | Uchida et al. |
| 2014/0377215 | A1 | 12/2014 | Ponnapakkam et al. |
| 2015/0038423 | A1* | 2/2015 | Ponnapakkam ....... A61K 47/56 514/17.2 |
| 2015/0284701 | A1 | 10/2015 | Gensure et al. |
| 2016/0339078 | A1 | 11/2016 | Hamill et al. |
| 2017/0101457 | A1 | 4/2017 | Gensure et al. |
| 2017/0106093 | A1 | 4/2017 | Ponnapakkam et al. |
| 2017/0204390 | A1 | 7/2017 | Ponnapakkam et al. |
| 2018/0055918 | A1 | 3/2018 | Herber |
| 2018/0140742 | A1 | 5/2018 | Uchida et al. |
| 2019/0249163 | A1 | 8/2019 | Ponnapakkam et al. |
| 2020/0023041 | A1 | 1/2020 | Holten-Andersen et al. |

FOREIGN PATENT DOCUMENTS

| | | |
|---|---|---|
| JP | 2003284553 A * | 10/2003 |
| JP | 2004500838 | 1/2004 |
| JP | 2010523671 | 7/2010 |
| WO | 2000006195 | 2/2000 |
| WO | 2000049159 | 8/2000 |
| WO | 2003052091 | 6/2003 |
| WO | 2004071543 | 8/2004 |
| WO | 2006072623 | 7/2006 |
| WO | 2008067199 | 5/2008 |
| WO | 2008124166 | 10/2008 |
| WO | 2009014854 | 1/2009 |
| WO | 2010087397 | 8/2010 |
| WO | 2011142425 | 11/2011 |
| WO | 2012124338 | 9/2012 |
| WO | 2012157339 | 11/2012 |
| WO | 2013090770 | 6/2013 |
| WO | 2013120030 | 8/2013 |
| WO | 2013120060 | 8/2013 |
| WO | 2016060252 | 4/2016 |
| WO | 2016142146 | 9/2016 |
| WO | 2019113123 | 6/2019 |
| WO | 2019173829 | 12/2019 |

OTHER PUBLICATIONS

Uchida et al., J. Biomed. Mater. Res. Part A, 2014, vol. 102A:1737-1743.*

Abdelhadi, M. et al., "Bone mineral recovery after parathyroidectomy in patients with primary and renal hyperparathyroidism," J Clin Endocrinol Metab. (1998) 83(11):3845-51.

Abe, Y. et al., "Enhancement of graft bone healing by intermittent administration of human parathyroid hormone (1-34) in a rat spinal arthrodesis model," Bone (2007) 41(5):775-785.

Abshirini, H.et al., "Pathologic fractures: a neglected clinical feature of parathyroid adenoma," Case (2010) p. 357029. Epub Nov. 29, 2010.

Akimoto, M. et al., "Effects of CB-VEGF-A injection in rat flap models for improved survival," (2013) Plast. Reconstr. Surg. 131(4):717-725.

Aleksyniene, R. et al., "Parathyroid hormone-possible future drug for orthopedic surgery," Medicina (Kaunas) (2004) 40(9):842-9.

Andrade, M.C., et al., "Bone mineral density and bone histomorphometry in children on long-term dialysis," Pediatr Nephrol. (2007) 22(10):1767-72. Epub Aug. 7, 2007.

Andrades, J.A. et al., "A recombinant human TGF-beta1 fusion protein with collagen-binding domain promotes migration, growth, and differentiation of bone marrow mesenchymal cells," Exp. Cell Res. (1999) 250(2):485-498.

Barros, S.P., et al., "Parathyroid hormone protects against periodontitis-associated bone loss," J Dent Res. (2003) 82(10):791-5.

Bauer R, et al: Structures of three polycystic kidney disease-like domains from Clostridium histolyticum collagenases ColG and ColH. Acta Crystallogr D Biol Crystallogr 2015;71:565-577.

Bedi, B., et al., "Inhibition of antigen presentation and T cell costimulation blocks PTH-induced bone loss," Ann N Y Acad Sci. (2010) 1192:215-21.

Belinsky, G.S. et al., "Direct measurement of hormone-induced acidification in intact bone," J Bone Miner Res., (2000) 15(3):550-6.

Bellido, T., et al., "Chronic elevation of parathyroid hormone in mice reduces expression of sclerostin by osteocytes: a novel mechanism for hormonal control of osteoblastogenesis," Endocrinology (2005) 146(11):4577-83. Epub Aug. 4, 2005.

Bergenstock, M.K. et al., "Parathyroid hormone stimulation of noncanonical Wnt signaling in bone," Ann N Y Acad Sci. (2007) 1116:354-9.

Bergwiiz, C. et al., "Rapid desensitization of parathyroid hormone dependent adenylate cyclase in perifused human osteosarcoma cells (SaOS-2)," Biochem Biophys Acta. (1994) 1222(3):447-56.

Bianchi, E.N. et al., "Beta-arrestin2 regulates parathyroid hormone effects on a p38 MAPK and NFkappaB gene expression network in osteoblasts" Bone (2009) 45(4):716-25. Epub Jun. 25, 2009.

Bilezikian, J.P. et al., "Asymptomatic primary hyperparathyroidism: new issues and new questions—bridging the past with the future," J Bone Miner Res. (2002) 17(Suppl 2):N57-67.

Bilezikian, J.P. et al., "Characterization and evaluation of asymptomatic primary hyperparathyroidism," J Bone Miner Res. (1991) 6(Suppl 2):S85-9; discussion S121-4.

Blachowicz, A. et al., "Serum 1-84 and 7-84 parathyroid hormone concentrations and bone in patients with primary hyperparathyroidism," Langenbecks Arch Surg. (2008) 393(5):709-13. Epub Jul. 11, 2008.

Buargub, M.A. et al., "Prevalence and pattern of renal osteodystrophy in chronic hemodialysis patients: a cross sectional study of 103 patients," Saudi J Kidney Dis Transpl. (2006) 17(3):401-7.

Calvi, L.M. et al., "Activated parathyroid hormone/parathyroid hormone-related protein receptor in osteoblastic cells differentially affects cortical and trabecular bone," J. Clin. Invest. (2001)107:277-286.

Calvi, L.M. et al., "Osteoblastic cells regulate the haematopoietic stem cell niche," Nature (2003) 425:841-846.

Canalis, E. et al., "Insulin-like growth factor I mediates selective anabolic effects of parathyroid hormone in bone cultures," J Clin Invest. (1989) 83(1):60-5.

Canalis, E., "Effect of hormones and growth factors on alkaline phosphatase activity and collagen synthesis in cultured rat calvariae," Metabolism (1983) 32(1):14-20.

Carter, P.H. et al., "Selective and Nonselective Inverse Agonists for Constitutively Active Type-1 Parathyroid Hormone Receptors: Evidence for Altered Receptor Conformations," Endocrinology (2001) 142(4):1534-1545.

Chan, H.W. et al., "Prospective study on dialysis patients after total parathyroidectomy without autoimplant," Nephrology (2009) 15(4):441-7.

Chen, B. et al., "Homogeneous osteogenesis and bone regeneration by demineralized bone matrix loading with collagen-targeting bone morphogenetic protein-2," Biomaterials (2007) 28:1027-1035.

Chen, Q. et al., "Effects of an excess and a deficiency of endogenous parathyroid hormone on volumetric bone mineral density and bone geometry determined by peripheral quantitative computed tomography in female subjects," J Clin Endocrinol Metab. (2003) 88(10):4655-8.

(56) References Cited

OTHER PUBLICATIONS

Cherian, P.P. et al., "Role of gap junction, hemichannels, and connexin 43 in mineralizing in response to intermittent and continuous application of parathyroid hormone," Cell Commun Adhes. (2008) 15(1):43-54.

Chevalley, T. et al., "Bone and hormones. Effects of parathyroid hormone on the bone," Presse Med. (1999) 28(10):547-53.

Cohen, A. et al., "Osteoporosis in adult survivors of adolescent cardiac transplantation may be related to hyperparathyroidism, mild renal insufficiency, and increased bone turnover," J Heart Lung Transplant. (2005) 24(6):696-702.

Compston, J.E., "Skeletal actions of intermittent parathyroid hormone: effects on bone remodelling and structure," Bone (2007) 40(6):1447-1452.

Cormier, C., "Parathyroid hormone in osteoporosis," Presse Med. (2006) 35(3 Pt 2):495-501.

Corsi, A. et al., "Osteomalacic and hyperparathyroid changes in fibrous dysplasia of bone: core biopsy studies and clinical correlations," J Bone Miner Res. (2003) 18(7):1235-46.

Cosman, F., "Parathyroid hormone treatment for osteoporosis," Current Opinion in Endocrinology, Diabetes & Obesity (2008) 15:495-501.

Cundy, T. et al., "Hyperparathyroid bone disease in chronic renal failure," Ulster Med J. (1985) 54(Suppl):S34-43.

Datta, N.S. et al., "Distinct roles for mitogen-activated protein kinase phosphatase-1 (MKP-1) and ERK-MAPK in PTH1R signaling during osteoblast proliferation and differentiation," Cell (2010) 22(3):457-66. Epub.

Deal, C., "The use of intermittent human parathyroid hormone as a treatment for osteoporosis," Curr Rheumatol Rep. (2004) 6(1):49-58.

Demiralp, B. et al., "Anabolic actions of parathyroid hormone during bone growth are dependent on c-fos," Endocrinology (2002) 143(10):4038-47.

Dobnig, H. et al., "The effects of programmed administration of human parathyroid hormone fragment (1-34) on bone histomorphometry and serum chemistry in rats," Endocrinology (1997) 138(11):4607-12.

Drake, M.T. et al., "Parathyroid hormone increases the expression of receptors for epidermal growth factor in UMR 106-01 cells," Endocrinology (1994) 134(4):1733-7.

Eckhard, U. et al (2011). "Polycystic kidney disease-like domains of clostridial collagenases and their role in collagen recruitment." Biol Chem 392(11): 1039-1045.

Eckhard, U., et al (2011). "Structure of collagenase G reveals a chew-and-digest mechanism of bacterial collagenolysis." Nat Struct Mol Biol 18(10): 1109-1114.

Endo, K. et al., "1,25-dihydroxyvitamin D3 as well as its analogue OCT lower blood calcium through inhibition of bone resorption in hypercalcemic rats with continuous parathyroid hormone-related peptide infusion," J Bone Miner Res. (2000) 15(1):175-81.

Etoh, M. et al., "Repetition of continuous PTH treatments followed by periodic withdrawals exerts anabolic effects on rat bone," J Bone Miner Metab. (2010) 28(6):641-649.

Extended European Search Report for Application No. 08742686.2 dated Aug. 4, 2010 (8 pages).

Extended European Search Report for Application No. 12857691.5 dated Feb. 8, 2016 (16 pages).

Farhanigan, M.E., et al. Treatment of Alopecia Areata in the United States: A Retrospective Cross-Sectional Study. J Drugs Dermatology. 2015 14(9):1012-4.

Fitzpatrick, L.A. et al., "Acute primary hyperparathyroidism," Am J Med. (1987) 82(2):275-82.

Fleming, A. et al., "High-throughput in vivo screening for bone anabolic compounds with zebrafish," J Biomol Screen. (2005) 10(8):823-31. Epub Oct. 18, 2005.

Fouda, M.A., "Primary hyperparathyroidism: King Khalid University Hospital Experience," Ann Saudi Med. (1999) 19(2):110-5.

Kaye, M. et al., "Elective total parathyroidectomy without autotransplant in end-stage renal disease," Kidney Int. (1989) 35(6):1390-9.

Khan, A. et al., "Primary hyperparathyroidism: pathophysiology and impact on bone," Cmaj. (2000) 163(2):184-7.

Kido, S. et al., "Mechanism of PTH actions on bone," Clin Calcium. (2003) 13(1):14-8.

Kistler, H., "Primary hyperparathyroidism: An analysis of 152 patients with special references to acute life threatening complications (acute hyperparathyroidism)," Schweiz Med Wochenschr. (1976) 106(Suppl 3):1-61.

Kitazawa, R. et al., "Effects of continuous infusion of parathyroid hormone and parathyroid hormone-related peptide on rat bone in vivo: comparative study by histomorphometry," Bone Miner. (1991) 12(3):157-66.

Klempa, I., "Treatment of secondary and tertiary hyperparathyroidism—surgical viewpoints," Chirurg. (1999) 70(10):1089-101.

Koh, A.J. et al., "3',5'-Cyclic adenosine monophosphate activation in osteoblastic cells: effects on parathyroid hormone-1 receptors and osteoblastic differentiation in vitro," Endocrinology (1999) 140(7):3154-62.

Komarova, S.V., "Mathematical model of paracrine interactions between osteoclasts and osteoblasts predicts anabolic action of parathyroid hormone on bone," Endocrinology. (2005) 146(8):3589-95. Epub Apr. 28, 2005.

Kousteni, S. et al., "The cell biology of parathyroid hormone in osteoblasts," Curr Osteoporos. Rep. (2008) 6(2):72-6.

Kroll, M.H., "Parathyroid hormone temporal effects on bone formation and resorption," Bull Math Biol. (2000) 62(1):163-88.

Lemaire, V. et al., "Modeling the interactions between osteoblast and osteoclast activities in bone remodeling," J Theor Biol. (2004) 229(3):293-309.

Li, X. et al., "Determination of dual effects of parathyroid hormone on skeletal gene expression in vivo by microarray and network analysis," J Biol Chem. (2007) 282(45):33086-97. Epub Aug. 9, 2007.

Li, X. et al., "In vivo parathyroid hormone treatments and RNA isolation and analysis," Methods Mol Biol. (2008) 455:79-87.

Liu, J. et al., "Intermittent PTH administration: a novel therapy method for periodontitis-associated alveolar bone loss," Med Hypotheses. (2009) 72(3):294-6. Epub Nov. 30, 2008.

Locklin, R.M. et al., "Mediators of the biphasic responses of bone to intermittent and continuously administered parathyroid hormone," J Cell Biochem. (2003) 89(1):180-90.

Locus BAA06251 (GI 710023), Collagenase precursor from Clostridium histolyticum, Jan. 30, 2003. This amino acid sequence is disclosed in this application as SEQ ID No. 6. The sequence of residues 901-1021 of BAA06251 corresponds to the collagen binding domain included in the fusion protein of SEQ ID No. 1.

Locus EAW68494 (GI 119588900), Parathyroid hormone isoform from *Homo sapiens*, Dec. 18, 2006. Residues 64-147 of EAW68494 correspond to the PTH of SEQ ID No. 7.

Lotinun, S. et al., "Differential effects of intermittent and continuous administration of parathyroid hormone on bone histomorphometry and gene expression," Endocrine. (2002) 17(1):29-36.

Lotinun, S. et al., "Triazolopyrimidine (trapidil), a platelet-derived growth factor antagonist, inhibits parathyroid bone disease in an animal model for chronic hyperparathyroidism," Endocrinology. (2003) 144(5):2000-7.

Lumachi, F. et al., "Lumbar spine bone mineral density changes in patients with primary hyperparathyroidism according to age and gender," Ann N Y Acad Sci. (2007) 1117:362-6. Epub Jul. 26, 2007.

Ma, Y.L. et al., "Catabolic effects of continuous human PTH (1-38) in vivo is associated with sustained stimulation of RANKL and inhibition of osteoprotegerin and gene-associated bone formation," Endocrinology (2001) 142(9):4047-54.

Machado Do Reis, L. et al., "Accentuated osteoclastic response to parathyroid hormone undermines bone mass acquisition in osteonectin-null mice," Bone (2008) 43(2):264-73. Epub Apr. 13, 2008.

Malluche, H.H. et al., "Effects of long-term infusion of physiologic doses of 1-34 PTH on bone" Am J Physiol. (1982) 242(2):F197-201.

Malluche, H.H. et al., "Endogenous calcitonin does not protect against hyperparathyroid bone disease in renal failure," Miner. Electrolyte Metab. (1986) 12(2):113-8.

Malluche, H.H. et al., "Influence of the parathyroid glands on bone metabolism," Eur J Clin Invest. (2006) 36(Suppl 2):23-33.

(56) References Cited

OTHER PUBLICATIONS

Malluche, H.H. et al., "Osteomalacia and hyperparathyroid bone disease in patients with nephrotic syndrome," J Clin Invest. (1979) 63(3):494-500.
Masi, L. et al., "Molecular, biochemical and cellular biology of PTH anabolic action," J Endocrinol Invest. (2005) 28(8 Suppl):37-40.
Mathias, R. et al., "Renal bone disease in pediatric and young adult patients on hemodialysis in a children's hospital," J Am Soc Nephrol. (1993) 3(12):1938-46.
Matsushita, O. et al., "A study of the collagen-binding domain of a 116-kDa Clostridium histolyticum collagenase," J Biological Chem (1998) 273(6):3643-3648.
Matsushita, O. et al., "Gene duplication and multiplicity of C. Histolyticum collagenases," J. Bacteriol. (1999) 181:923-933.
Matsushita, O. et al., "Substrate recognition by the collagen-binding domain of Clostridium histolyticum class I collagenase," J of Biological Chem (2001) 276(12):8761-8770.
McCauley, L.K. et al., "Parathyroid hormone stimulates fra-2 expression in osteoblastic cells in vitro and in vivo," Endocrinology (2001) 142(5):1975-81.
McCauley, L.K. et al., "Proto-oncogene c-fos is transcriptionally regulated by parathyroid hormone (PTH) and PTH-related protein in a cyclic adenosine monophosphate-dependent manner in osteoblastic cells," Endocrinology (1997) 138(12):5427-33.
McCauley, L.K. et al., "PTH/PTHrP receptor is temporally regulated during osteoblast differentiation and is associated with collagen synthesis," J Cell Biochem (1996) 61:638-647.
Minisola, S. et al., "Trabecular bone mineral density in primary hyperparathyroidism: relationship to clinical presentation and biomarkers of skeletal turnover," Bone Miner. (1993) 20(2):113-23.
Minisola, S. et al., "Uneven deficits in vertebral bone density in postmenopausal patients with primary hyperparathyroidism as evaluated by posterior-anterior and lateral dual-energy absorptiometry," Osteoporos Int. (2002) 13(8):618-23.
Mitlak, B.H. et al., "Asymptomatic primary hyperparathyroidism," J Bone Miner Res. (1991) 6(Suppl 2):S103-10; discussion S121-4.
Miyachi, Y. et al., "Long-term safety and efficacy of high-concentration (20 mug/g) tacalcitol ointment in psoriasis vulgaris," Eur J Dermatol (2002) 12(5):463-468.
Morley, P. et al., "Anabolic effects of parathyroid hormone on bone," Trends Endocrinol. Metab. (1997) 8(6):225-31.
Morley, P. et al., "Parathyroid hormone: an anabolic treatment for osteoporosis," Curr Pharm Des. (2001) 7(8):671-87.
Murray, E.J. et al., "E64d, a membrane-permeable cysteine protease inhibitor, attenuates the effects of parathyroid hormone on osteoblasts in vitro," Metabolism (1997) 46(9):1090-4.
Nasu, M. et al., "Stimulatory effects of parathyroid hormone and 1,25-dihydroxyvitamin D3 on insulin-like growth factor-binding protein-5 mRNA expression in osteoblastic UMR-106 cells: the difference between transient and continuous treatments," FEBS Lett. (1997) 409(1):63-6.
Neer, R.M. et al., "Effect of parathyroid hormone (1-34) on fractures and bone mineral density in postmenopausal women with osteoporosis," N. Engl. J. Med. (2001) 344(19):1434-1441.
Nemeth, E.F., "Pharmacological regulation of parathyroid hormone secretion," Curr Pharm. Des. (2002) 8(23):2077-87.
Nilsson, P., "Bone disease in renal failure. Clinical and histomorphometric studies," Scand J Urol Nephrol Suppl. (1984) 84:1-68.
Nishi, N. et al., "A novel drug delivery system with a collagn-binding domain derived from Clostridium histolyticum collagnase" Connective Tissue (1998) 30(1):37-42.
Nishi, N. et al., "Collagen-binding growth factors: Production and characterization of functional fusion proteins having a collagen-binding domain," PNAS (1998) 95(12):7018-7023.
Nomura, R. et al., "Contribution of the Collagen-Binding Proteins of Streptococcus mutans to Bacterial Colonization of Inflamed Dental Pulp" PLoS One (2016) 11(7):e0159613.

O'Brien, C.A. et al., "IL-6 is not required for parathyroid hormone stimulation of RANKL expression, osteoclast formation, and bone loss in mice," Am J Physiol Endocrinol Metab. (2005) 289(5):E784-93. Epub Jun. 14, 2005.
Ohbayashi, N., et al. (2013). "Solution structure of clostridial collagenase h and its calcium-dependent global conformation change." Biophys J 104(7): 1538-1545.
Yoshihara, K. et al., "Cloning and nucleotide sequence analysis of the colH gene from Clostridium histolyticum encoding a collagenase and a gelatinase," J Bacteriol (1994) 176:6489-6496.
Younes, N.A. et al., "Laboratory screening for hyperparathyroidism," Clin Chim Acta. (2005) 353(1-2):1-12.
Zang, X.Y. et al., "Effects of parathyroid hormone and estradiol on proliferation and function of human osteoblasts from fetal long bone: An in vitro study," Chin Med J (Engl). (1994) 107(8):600-3.
Zaruba, M.M. et al., "Parathyroid hormone treatment after myocardial infarction promotes cardiac repair by enhanced neovascularization and cell survival," Cardiovasc Res (2008) 77(4):722-731.
Zhou, H. et al., "Anabolic action of parathyroid hormone on cortical and cancellous bone differs between axial and appendicular skeletal sites in mice," Bone (2003) 32(5):513-520.
Shin, H., et al. Efficacy of Interventions for Prtevention of Chemotherapy-Induced Alopecia: A systematic review and meta-analysis. International Journal of Cancer. 2015. 136: E442-E454.
Shinoda, Y. et al., "Mechanisms underlying catabolic and anabolic functions of parathyroid hormone on bone by combination of culture systems of mouse cells," J. of Cellular Biology (2010) 109(4):755-63.
Sides, C. R., et al. (2012). "Probing the 3-D Structure, Dynamics, and Stability of Bacterial Collagenase Collagen Binding Domain (apo—versus holo-) by Limited Proteolysis MALDI-TOF MS." Journal of the American Society for Mass Spectrometry 23(3): 505-519.
Silver, J. et al., "Harnessing the parathyroids to create stronger bones," Curr Opin Nephrol Hypertens. (2004) 13(4):471-6.
Silverberg, S.J. et al., "Skeletal disease in primary hyperparathyroidism," J Bone Miner Res., (1989) 4(3):283-91.
Skripitz, R. et al., "Parathyroid hormone—a drug for orthopedic surgery?," Acta Orthop Scand. (2004) 75(6):654-62.
Skripitz, R. et al., "Stimulation of implant fixation by parathyroid hormone (1-34)—A histomorphometric comparison of PMMA cement and stainless steel," J Orthop Res. (2005) 23(6):1266-70. Epub Jun. 16, 2005.
Smajilovic, S. et al., "Effect of intermittent versus continuous parathyroid hormone in the cardiovascular system of rats," Open Cardiovasc. Med. J. (2010) 4:110-6.
Spiriti, J. et al (2010). "Mechanism of the calcium-induced trans-cis isomerization of a non-prolyl peptide bond in Clostridium histolyticum collagenase." Biochemistry 49(25): 5314-5320.
Spurney, R.F. et al., "Anabolic effects of a G protein-coupled receptor kinase inhibitor expressed in osteoblasts," J Clin Invest. (2002) 109(10):1361-71.
Stewart, A.F., "PTHrP(1-36) as a skeletal anabolic agent for the treatment of osteoporosis," Bone (1996) 19(4):303-306.
Stracke, S. et al., "Long-term outcome after total parathyroidectomy for the management of secondary hyperparathyroidism," Nephron Clin Pract. (2009) 111(2):c102-9. Epub Jan. 13, 2009.
Stratford, R., Jr., et al (2014). "Pharmacokinetics in rats of a long-acting human parathyroid hormone-collagen binding domain peptide construct." J Pharm Sci 103(2): 768-775.
Strewler, G.J., "Local and systemic control of the osteoblast," J. of Clin. Invest. (2001) 107:271-272.
Suttamanatwong, S. et al., "Regulation of matrix Gla protein by parathyroid hormone in MC3T3-E1 osteoblast-like cells involves protein kinase A and extracellular signal-regulated kinase pathways," J Cell Biochem. (2007) 102(2):496-505.
Suttamanatwong, S. et al., "Sp proteins and Runx2 mediate regulation of matrix gla protein (MGP) expression by parathyroid hormone," J Cell Biochem. (2009) 107(2):284-92.
Suzuki, A. et al., "PTH/cAMP/PKA signaling facilitates canonical Wnt signaling via inactivation of glycogen synthase kinase-3beta in osteoblastic Saos-2 cells," J Cell Biochem. (2008) 104(1):304-17.

(56) References Cited

OTHER PUBLICATIONS

Swarthout, J.T. et al., "Parathyroid hormone-dependent signaling pathways regulating genes in bone cells," Gene (2002) 282(1-2):1-17.
Swarthout, J.T. et al., "Stimulation of extracellular signal-regulated kinases and proliferation in rat osteoblastic cells by parathyroid hormone is protein kinase C-dependent," J Biol Chem. (2001) 276(10):7586-92. Epub Dec. 6, 2000.
Takada, H. et al., "Response of parathyroid hormone to anaerobic exercise in adolescent female athletes," Acta Paediatr Jpn. (1998) 40(1):73-7.
Takasu, H. et al., "Dual signaling and ligand selectivity of the human PTH/PTHrP receptor," J Bone Miner Res. (1999) 14(1):11-20.
Talmage, R.V. et al., "Calcium homeostasis: reassessment of the actions of parathyroid hormone," Gen Comp Endocrinol. (2008) 156(1):1-8. Epub Nov. 12, 2007.
Tam, C.S. et al., "Parathyroid hormone stimulates the bone apposition rate independently of its resorptive action: differential effects of intermittent and continuous administration," Endocrinology (1982) 110(2):506-12.
Tawfeek, H. et al., "Disruption of PTH receptor 1 in T cells protects against PTH-induced bone loss," PLoS (2010) 5(8):e12290.
Tokumoto, M. et al., "Parathyroid cell growth in patients with advanced secondary hyperparathyroidism: vitamin D receptor, calcium sensing receptor, and cell cycle regulating factors," Ther Apher Dial. (2005) 9(Suppl 1):S27-34.
Tollin, S.R. et al., "Serial changes in bone mineral density and bone turnover after correction of secondary hyperparathyroidism in a patient with pseudohypoparathyroidism type Ib," J Bone Miner Res. (2000) 15(7):1412-6.
Toyoshima, T. et al., "Collagen-binding domain of a Clostridium histolyticum collagenase exhibits a broad substrate spectrum both in vitro and in vivo," Connective Tissue Research (2001) 42(4):281-290.
Uchida K, et al: Acceleration of periosteal bone formation by human basic fibroblast growth factor containing a collagen-binding domain from Clostridium histolyticum collagenase. J Biomed Mater Res A 2014;102:1737-1743.
Uchida, K. et al. "Enhancement of periosteal bone formation by basic fibroblast-derived growth factor containing polycystic kidney disease and collagen-binding domains from Clostridium histolyticum collagenase" J. Tissue Eng Regen Med (2017) 11(4):1165-1172.
Ueno M, et al: Influence of internal fixator stiffness on murine fracture healing: two types of fracture healing lead to two distinct cellular events and FGF-2 expressions. Exp Anim 2011;60:79-87.
Ueno, M., et al (2014). "Acceleration of bone union after structural bone grafts with a collagen-binding basic fibroblast growth factor anchored-collagen sheet for critical-size bone defects." Biomed Mater 9(3): 035014.
United States Patent Office Action for U.S. Appl. No. 12/594,547 dated Aug. 6, 2012 (12 pages).
United States Patent Office Action for U.S. Appl. No. 14/365,226 dated Nov. 24, 2015 (8 pages).
United States Patent Office Action for U.S. Appl. No. 14/365,226 dated Jun. 10, 2016 (9 pages).
United States Patent Office Action for U.S. Appl. No. 14/378,067 dated Feb. 17, 2016 (16 pages).
United States Patent Office Action for U.S. Appl. No. 15/407,589 dated Jun. 26, 2018 (44 pages).
United States Patent Office Action for U.S. Appl. No. 15/407,589 dated Jun. 26, 2019 (7 pages).
Uzawa, T. et al., "Comparison of the effects of intermittent and continuous administration of human parathyroid hormone(1-34) on rat bone," Bone (1995) 16(4):477-84.
Vanstone, M.B. et al., "Rapid correction of bone mass after parathyroidectomy in an adolescent with primary hyperparathyroidism," J. Clin. Endocrinol. Metab. (2011) 96(2): E347-50. Epub Nov. 24, 2010.
Wan, Q. et al., "Intra-articular injection of parathyroid hormone in the temporomandibular joint as a novel therapy for mandibular asymmetry," Med Hypotheses (2009) 74(4):685-7.
Wang, C.A. et al., "Natural history of parathyroid carcinoma. Diagnosis, treatment, and results," Am J Surg. (1985) 149(4):522-7.
Wang, Y. et al., "A theoretical model for simulating effect of parathyroid hormone on bone metabolism at cellular level," Mol Cell Biomech. (2009) 6(2):101-12.
Wang, Y. et al., "Gender differences in the response of CD-1 mouse bone to parathyroid hormone: potential role of IGF-I," J Endocrinol. (2006) 189(2):279-87.
Watanabe-Nakayama, T., et al (2016). "High-speed atomic force microscopy reveals strongly polarized movement of clostridial collagenase along collagen fibrils." Sci Rep 6: 28975.
Watson, P.H. et al., "Enhanced osteoblast development after continuous infusion of hPTH(1-84) in the rat," Bone (1999) 24(2):89-94.
Weir, E.C. et al., "Synthetic parathyroid hormone-like protein (1-74) is anabolic for bone in vivo," Calcif Tissue Int. (1992) 51(1):30-4.
Whitfield, J.F., "Taming Psoriatic Keratinocytes-PTHs' uses go up another notch," J. Cell. Biochem. (2004) 93:251-256.
Wilson, J.J. et al., "A bacterial collagen-binding domain with novel calcium-binding motif controls domain orientation," EMBO Journal (2003) 22(8)1743-1752.
Xu, M. et al., "Basal bone phenotype and increased anabolic responses to intermittent parathyroid hormone in healthy male COX-2 knockout mice," Bone (2010) 47(2):341-52. Epub May 13, 2010.
Yang, C. et al., "Effects of continuous and pulsatile PTH treatments on rat bone marrow stromal cells," Biochem Biophys Res Commun. (2009) 380(4):791-6. Epub Feb. 3, 2009.
Okazaki, R., "Parathyroid hormone—its mechanisms of action and issues on clinical application," Clin Calcium. (2005) 15(5):845-51.
Olgaard, K. et al., "Can hyperparathyroid bone disease be arrested or reversed?," Clin J Am Soc Nephrol. (2006) 1(3):367-73. Epub Mar. 29, 2006.
Onyia, J.E. et al., "Molecular profile of catabolic versus anabolic treatment regimens of parathyroid hormone (PTH) in rat bone: an analysis by DNA microarray," J Cell Biochem. (2005) 95(2):403-18.
Owens, R.J. et al., "Mapping the collagen-binding site of human fibronectin by expression in *Escherichia coli*," The EMBO Journal (1986) 5(11)2825-2830.
Paillard, M. et al., "Determinants of parathormone secretion in primary hyperparathyroidism," Horm Res. (1989) 32(1-3):89-92.
Parfitt, A.M. et al., "Hypercalcemia due to constitutive activity of the parathyroid hormone (PTH)/PTH-related peptide receptor: comparison with primary hyperparathyroidism," J Clin Endocrinol Metab. (1996) 81(10):3584-8.
Parfitt, A.M., "The actions of parathyroid hormone on bone: relation to bone remodeling and turnover, calcium homeostasis, and metabolic bone disease. Part IV of IV parts: The state of the bones in uremic hyperaparathyroidism—the mechanisms of skeletal resistance to PTH in renal failure and pseudohypoparathyroidism and the role of PTH in osteoporosis, osteopetrosis, and osteofluorosis," Metabolism. (1976) 25(10):1157-88.
Partial Supplementary European Search Report dated Oct. 1, 2015 (7 pages).
Peters, E.M.J. et al., "A new strategy for modulating chemotherapy-induced alopecia, using PTH/PTHrP receptor agonist and antagonist," J Invest Dermatol (2001) 117(2):173-178.
Pettway, et al., "Anabolic actions of PTH (1-34): Use of a novel tissue engineering model to investigate temporal effects on bone," Bone (2005) 36(6):959-970.
Phelps, E. et al., "Parathyroid hormone induces receptor activity modifying protein-3 (RAMP3) expression primarily via 3',5'-cyclic adenosine monophosphate signaling in osteoblasts," Calcif Tissue Int. (2005) 77(2):96-103. Epub Aug. 11, 2005.
Philominathan et al., "Bacterial collagen-binding domain targets undertwisted regions of collagen," Protein Sci. (2012) 21(10):1554-65.

(56) References Cited

OTHER PUBLICATIONS

Philominathan et al., "Unidirectional binding of Clostridial Collagenase to Triple Helical Substrates," Journal of Biological Chemistry (2009) 284(16):10868-10876.
Philominathan, S. T., et al (2009). "Ca2+-induced linker transformation leads to a compact and rigid collagen-binding domain of Clostridium histolyticum collagenase." FEBS J 276(13): 3589-3601.
Pirih, F.Q. et al., "Parathyroid hormone induces the NR4A family of nuclear orphan receptors in vivo," Biochem Biophys Res Commun. (2005) 332(2):494-503.
Podbesek, R. et al., "Effects of two treatment regimes with synthetic human parathyroid hormone fragment on bone formation and the tissue balance of trabecular bone in greyhounds," Endocrinology (1983) 112(3):1000-6.
Ponnapakkam, T. et al., "A fusion protein of parathyroid hormone (PTH) and a collagen binding domain shows superior efficacy and longer duration of action compared to PTH(1-34) as an anabolic bone agent in normal female mice," Bone (2009) 44:S35-S36.
Ponnapakkam, T. et al., "A Single Injection of the Anabolic Bone Agent, Parathyroid Hormone-Collagen Binding Domain (PTH-CBD), Results in Sustained Increases in Bone Mineral Density for up to 12 Months in Normal Female Mice" Calcified Tissue (2012) 91(30:196-203.
Ponnapakkam, T., et al (2011). "Prevention of chemotherapy-induced osteoporosis by cyclophosphamide with a long-acting form of parathyroid hormone." J Endocrinol Invest 34(11): e392-397.
Ponnapakkam, T., et al., "Monthly administration of a novel PTH-collagen binding domain fusion protein is anabolic in mice," Calcif Tissue Int.2011;88:511-520.
Poole, K.E. et al., "Parathyroid hormone—a bone anabolic and catabolic agent," Curr Opin Pharmacol. (2005) 5(6):612-7. Epub Sep. 21, 2005.
Potter, L.K. et al., "Response to continuous and pulsatile PTH dosing: a mathematical model for parathyroid ormone receptor kinetics," Bone (2005) 37(2):159-169.
Potts, J.T., "Parathyroid hormone: past and present," J Endocronology (2005) 187:311-325.
Proesmans, W. & Van Dyck, M. "Enalapril in children with Alport syndrome" Pediatr Nephrol (2004) 19:271-275.
Qin, L. et al., "Parathyroid hormone: a double-edged sword for bone metabolism," Trends Endocrinol Metab. (2004) 15(2):60-5.
Rattanakul, C. et al., "Modeling of bone formation and resorption mediated by parathyroid hormone: response to estrogen/PTH therapy" Biosystems (2003) 70(1):55-72.
Restriction Requirement for U.S. Appl. No. 14/365,226 dated Jun. 22, 2015 (8 pages).
Restriction Requirement for U.S. Appl. No. 14/378,067 dated Oct. 23, 2015 (9 pages).
Restriction requirement for U.S. Appl. No. 14/743,629 dated Apr. 20, 2016 (8 pages).
Restriction requirement for U.S. Appl. No. 15/407,589 dated Jan. 8, 2018 (5 pages).
Richardson, M.L. et al., "Bone mineral changes in primary hyperparathyroidism," Skeletal Radiol. (1986) 15(2):85-95.
Rickard, D.J. et al., "Intermittent treatment with parathyroid hormone (PTH) as well as a non-peptide small molecule agonist of the PTH1 receptor inhibits adipocyte differentiation in human bone marrow stromal cells," Bone (2006) 39(6):1361-1372. Epub Aug. 10, 2006.
Rixon, R.H. et al., "Parathyroid hormone fragments may stimulate bone growth in ovariectomized rats by activating adenylyl cyclase," J Bone Miner Res. (1994) 9(8):1179-89.
Robinson, J.A. et al., "Identification of a PTH regulated gene selectively induced in vivo during PTH-mediated bone formation," J Cell Biochem. (2006) 98(5):1203-20.
Rosen, C.J., "The cellular and clinical parameters of anabolic therapy for osteoporosis," Crit Rev Eukaryot Gene Expr. (2003) 13(1):25-38.
Rubin, M. et al., "The anabolic effects of parathyroid hormone therapy," Osteoporosis International (2002) 13(4):267-277.
Rubin, M.R. et al., "The anabolic effects of parathyroid hormone therapy," Clin Geriatr Med. (2003) 19(2):415-32.
Rubin, M.R. et al., "The potential of parathyroid hormone as a therapy for osteoporosis," Int J Fertil Womens Med. (2002) 47(3):103-15.
Safer, J.D. et al., "A topical parathyroid hormone/parathyroid hormone-related peptide receptor antagonist stimulates hair growth in mice," Endocrinology (2007)148:1167-1170.
Saito W, et al: Acceleration of bone formation during fracture healing by injectable collagen powder and human basic fibroblast growth factor containing a collagen-binding domain from Clostridium histolyticum collagenase. J Biomed Water Res A 2014;102:3049-3055.
Saito W, et al: Acceleration of callus formation during fracture healing using basic fibroblast growth factor-kidney disease domain-collagen-binding domain fusion protein combined with allogenic demineralized bone powder. J Orthop Surg Res 2015;10:59.
Schaefer, F., "Pulsatile parathyroid hormone secretion in health and disease," Novartis Found Symp. (2000) 227:225-39; discussion 239-43.
Schilli, M.B. et al., "Control of hair growth with parathyroid hormone (7-34)," J Invest Dermatol (1997) 108:928-932.
Schluter, K.-D. et al., "A N-terminal PTHrP peptide fragment void of a PTH/PTHrP-receptor binding domain activates cardiac ETA receptors," British Journal of Pharmacology (2001) 132:427-432.
Schmitt, C.P. et al., "Intermittent administration of parathyroid hormone (1-37) improves growth and bone mineral density in uremic rats," Kidney Int. (2000) 57(4):1484-92.
Schmitt, C.P. et al., "Structural organization and biological relevance of oscillatory parathyroid hormone secretion," Pediatr Nephrol. (2005) 20(3):346-51. Epub Feb. 8, 2005.
Schneider, A. et al., "Skeletal homeostasis in tissue-engineered bone," J Orthop Res. (2003) 21(5):859-64.
Seeman, E. et al., "Reconstructing the skeleton with intermittent parathyroid hormone," Trends Endocrinol Metab. (2001) 12(7):281-3.
Sekiguchi, H. et al., "Acceleration of bone formation during fracture healing by poly(pro-hyp-gly)10 and basic fibroblast growth factor containing polycystic kidney disease and collagen-binding domains from Clostridium histolyticum collagenase" J. Biomed Mater Res A. (2016) 104(6):1372-1378.
Shen, V. et al., "Skeletal effects of parathyroid hormone infusion in ovariectomized rats with or without estrogen repletion," J Bone Miner Res. (2000) 15(4):740-6.
Fox, J. et al., "Effects of daily treatment with parathyroid hormone 1-84 for 16 months on density, architecture and biomechanical properties of cortical bone in adult ovariectomized rhesus monkeys," Bone (2007) 41(3):321-330.
Fraher, L.J. et al., "Comparison of the biochemical responses to human parathyroid hormone-(1-31)NH2 and hPTH-(1-34) in healthy humans," J Clin Endocrinol Metab. (1999) 84(8):2739-43.
Frolik, C.A. et al., "Anabolic and catabolic bone effects of human parathyroid hormone (1-34) are predicted by duration of hormone exposure," Bone (2003) 33(3):372-379.
Fujimaki, H., et al (2016). "Oriented collagen tubes combined with basic fibroblast growth factor promote peripheral nerve regeneration in a 15 mm sciatic nerve defect rat model." J Biomed Mater Res A.
Fujita, T., "Parathyroid hormone in the treatment of osteoporosis," BioDrugs (2001) 15(11):721-728.
Fukayama, S. et al., "New insights into interactions between the human PTH/PTHrP receptor and agonist/antagonist binding," Am. J. Physiol. Endocrinol. Metab. (1998) 274:297-303.
Gao, Y. et al., "T cells potentiate PTH-induced cortical bone loss through CD40L signaling," Cell Metab. (2008) 8(2):132-45.
Gardella, T.J. et al., "Converting Parathyroid Hormone-related Peptide (PTHrP) into a Potent PTH-2 Receptor Agonist," J. of Biological Chemistry, (1996) 271(33):19888-19893.
Gaston, R. G., et al (2015). "The Efficacy and Safety of Concurrent Collagenase Clostridium Histolyticum Injections for 2 Dupuytren Contractures in the Same Hand: A Prospective, Multicenter Study." J Hand Surg Am 40(10):1963-1971.

(56) References Cited

OTHER PUBLICATIONS

Gensure, R.C. et al., "Parathyroid hormone and parathyroid hormone-related peptide, and their receptors," Biochem Biophys Res Commun. (2005) 328(3):666-78.
Gensure, R.C. et al., "Parathyroid hormone without parathyroid glands," Endocrinology (2005) 146(2):544-546.
Gensure, R.C. et al., "Parathyroid hormone-related peptide and the hair cycle—is it the agonists or the antagonists that cause hair growth?" (2014) Experimental Dermatology, 23(12):865-867.
Gevers, E.F.et al., "Bone marrow adipocytes: a neglected target tissue for growth hormone," Endocrinology (2002) 143(10):4065-73.
Goltzman, D., "Studies on the mechanisms of the skeletal anabolic action of endogenous and exogenous parathyroid hormone," Arch Biochem Biophys. (2008) 473(2):218-24. Epub Mar. 10, 2008.
Gopalakrishnan, R. et al., "Role of matrix Gla protein in parathyroid hormone inhibition of osteoblast mineralization," Cells Tissues Organs (2005) 181(3-4):166-75.
Gosavi, A. et al., "An unusual presentation of parathyroid adenoma—a case report," Indian J Pathol Microbiol. (2005) 48(2):208-10.
Gu, W.X. et al., "Mutual up-regulation of thyroid hormone and parathyroid hormone receptors in rat osteoblastic osteosarcoma 17/2.8 cells," Endocrinology (2001) 142(1):157-64.
Hall, A.K. et al., "The effects of parathyroid hormone on osteoblast-like cells from embryonic chick calvaria," Acta Endocrinol (Copenh). (1985) 108(2):217-23.
Han X, et al: Accelerated postero-lateral spinal fusion by collagen scaffolds modified with engineered collagen-binding human bone morphogenetic protein-2 in rats. PLoS One 2014;9:e98480.
Han, B. et al., "Collagen-targeted BMP3 fusion proteins arrayed on collagen matrices or porous ceramics impregnated with Type I collagen enhance osteogenesis in a rat cranial defect model," J Orthopaedic Research (2002) 20:747-755.
Headley, C.M., "Hungry bone syndrome following parathyroidectomy," Anna J., (1998) 25(3):283-9; quiz 290-1.
Heath, H., 3rd, "Clinical spectrum of primary hyperparathyroidism: evolution with changes in medical practice and technology," J Bone Miner Res. (1991) 6(Suppl 2):S63-70; discussion S83-4.
Hoare, S.R. et al., "Specificity and stability of a new PTH1 receptor antagonist, mouse TIP(7-39)," Peptides (2002) 23(5):989-998.
Hock, J.M. et al., "Effects of continuous and intermittent administration and inhibition of resorption on the anabolic response of bone to parathyroid hormone," J Bone Miner Res. (1992) 7(1):65-72.
Hock, J.M. et al., "Human parathyroid hormone-(1-34) increases bone mass in ovariectomized and orchidectomized rats," Endocrinology (1988) 122(6):2899-2904.
Holick, M.F. et al., "Topical PTH (1-34) is a novel, safe and effective treatment for psoriasis: a randomized self-controlled trial and an open trial," (2003) British J. Dermatology 149:370-376.
Homme, M. et al., "Differential regulation of RGS-2 by constant and oscillating PTH concentrations," Calcif Tissue Int. (2009) 84(4):305-12. Epub Feb. 20, 2009.
Horwitz, M.J. et al., "Continuous PTH and PTHrP infusion causes suppression of bone formation and discordant effects on 1,25(OH)2 vitamin D," J Bone Miner Res. (2005) 20(10):1792-803. Epub Jun. 6, 2005.
Horwitz, M.J. et al., "Parathyroid hormone-related protein for the treatment of postmenopausal osteoporosis: defining the maximal tolerable dose," J Clin Endocrinol Metab. (2010) 95(3):1279-87.
Hruska, K.A. et al., "Regulation of skeletal remodeling by parathyroid hormone," Contrib Nephrol. (1991) 91:38-42.
Iida-Klein, A. et al., "Short-term continuous infusion of human parathyroid hormone 1-34 fragment is catabolic with decreased trabecular connectivity density accompanied by hypercalcemia in C57BL/J6 mice," J Endocrinol. (2005) 186(3):549-57.
International Search Report and Written Opinion of the International Searching Authority for Application No. PCT/US08/004589 dated Oct. 28, 2008 (17 pages).
International Search Report and Written Opinion of the International Searching Authority for Application No. PCT/US12/69831 dated Mar. 14, 2013 (12 pages).
International Search Report and Written Opinion of the International Searching Authority for Application No. PCT/US2013/25541 dated Jun. 17, 2013 (16 pages).
International Search Report and Written Opinion of the International Searching Authority for Application No. PCT/US2018/017665 dated May 7, 2018 (11 pages).
Ishii, H. et al., "Daily intermittent decreases in serum levels of parathyroid hormone have an anabolic-like action on the bones of uremic rats with low-turnover bone and osteomalacia," Bone (2000) 26(2):175-82.
Ishikawa, T. et al., "Delivery of a growth factor fusion protein having collagen-binding activity to wound tissues," Artif. Organs (2003) 27(2):147-154.
Ishikawa, T. et al., "Production of a biologically active epidermal growth factor fusion protein with high collagen affinity," J. Biochem. (2001) 129(4)627-633.
Ishizuya, T. et al., "Parathyroid hormone exerts disparate effects on osteoblast differentiation depending on exposure time in rat osteoblastic cells," J Clin Invest. (1997) 99(12):2961-70.
Ito, M., "Parathyroid and bone: Effect of parathyroid hormone on bone quality," Clin Calcium. (2007) 17(12):1858-64.
Ito, M., "Parathyroid hormone and bone quality," Clin Calcium. (2005) 15(12):31-7.
Jeon, E. et al., "Engineering and application of collagen-binding fibroblast growth factor 2 for sustained release," (2013) J. of Biomed. Materials Research: Part A.
Jilka, R.L. et al., "Continuous elevation of PTH increases the number of osteoblasts via both osteoclast-dependent and -independent mechanisms," J Bone Miner Res. (2010) 25(11):2427-37.
Jilka, R.L., "Molecular and cellular mechanisms of the anabolic effect of intermittent PTH," Bone (2007) 40(6):1434-1446. Epub Apr. 6, 2007.
Kaji, H., "Parathyroid and bone: Effects of parathyroid hormone on bone resorption and formation: differences between intermittent and continuous treatment," Clin Calcium., (2007) 17(12):1836-42.
Katikaneni et al., "Therapy for alopecia areata in mice using parathyroid hormone agonists and antagonists, linked to a collagen-binding domain," J. of Investigative Dermatology Symposium Proceedings, (2013) 16(1):S61-S62.
Katikaneni et al., "Treatment for chemotherapy-induced alopecia in mice using parathyroid hormone agonists and antagonists linked to coolagen binding domain," Int. J. Cancer (2012) 131(5):E813-821.
Katikaneni R., et al. Parathyroid hormone linked to a collagen binding domain (PTH-CBD) promotes hair growth in a mouse model of chemotherqapy-induced alopecia in a dose-dependent manner. Anticancer Drugs. 2014. 25(7):819-825.
Katikaneni, R. et al. Therapy for alopecia Areata in Mice by Stimulating the Hair Cycle with Parathyroid Hormone Agonists Linked to a Collagen-Binding Domain. The Journal of Investigative Dermatology Symposium. 2015. 17: 13-15.
Katikaneni, R. et al. Treatment and Prevention of Chemotherapy-induced alopecia with PTH-CBD, a collagen targeted parathyroid hormone analog, in a non-depilated mouse model. Anticancer Drugs. 2014. 25(1): 30-38.

* cited by examiner

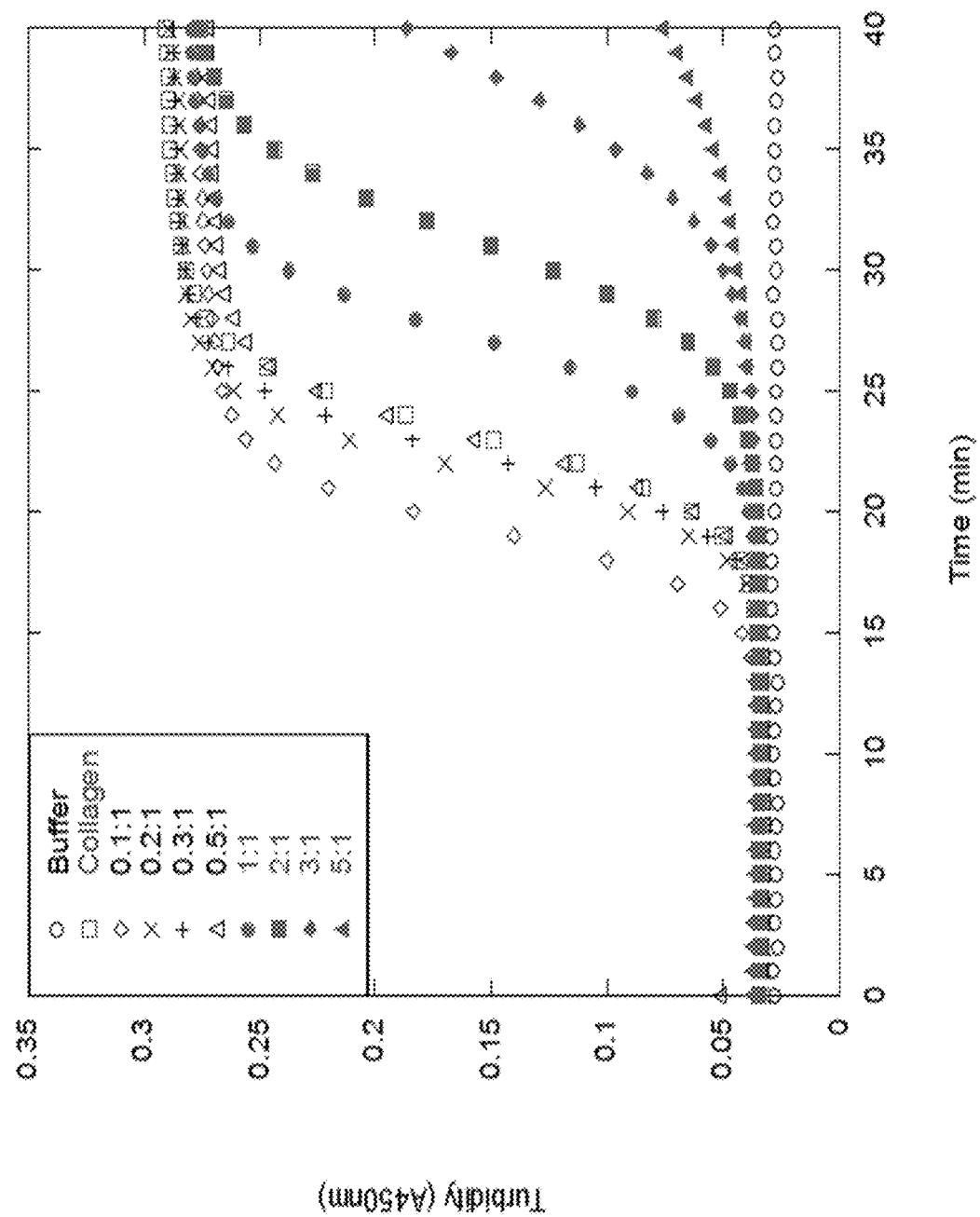

Fig. 5

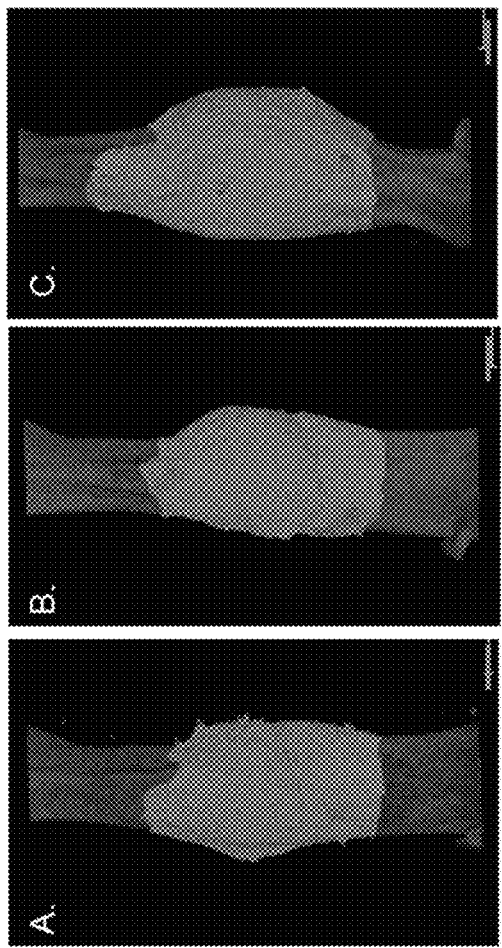

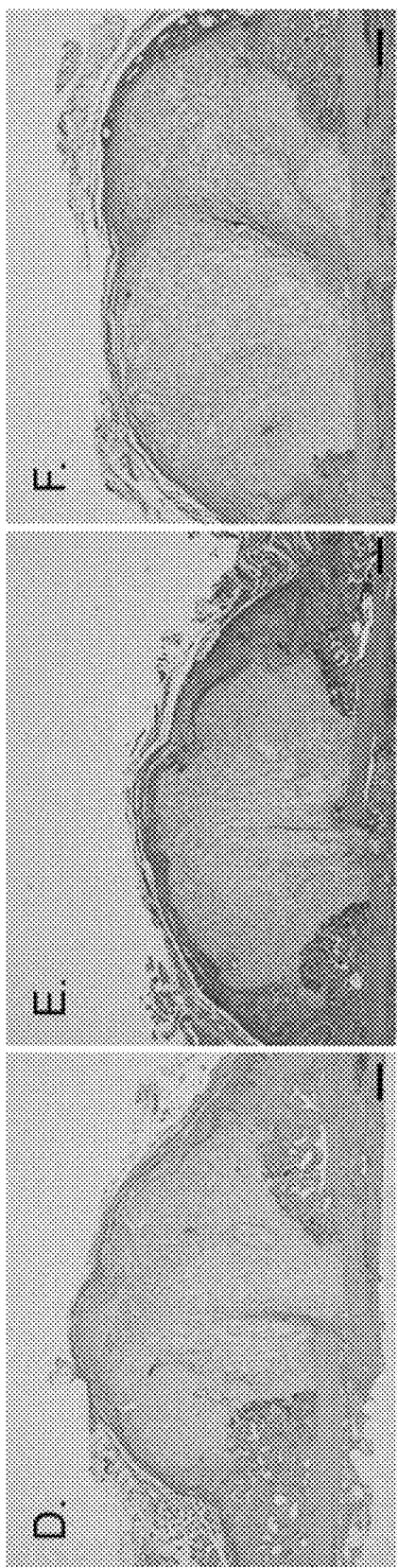
Fig. 10A  Fig. 10B  Fig. 10C  Fig. 10D  Fig. 10E  Fig. 10F Fig. 12 (continued)

```
                            G              H              I
                         ───▶          ───▶           ───▶
                         980            990           1000

ColG s3b         -GNKVSMKVKL-RPGKYYLLVYKYSG--SGN ELRVN
Csporogenes C    -GSTIVGNCHV-TPKKYYLYYKYSG-NMGN SLIIK
Cbotulinum A3C   -GNTIKGKCNV-APGKYLYYKYSG-DNGN SIAIK
Bcereus_AH603    -GNHIEANFNA-KPGKYYLYVYKYDN-GDGT ELSVK
Banthracis       -GNHIEANFNA-KPGKYYLYVYKYDN-GDGT ELSVK
BB14905 B        -GMINGKWNA-KPGKYYLYVKFEN-ENGT TVHVQ
Lsphaericus B    -GNMINGKLHA-EPGKYLYVKFEN-ENGT TVQVQ
CcerusG9842      -GNVVKGTYNA-KPGKYYLYVKYEN-KDGS VLNIK
Bmycoides        -GNKLVGSYNA-HPGKYLEVYQYGG-GTGN TEVK
Bweihensteph     DGNKLLGNYNA-KPGKYLSVYKYGG-GTGN TEVK
Bbrevis A        -GKTLSGEPEA-TPGTYLSVNFNG-ETIP KVTAE
Bbrevis B        -GKKLTGEFEA-KPGKYLLVYNFNN-TKIP KAIVN
Cperfringens B   -GNKLSNTCKL-NPGKYYLCVYQPENSGTGN TVNLQ
Csporogenes B    EGNKLMGSFKVPKPGKYYLLAYKNSS-NKIN KLTIN
Cbotulinum A3B   EGNKITGNFKVDKPGKYYVAYKTSS-NKIN KLNIK
Csporogenes A    LGNQLSNTVKINKPGKYYLVIYKTLG-EKVD KPSIE
Cbotulinum A3A   LENLFYSTVKDKPGKYLVIYVSG-EKSD RFNIE
Csordellii B     IDNKINGKVDL-KVTYYLEVYGYGS-SPVK NFKVT
ColG s3a         -NNSKVGTFKSTK-GHHYVFIYKHDSASNIS SINIK
Cperfringens A   EGTVLKGEKTLE-PGHYYLSVYTYDN-QSGA TVNVK
Csordellii A     -GAILNGDYNATKPGKYYLLVYNHDK-SLAN NLKVN
ColH s3          -GQNLSGKFKADKPGKYTIHLYMFNG-SYMP RJNIE ───▶        ───▶          ───▶
                  950         960           970
                   G           H             I
```

COLLAGEN-BINDING AGENT COMPOSITIONS AND METHODS OF USING THE SAME

CROSS-REFERENCE TO RELATED APPLICATIONS

The present application is a national stage filing under U.S.C. 371 of International Application No. PCT/US2018/017665 filed Feb. 9, 2018, which claims the benefit of priority of U.S. Provisional Patent Application No. 62/457,410, filed on Feb. 10, 2017, the contents of which are incorporated herein by reference in their entirety.

STATEMENT REGARDING FEDERALLY SPONSORED RESEARCH

This invention was made with government support under grant number RR015569 and RR016460 awarded by the National Institute of Health. The United States government has certain rights in the invention.

SEQUENCE LISTING

This application is being filed electronically via EFS-Web and includes an electronically submitted Sequence Listing in .txt format. The .txt file contains a sequence listing entitled "2018-02-09_5965-00084_ST25.txt" created on Feb. 9, 2018 and is 72,312 bytes in size. The Sequence Listing contained in this .txt file is part of the specification and is hereby incorporated by reference herein in its entirety.

Introduction

Collagen is the primary structural protein found in the extracellular space of various animal tissues. Collagen, for example, can be found in fibrous tissues such as skin, ligaments, and tendons. It is also abundant in bones, cartilage, corneas, blood vessels, and muscle tissues.

Abnormal or damaged collagen underlies several medical conditions including wounding and collagenopathies. Collagenopathies represent a large number of diseases in which collagen structure or formation is not normal. This group of diseases results in a broad spectrum of symptoms including bone defects, vascular defects, and skin defects. Many of these diseases have no or only ineffective treatments available.

Collagen-targeting agents are also attractive agents for delivering therapeutics to different animal tissues or subsites within a particular tissue. Delivery of therapeutic agents to sites within the body of a subject where a particular therapeutic agent is needed in order to be effective is a developing area. Targeted delivery systems allow the therapeutic agents to be most active at the sites where the agent is needed while minimizing the off-site effects of the therapeutic agent which may lead to unwanted toxicity and side effects. While use of targeted liposomes or polypeptides, such as antibodies, to target therapeutic agents to particular sites within the body has proved successful, additional delivery agents are needed. There thus is a need in the art for new collagen-targeting agents that may be used to treat tissues with damaged or normal collagen or to deliver appropriate therapeutics to such tissues.

SUMMARY

In one aspect, collagen-binding agents are provided. The collagen-binding agents may include two collagen-binding domains linked by a domain linker. The two collagen-binding domains may be selected from any one of the polypeptides of SEQ ID NOs: 1-47, a variant of the polypeptides of SEQ ID NOs: 1-47, or a fragment of the polypeptides of SEQ ID NOs: 1-47. SEQ ID NOs: 1-39 specify individual collagen-binding domains (i.e., ColG s3a, ColG s3b, ColH s3) from ColG and ColH proteins from various bacterial species. SEQ ID NOs: 40-47 specify tandem collagen-binding domains found in ColG proteins from various bacterial species. See, also, FIG. 5. The collagen-binding agents of the present invention may further include a therapeutic agent linked to the collagen-binding agent by a therapeutic agent linker. The therapeutic agent may be selected from FGF, parathyroid hormone (PTH), PTH/PTHrP receptor agonist, PTH/PTHrP receptor antagonist, bone morphogenic protein (BMP), G-CSF, BMP-2, BMP-3, anti-sclerostin antibody, growth hormone, IGF-1, VEGF, TGF-β, KGF, TGF-α, TGF-β1, TGF-β receptor, CT, GH, GM-CSF, EGF, PDGF, celiprolol, activins and connective tissue growth factors.

In another aspect, pharmaceutical compositions are provided. The pharmaceutical compositions may include any of the collagen-binding agents described herein and a pharmaceutical carrier.

In a further aspect, methods of treating a condition are also provided. The methods may include administering any of collagen-binding agents or pharmaceutical compositions described herein to a subject in an amount effective to treat the condition.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 3 shows the influence of collagen binding on self-assembly of collagen type I.

FIG. 5 shows a sequence alignment of bacterial tandem collagen binding domains (See SEQ ID NOs: 40-47). Residues binding to collagen are highlighted in blue. Calcium-binding residues are in red, structurally important residues are shown in green.

FIGS. 8A-8F show 3D micro-CT analysis of femurs after injection of poly(Pro-Hyp-Gly)$_{10}$ loaded with bFGF and CB-bFGFs. 3D micro-CT images of fractured mouse femurs treated with (FIG. 8A) PBS, (FIG. 8B) bFGF, (FIG. 8C) bFGF-CBD(H), (FIG. 8D) bFGF-PKD-CBD, (FIG. 8E) bFGF-CBD-CBD (FIG. 8F) after 4 weeks of recovery. Red: newly formed bone; gray: existing bone. The scale bars indicate 3 mm.

FIG. 9A is a graph showing callus volume (mm$^3$) and FIG. 9B is a graph showing bone mineral content. Data are presented as the mean±S.E. (n=8). Lower case letters above the bars in the graph are defined as follows: a, P<0.05 compared with the control group. b, P<0.05 compared with the bFGF group. c, P<0.05 compared with the bFGF-CBD (H) group. d, P<0.05 compared with the bFGF-PKD-CBD group. e, P<0.05 compared with the bFGF-CBD(G) group.

FIGS. 10A-10F show representative hematoxylin and eosin-stained tissue sections on day 14 of fracture healing. Histological images of fractured mouse femurs treated with (FIG. 10A) PBS, (FIG. 10B) bFGF, (FIG. 10C) bFGF-CBD (ColH s3), (FIG. 10D) bFGF-PKD-CBD (ColH s2b-s3), (FIG. 10E) bFGF-CBD (ColG s3b), and (FIG. 10F) bFGF-CBD-CBD (s3a-s3b) after 14 days of recovery. Scale bar=500 µm.

DETAILED DESCRIPTION

In the non-limiting Examples, the present inventors report the high-resolution structure of a bacterial tandem collagen-binding agent for the first time. The pseudo-symmetrical arrangement of the tandem collagen-binding agent, resulting from gene duplication and fusion, could allow it to recognize a unique niche in collagen fibril to facilitate degradation of collagen. The structure of the tandem collagen-binding agent also reveals that it could wedge between parallel collagen molecules. This structure combined with the previously identified collagen-binding domain preference for under-twisted regions of collagen suggests the tandem collagen-binding agent targets the bacterial collagenase, ColG, to damaged regions of the collagen fibril. Based on this new understanding of how tandem collagen-binding agent interacts with collagen, the present inventors disclose new collagen-binding agents that may be used to treat damaged collagen within tissues or used to specifically target therapeutics to tissues containing undamaged or damaged collagen. The tandem collagen binding agents provided herein may allow for tighter binding to collagen by bridging two collagen fibrils. This novel binding interaction of the collagen binding agents described herein will provide novel and unexpected therapeutic uses. The increased binding affinity and cross-linking of collagen molecules may make these tandem collagen binding agents more effective for certain applications than their single binding counterparts. Applications may include skin applications.

In one aspect, collagen-binding agents are provided. The collagen-binding agents may include two collagen-binding domains linked by a domain linker. As used herein, a "collagen-binding domain" refers to a polypeptide that binds collagen. In some embodiments, the collagen-binding domain may bind collagen with a K$_d$ of less than 500 µM, 100 µM, 10 µM, 1 µM, 500 nM, 100 nM, 10 nM, 1 nM, or 0.1 nM. Determination of whether a collagen-binding domain binds collagen can be made, for example, as described in U.S. Patent Publication No. 2010/0129341, which is incorporated herein by reference in its entirety. Briefly, the collagen-binding domain may be incubated with collagen in binding buffer, and the mixture is then filtered through a filter that would otherwise allow the collagen-binding domain to pass through but that blocks the collagen and therefore holds back materials that bind to the collagen. The filtrate is then assayed for the presence of the collagen-binding domain. Suitably, at least 80%, 85%, 90%, 95%, 98% or more suitably at least 99% of the collagen-binding domain is retained by the filter in this assay, as compared to when the filtration is performed without collagen.

Figure 1A:
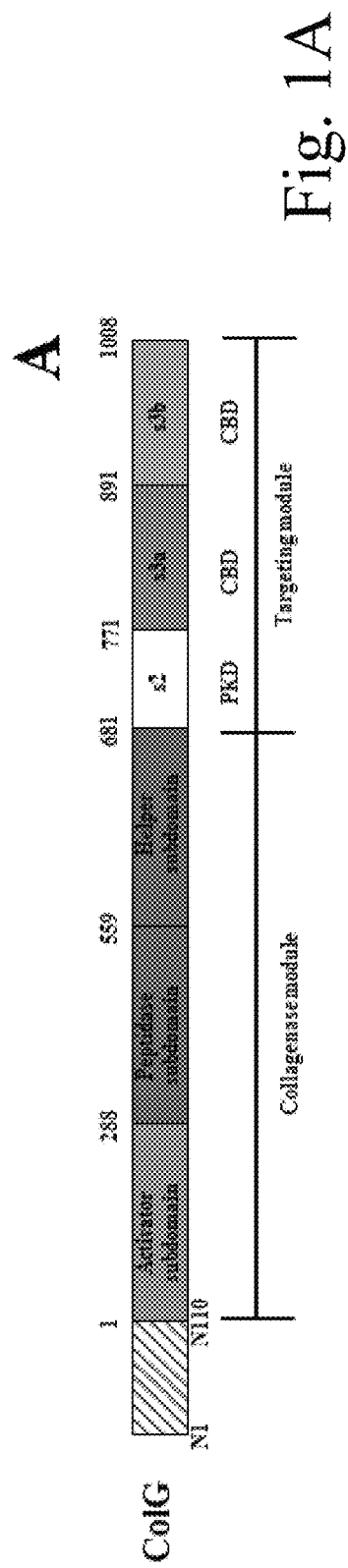
FIG. 1A shows a schematic diagram of the collagenases secreted by C. histolyticum.

The collagen-binding domain may be a bacterial collagen-binding domain. Among other proteins, the collagen-binding domain may be derived from a bacterial ColG protein (Matsushita et al., (1999) J. Bacteriol. 181:923-933) or a bacterial ColH protein (Yoshihara et al., (1994) J. Bacteriol. 176: 6489-6496). As shown in FIG. 1, ColG is a class I collagenase found in various bacterial species including *Clostridium* species. ColH is a class II collagenase also found in various bacterial species including *Clostridium* species. The collagen-binding domain may also be any one of the polypeptides provided in SEQ ID NOS: 1-39, which specify collagen-binding domains from various bacterial species such as *Clostridium* and *Bacillus* species. Those of skill in the art will appreciate that other members of these collagen-binding protein families (i.e, ColG and ColH) may be useful in the compositions and methods described herein.

Suitably, the collagen-binding agents lack collagenase activity. "Collagenase activity" refers to the ability of a polypeptide to degrade or breakdown collagen. For example, as shown in FIG. 1A, ColG and ColH proteins have collagenase modules that include several subdomains that enable these proteins to degrade or breakdown collagen. In some embodiments, the collagen-binding agents lack these or similar collagenase modules.

The collagen-binding agents may include two collagen-binding domains that may be the same type of collagen-binding domain or may be different types of collagen-binding domains. For example, as exemplified in FIG. 1A, bacterial ColG proteins have two types of collagen-binding domains: a s3a collagen-binding domain and a s3b collagen-binding domain. Bacterial ColH proteins have a single collagen-binding domain known as an s3 domain. Thus, the two collagen-binding domains of the presently disclosed collagen-binding agents may be both ColG s3a domains, both ColG s3b domains, both ColH s3 domains, or any combinations thereof. Furthermore, the two collagen-binding domains of the presently disclosed collagen-binding agents may be from the same bacterial species or different species. For example, one of the collagen-binding domains may be a ColG s3a domain from *Clostridium histoliticum* while the other collagen-binding domain may be a ColG s3b domain from *Brevibacillus brevis*.

Figure 5:
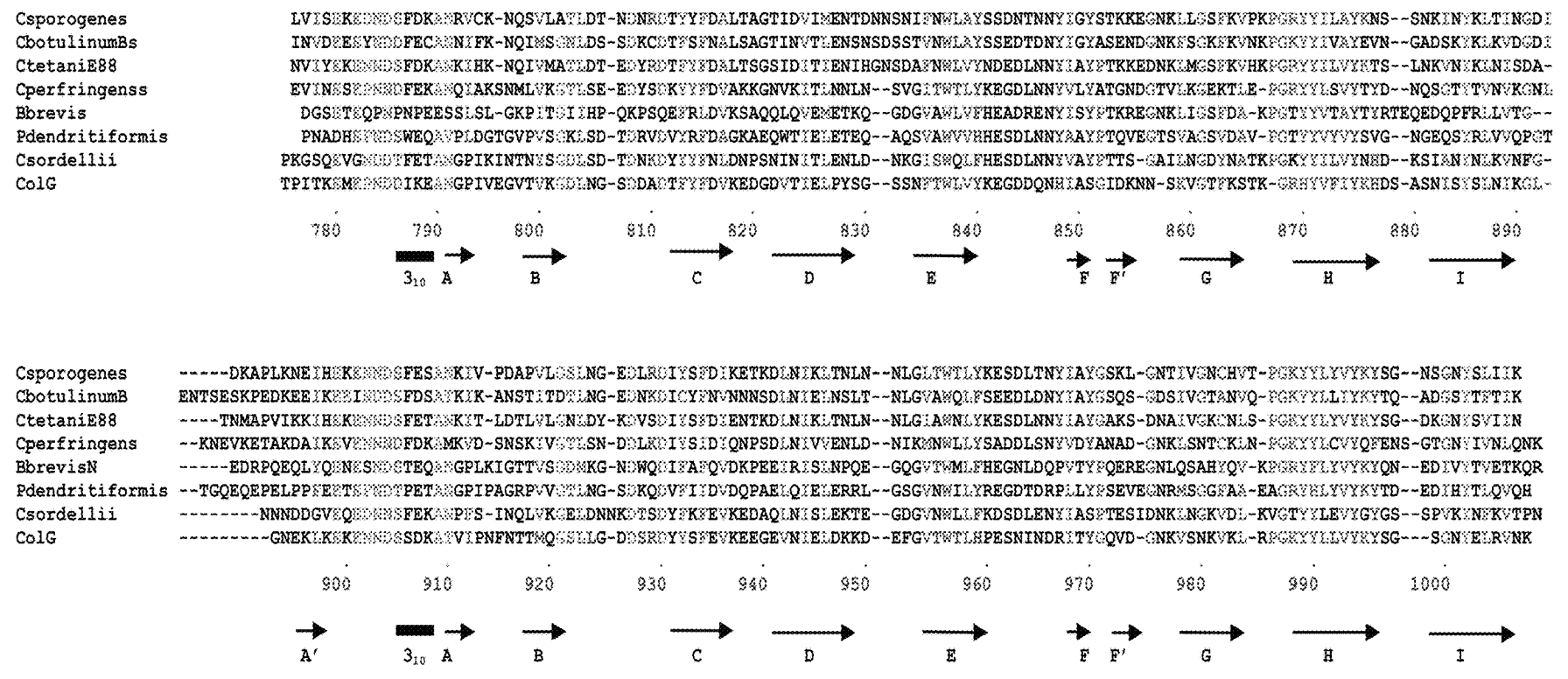
Figure 12:
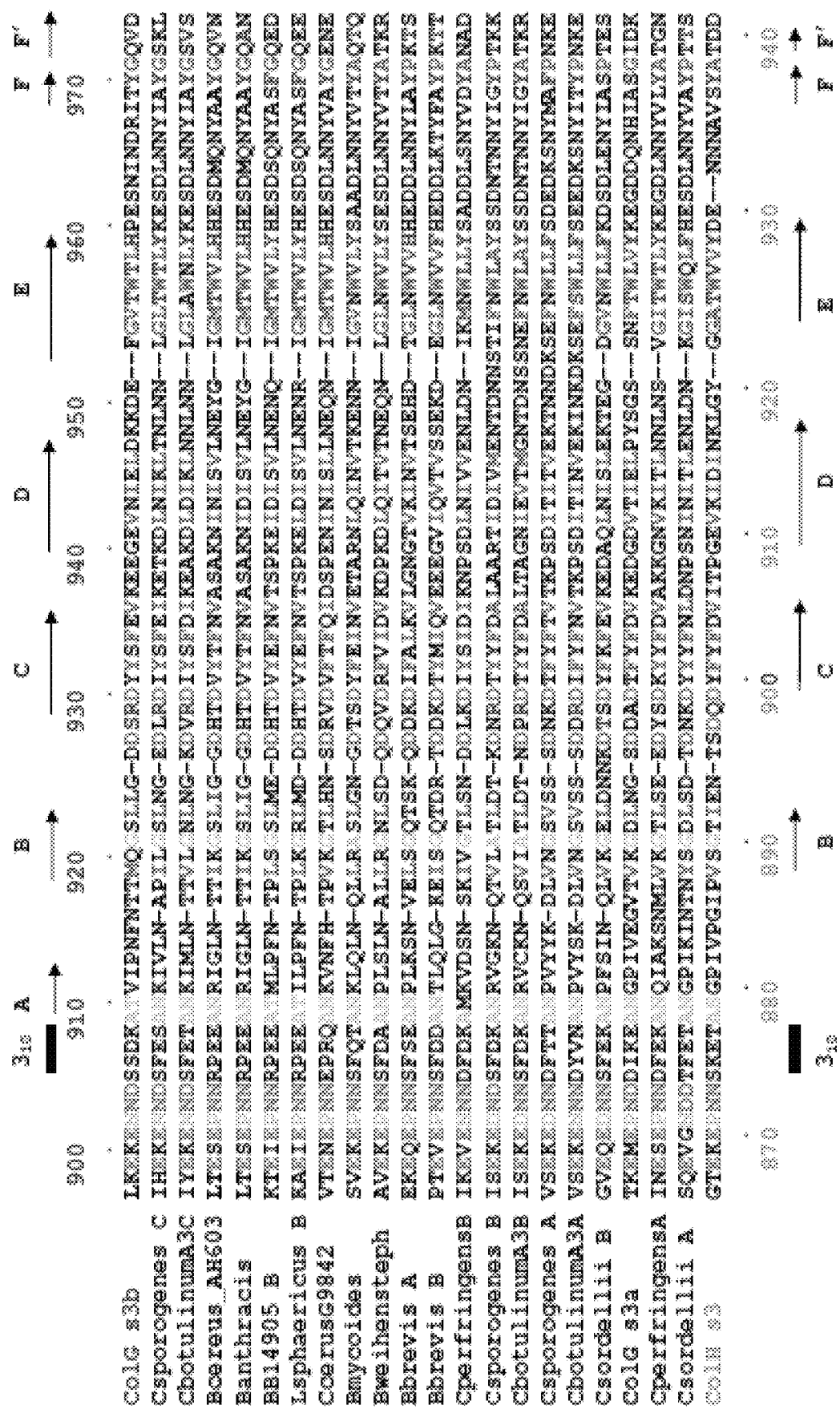
FIG. 12 is a sequence alignment showing the alignment of several M9B bacterial collagenases from the *Bacillus* and *Clostridium* families (See SEQ ID NOs: 1-39). The residues shown in blue are important for collagen binding activity, those shown in green are important for maintaining the architecture or protein folding. Both of these are also underlined for the top and bottom sequences. Residues shown in red are critical for Ca2+ binding and those in orange are critical for positioning the Ca2+ binding residues.

The two collagen-binding domains of the presently disclosed collagen-binding agents may be selected from any one of the polypeptides of SEQ ID NOs: 1-47 or those polypeptides shown in FIGS. 5 and 12. SEQ ID NOs: 1-39 specify individual collagen-binding domains (i.e., ColG s3a, ColG s3b, ColH s3) from ColG and ColH proteins from various bacterial species. SEQ ID NOs: 40-47 specify tandem collagen-binding domains found in ColG proteins from various bacterial species. See, also, FIG. 5.

The collagen-binding domains of the present invention may be variants of the polypeptides of SEQ ID NOs: 1-47. As used herein the term "wild-type" is a term of the art understood by skilled persons and means the typical form of a polypeptide as it occurs in nature as distinguished from "variant" or "mutant" forms. As used herein, a "variant, "mutant," or "derivative" refers to a polypeptide molecule having an amino acid sequence that differs from a reference protein or polypeptide molecule. A variant may have one or more insertions, deletions, or substitutions of an amino acid residue relative to a reference molecule. A variant or mutant may include a fragment of a reference molecule. For example, a collagen-binding domain variant may have one or more insertions, deletions, or substitution of at least one amino acid residue relative to the "wild-type" collagen-binding domain polypeptide. The polypeptide sequences of "wild-type" collagen-binding domains from various bacterial species are presented as SEQ ID NOS: 1-47. These sequences may be used as reference sequences.

A "deletion" in a polypeptide refers to a change in the amino acid sequence resulting in the absence of one or more amino acid residues. A deletion may remove at least 1, 2, 3, 4, 5, 6, 7, 8, 9, 10, 20, 50, 100, or more amino acids residues. A deletion may include an internal deletion and/or a terminal deletion (e.g., an N-terminal truncation, a C-terminal truncation or both of a reference polypeptide).

"Insertions" and "additions" in a polypeptide refer to changes in an amino acid sequence resulting in the addition of one or more amino acid residues. An insertion or addition may refer to 1, 2, 3, 4, 5, 6, 7, 8, 9, 10, 20, 30, 40, 50, 60, 70, 80, 90, 100 or more amino acid residues. A variant of a collagen-binding domain may have N-terminal insertions, C-terminal insertions, internal insertions, or any combination of N-terminal insertions, C-terminal insertions, and internal insertions.

Regarding variant collagen-binding domains and agents, the phrases "% sequence identity," "percent identity," or "% identity" refer to the percentage of residue matches between at least two amino acid sequences aligned using a standardized algorithm. Methods of amino acid sequence alignment are well-known. Some alignment methods take into account conservative amino acid substitutions. Such conservative substitutions, explained in more detail below, generally preserve the charge and hydrophobicity at the site of substitution, thus preserving the structure (and therefore function) of the polypeptide. Percent identity for amino acid sequences may be determined as understood in the art. (See, e.g., U.S. Pat. No. 7,396,664, which is incorporated herein by reference in its entirety). A suite of commonly used and freely available sequence comparison algorithms is provided by the National Center for Biotechnology Information (NCBI) Basic Local Alignment Search Tool (BLAST), which is available from several sources, including the NCBI, Bethesda, Md., at its website. The BLAST software suite includes various sequence analysis programs including "blastp," that is used to align a known amino acid sequence with other amino acids sequences from a variety of databases.

Polypeptide sequence identity may be measured over the length of an entire defined polypeptide sequence, for example, as defined by a particular SEQ ID number, or may be measured over a shorter length, for example, over the length of a fragment taken from a larger, defined polypeptide sequence, for instance, a fragment of at least 15, at least 20, at least 30, at least 40, at least 50, at least 70 or at least 150 contiguous residues. Such lengths are exemplary only, and it is understood that any fragment length supported by the sequences shown herein, in the tables, figures or Sequence Listing, may be used to describe a length over which percentage identity may be measured.

As described herein, variant collagen-binding domains and agents may have at least 50%, 55%, 60%, 65%, 70%, 75%, 80%, 85%, 90%, 95% 98%, or 99% sequence identity to any one of SEQ ID NOs: 1-47.

The polypeptide sequences of the variant collagen-binding domains and agents as contemplated herein may include conservative amino acid substitutions relative to a reference amino acid sequence. For example, variant collagen-binding domains and agents may include conservative amino acid substitutions relative to a reference molecule. "Conservative amino acid substitutions" are those substitutions that are a substitution of an amino acid for a different amino acid where the substitution is predicted to interfere least with the properties of the reference polypeptide. In other words, conservative amino acid substitutions substantially conserve the structure and the function of the reference polypeptide. Conservative amino acid substitutions generally maintain (a) the structure of the polypeptide backbone in the area of the substitution, for example, as a beta sheet or alpha helical conformation, (b) the charge or hydrophobicity of the molecule at the site of the substitution, and/or (c) the bulk of the side chain.

The disclosed variant collagen-binding domains and agents described herein may have one or more functional or biological activities exhibited by a reference polypeptide (e.g., one or more functional or biological activities exhibited by wild-type collagen-binding domains and agents (i.e, SEQ ID NOs: 1-47, See FIGS. 5 and 12). Suitably, the disclosed variant collagen-binding domains and agents retain at least 20%, 40%, 60%, 80%, or 100% of the collagen binding activity of the reference polypeptide (i.e., SEQ ID NOs: 1-47, See FIGS. 5 and 12).

FIG. 5 shows a sequence alignment of several bacterial tandem collagen-binding domains included as SEQ ID NOs: 40-47. As can be seen from the sequence alignment, these proteins have a relatively small amount of sequence identity, but they all are expected to bind to collagen in a similar fashion and are believed to have similar conformations. Thus any of the polypeptides shown in FIG. 5 (i.e., SEQ ID NOs: 40-47) or the collagen-binding domains, variants, or fragments thereof can be used in the compositions and methods described herein. In FIGS. 5 and 12, the amino acid residues important for collagen-binding activity are highlighted in blue. Calcium-binding residues are in red and structurally important residues are shown in green. Based on this alignment it becomes immediately apparent to a person of ordinary skill in the art that various amino acid residues may be altered (i.e. substituted, deleted, etc.) without substantially affecting the collagen-binding activity of the polypeptide. For example, a person of ordinary skill in the art would understand that amino acid residues shown in black likely could be modified without substantially affecting the collagen-binding activity of the polypeptide. A person of ordinary skill in the art would also appreciate that substitutions in a reference collagen-binding domain or agent could be based on alternative amino acid residues that occur at the same position in other collagen-binding domains or agents from other bacterial species. At position 996, for example, the collagen-binding domains shown have either a tyrosine (Y) or phenylalanine (F) residue. Thus, one exemplary modification that is apparent from the sequence alignment in FIG. 5 is a Y996F substitution in a collagen-binding domain or agent. Similar modifications could be made at each position of the sequence alignment shown in FIG. 5.

SEQ ID NOs: 1-39 also include collagen-binding domains that are not shown in FIG. 5, several of these are included in FIG. 12. A person of ordinary skill in the art, however, could easily align these polypeptide sequences with the polypeptide sequences shown in FIGS. 5 and 12 to determine what additional variants could be made to these additional collagen-binding domains. Thus polypeptides having 85%, 88%, 90%, 92%, 94%, 95%, 96%, 97%, 98% or 99% amino acid identity to the collagen-binding polypeptides provided herein. The variant polypeptides are still able to bind collagen.

The collagen-binding domains of the present invention may be full-length versions of SEQ ID NOs: 1-47 or fragments of SEQ ID NOs: 1-47 having at least 8, 16, 32, 64, 100 or more consecutive amino acids of any one of SEQ ID NOs: 1-47. As used herein, a "fragment" is a portion of an amino acid sequence which is identical in sequence to, but shorter in length than, a reference sequence. A fragment may comprise up to the entire length of the reference sequence, minus at least one amino acid residue. In some embodiments, a fragment may comprise at least 8, 10, 15, 20, 25, 30, 40, 50, 60, 70, 80, 90, 100, or more contiguous amino acid residues of a reference polypeptide (i.e., SEQ ID NOs: 1-47). Fragments may be preferentially selected from certain regions of a molecule. The term "at least a fragment" encompasses the full length polypeptide. A fragment of a collagen-binding domain or agent may comprise or consist essentially of a contiguous portion of an amino acid sequence of the full-length collagen-binding domain or agent (i.e., SEQ ID NOs: 1-47). A fragment may include an N-terminal truncation, a C-terminal truncation, or both truncations relative to the full-length collagen-binding domain or agent. The N-terminal and/or C-terminal truncations may include removal of 1, 2, 3, 4, 5, 6, 7, 8, 9, or 10 amino acid residues from a reference polypeptide (i.e., SEQ ID NOs: 1-47).

The collagen-binding domains and agents contemplated herein may be further modified in vitro or in vivo to include non-amino acid moieties. These modifications may include but are not limited to acylation (e.g., O-acylation (esters), N-acylation (amides), S-acylation (thioesters)), acetylation (e.g., the addition of an acetyl group, either at the N-terminus of the protein or at lysine residues), formylation, lipoylation (e.g., attachment of a lipoate, a C8 functional group), myristoylation (e.g., attachment of myristate, a C14 saturated acid), palmitoylation (e.g., attachment of palmitate, a C16 saturated acid), alkylation (e.g., the addition of an alkyl group, such as an methyl at a lysine or arginine residue), isoprenylation or prenylation (e.g., the addition of an isoprenoid group such as farnesol or geranylgeraniol), amidation at C-terminus, glycosylation (e.g., the addition of a glycosyl group to either asparagine, hydroxylysine, serine, or threonine, resulting in a glycoprotein). Distinct from glycation, which is regarded as a nonenzymatic attachment of sugars, polysialylation (e.g., the addition of polysialic acid), glypiation (e.g., glycosylphosphatidylinositol (GPI) anchor formation, hydroxylation, iodination (e.g., of thyroid hormones), and phosphorylation (e.g., the addition of a phosphate group, usually to serine, tyrosine, threonine or histidine) represent other possible modifications.

The two collagen-binding domains may be a ColG or ColH collagen-binding domain from a bacterial species. In some embodiments, the two collagen-binding domains may be any one of the polypeptides of SEQ ID NOs: 1-39, a polypeptide having at least 50%, 55%, 60%, 65%, 70%, 75%, 80%, 85%, 90%, 95% 98%, or 99% sequence identity to any one of SEQ ID NOs: 1-39, or a fragment of at least 8, 10, 15, 20, 25, 30, 40, 50, 60, 70, 80, 90, 100, or more consecutive amino acids of any one of SEQ ID NOs: 1-39.

The two collagen-binding domains may be a bacterial ColG s3b domain and a bacterial ColG s3a domain, s3c domain, or ColH s3 domain. In some embodiments, the one of the collagen-binding domains may be any one of the polypeptides of SEQ ID NOs: 15-30, a polypeptide having at least 50%, 55%, 60%, 65%, 70%, 75%, 80%, 85%, 90%, 95% 98%, or 99% sequence identity to any one of SEQ ID NOs: 15-30, or a fragment of at least 8, 10, 15, 20, 25, 30, 40, 50, 60, 70, 80, 90, 100, or more consecutive amino acids of any one of SEQ ID NOs: 15-30 and wherein the other collagen-binding domain may be any one of the polypeptides of SEQ ID NOs: 1-14 and 31-39, a polypeptide having at least 50%, 55%, 60%, 65%, 70%, 75%, 80%, 85%, 90%, 95% 98%, or 99% sequence identity to any one of SEQ ID NOs: 1-14 and 31-39, or a fragment of at least 8, 10, 15, 20, 25, 30, 40, 50, 60, 70, 80, 90, 100, or more consecutive amino acids of any one of SEQ ID NOs: 1-14 and 31-39.

The two collagen-binding domains may both be a bacterial ColG s3b domain. In some embodiments, the two collagen-binding domains may be any one of the polypeptides of SEQ ID NOs: 15-30, a polypeptide having at least 50%, 55%, 60%, 65%, 70%, 75%, 80%, 85%, 90%, 95% 98%, or 99% sequence identity to any one of SEQ ID NOs: 15-30, or a fragment of at least 8, 10, 15, 20, 25, 30, 40, 50, 60, 70, 80, 90, 100, or more consecutive amino acids of any one of SEQ ID NOs: 15-30.

The two collagen-binding domains may be selected from a bacterial ColG s3a domain, a s3b domain, or a ColH s3 domain. In some embodiments, the two collagen-binding domains may be any one of the polypeptides of SEQ ID NOs: 1-14 and 31-39, a polypeptide having at least 50%, 55%, 60%, 65%, 70%, 75%, 80%, 85%, 90%, 95% 98%, or 99% sequence identity to any one of SEQ ID NOs: 1-14 and 31-39, or a fragment of at least 8, 10, 15, 20, 25, 30, 40, 50, 60, 70, 80, 90, 100, or more consecutive amino acids of any one of SEQ ID NOs: 1-14 and 31-39.

The two collagen-binding domains may be tandem collagen-binding domains from bacterial ColG proteins. In some embodiments, the collagen-binding agent may be any one of the polypeptides of SEQ ID NOs: 40-47, a polypeptide having at least 50%, 55%, 60%, 65%, 70%, 75%, 80%, 85%, 90%, 95% 98%, or 99% sequence identity to any one of SEQ ID NOs: 40-47, or a fragment of at least 8, 10, 15, 20, 25, 30, 40, 50, 60, 70, 80, 90, 100, 150 or more consecutive amino acids of any one of SEQ ID NOs: 40-47.

The collagen-binding agents may include two collagen-binding domains linked by a domain linker. As used herein, a "domain linker" may include a covalent bond and/or a linker or spacer moiety. For instance, the two collagen-binding domains may be linked directly through, e.g., a peptide bond or chemical cross-linking, or indirectly, through, e.g., a linker or spacer polypeptide. Useful domain linkers include polypeptides, amino acids, nucleic acids, as well as homofunctional linkers or heterofunctional linkers. Particularly useful conjugation reagents that can facilitate formation of a covalent bond between the two collagen-binding domains may include a N-hydroxysuccinimide (NHS) ester and/or a maleimide.

A domain linker may also include a spacer polypeptide. The spacer polypeptide may be any length and may include traditional or non-traditional amino acids. For example, the spacer polypeptide may be 1-100 amino acids long, suitably it is at least 2, 3, 5, 10, 15, 20, 25 or more amino acids long such that the two collagen-binding domains of the collagen-binding agent can mediate collagen binding. Spacer polypeptides may include, without limitation, any one of the polypeptides of SEQ ID NOs: 48-55, a GST tag, a His-tag, a Ser linker, or a Gly linker.

In some embodiments, the domain linker may include a tag system. A tag system includes any group of agents capable of binding one another with a high affinity. Several tag systems are well-known in the art and include, without limitation, biotin/avidin, biotin/streptavidin, or digoxigenin (DIG) systems. In some embodiments, said tag system comprises biotin/avidin or biotin/streptavidin.

The domain linker may include any one of the polypeptides of SEQ ID NOs: 48-55 or a polypeptide having at least 50%, 55%, 60%, 65%, 70%, 75%, 80%, 85%, 90%, 95% 98%, or 99% sequence identity to any one of the polypeptides of SEQ ID NOs: 48-55.

The collagen-binding agents of the present invention may further include a therapeutic agent linked to the collagen-binding agent by a therapeutic agent linker. As used herein, a "therapeutic agent" may include any suitable pharmaceutical or other active agent, including, without limitation, osteogenic promoters, antimicrobials, anti-inflammatory agents, polypeptides such as recombinant proteins, cytokines or antibodies, small molecule chemicals, hormones, growth factors, polynucleotides, carbohydrates, lipids, or any combination thereof. Suitably the therapeutic agent(s) are capable of promoting bone growth, decreasing inflammation, promoting collagen stability. Suitably, the therapeutic agent is one whose therapeutic effect is in the region of collagen or damaged collagen. The therapeutic agent may include, without limitation, FGF, parathyroid hormone (PTH), PTH/PTHrP receptor agonist, PTH/PTHrP receptor antagonist, bone morphogenic protein (BMP), G-CSF, FGF, BMP-2, BMP-3, anti-sclerostin antibody, growth hormone, IGF-1, VEGF, TGF-β, KGF, TGF-α, TGF-β1, TGF-β receptor, CT, GH, GM-CSF, EGF, PDGF, celiprolol, activins and connective tissue growth factors. Alternatively, the invention may also aid cell therapy. Cell therapy focuses on the administration of exogenous stem cells. One of the challenges is to deliver these cells at the lesion. Laminin could be attached to CBD. Cells decorated with anchoring collagen binder may seek a lesion and reside at injury site longer to aid in repair. PTH/PTHrP receptor agonists and PTH/PTHrP receptor antagonists have been described in WO 2013/090770, which is incorporated by reference in its entirety. Suitable FGF proteins include, without limitation, bFGF (FGF-2), FGF-4, or FGF-10 (See SEQ ID NO: 56).

The PTH/PTHrP receptor agonist polypeptide segment may be a synthetic polypeptide or a naturally occurring polypeptide. Such polypeptides may be a portion of a polypeptide or may comprise one or more mutations. The mutations may make the PTH/PTHrP receptor agonist a better or worse agonist as compared to the wild-type PTH/PTHrP. Agonist activity with the PTH/PTHrP receptor can be assayed as described in WO2013/090770 and known to those skilled in the art by a cAMP stimulation assay. An agonist will stimulate cAMP synthesis in the assay described. Suitably, an agonist can activate receptor activity at least 10%, 20%, 30%, 40%, 50%, 60%, 70%, 80%, 90%, 100% or even 110% or 120% as much as wild-type PTH (1-34). The PTH/PTHrP receptor agonist polypeptide segment is a PTH or PTHrP polypeptide segment. One human isoform of PTH is SEQ ID NO: 62. One human isoform of PTHrP is SEQ ID NO:57. While the human isoforms are provided, those of skill in the art will appreciate that other non-human-derived isoforms may be used as well. Such non-human-derived isoforms may be able to interact with human PTH/PTHrP receptor and vice versa. The PTH/PTHrP receptor agonist polypeptide segment may be or may include residues 1-33 of SEQ ID NO:62 (residues 1-33 of PTH (SEQ ID NO: 57)). The PTH/PTHrP receptor agonist polypeptide segment may be or may include residues 1-34 of PTH (SEQ ID NO: 62). In other embodiments, it is a fragment of residues 1-34 of PTH (SEQ ID NO: 62). In other embodiments, the PTH/PTHrP receptor agonist polypeptide segment may be or may include residues 1-84 of PTH (SEQ ID NO: 62). In other embodiments, the PTH/PTHrP receptor agonist polypeptide segment may be or may include residues 1-14 of PTH (SEQ ID NO: 62) or residues 1-7 of PTH (SEQ ID NO: 62). The key amino acids for binding to the PTH receptor as an agonist are amino acids 1, 2 and 5 of PTH. In still other embodiments, the PTH/PTHrP receptor agonist is a PTH or PTHrP polypeptide segment for any other species.

The PTH/PTHrP receptor antagonist can include in one embodiment PTH(7-34), i.e., residues 7-34 of PTH (SEQ ID NO: 62). In another embodiment, it is or includes residues 7-33 of PTH (SEQ ID NO: 62). In other embodiments, it is a fragment of residues 7-34 of SEQ ID NO: 57. In another embodiment, the PTH/PTHrP receptor antagonist includes PTH(7-14), i.e., residues 7-14 of PTH (SEQ ID NO: 62). In another embodiment, the PTH/PTHrP receptor antagonists include ((−1)-33) of PTH/PTHrP. In another embodiment, the PTH/PTHrP receptor antagonists include residues 1-14 of PTH with an N-terminal extension. Adding an N-terminal extension to PTH or active N-terminal fragments of PTH converts the PTH peptides to antagonists. The N-terminal extension can be 1, 2, 3, 4, 5, or more amino acids in length. The identity of the amino acids in the N-terminal extension is typically not important. In one embodiment, the PTH/PTHrP receptor antagonist includes residues 1-33 of PTH with a Gly-Ser extension at the N-terminus (SEQ ID NO:58). In another embodiment, the PTH/PTHrP receptor antagonist includes PTHrP(7-34), i.e., residues 7-34 of SEQ ID NO:57, or a fragment of residues 7-34 of SEQ ID NO:57. In another embodiment, the PTH/PTHrP receptor antagonist includes mouse TIP(7-39) (See Hoare S R, Usdin T B. 2002. Specificity and stability of a new PTH1 receptor antagonist, mouse TIP(7-39). Peptides 23:989-98.). Other PTH/PTHrP receptor antagonists that may be used in the fusion proteins are also disclosed in Hoare et al. The PTH/PTHrP receptor antagonist may be a fragment of at least 8, 10, 12 or more amino acids from residues 1-34 of SEQ ID NO:62. In other embodiments the PTH/PTHrP receptor antagonist may be PTH/PTHrP receptor antagonist polypeptide from another species.

In one embodiment, the therapeutic agent or PTH/PTHrP receptor agonist or antagonist polypeptide segment is N terminal to the collagen-binding polypeptide in a fusion protein. That is, the two polypeptide segments each have an N-terminal and a C-terminal, and the N-terminal of the collagen-binding polypeptide is linked directly or indirectly, e.g., through a therapeutic agent linker polypeptide segment (such as PKD, a Glycine or Serine linker) to the C-terminal of the therapeutic agent or PTH/PTHrP agonist or antagonist polypeptide.

A "therapeutic agent linker" may include a covalent bond and/or a linker or spacer moiety. For instance, the collagen-binding agent and the therapeutic agent may be linked directly through, e.g., a peptide bond or chemical cross-linking, or indirectly, through, e.g., a linker or spacer polypeptide. Useful therapeutic agent linkers include polypeptides, amino acids, nucleic acids, as well as homofunctional linkers or heterofunctional linkers. Particularly useful conjugation reagents that can facilitate formation of a covalent bond between the two collagen-binding domains may include a N-hydroxysuccinimide (NHS) ester and/or a maleimide.

A therapeutic agent linker may also include a spacer polypeptide. The spacer polypeptide may be any length and may include traditional or non-traditional amino acids. For example, the spacer polypeptide may be 1-100 amino acids long, suitably it is at least 2, 3, 5, 10, 15, 20, 25 or more amino acids long such that the two collagen-binding domains of the collagen-binding agent can mediate collagen binding. Spacer polypeptides may include, without limitation, a PKD (polycystic kidney disease) domain from a collagenase, a GST tag, a His-tag, a Ser linker, or a Gly linker. In some embodiments, the therapeutic agent linker may include a tag system. A tag system includes any group of agents capable of binding one another with a high affinity. Several tag systems are well-known in the art and include, without limitation, biotin/avidin, biotin/streptavidin, or digoxigenin (DIG) systems. In some embodiments, said tag system comprises biotin/avidin or biotin/streptavidin. The therapeutic agent(s) may be linked to the N-terminus or C-terminus of the collagen-binding agent by the therapeutic agent linker. In embodiments where the therapeutic agent includes a polypeptide, either the C-terminus or N-terminus of the therapeutic agent may be linked to the N-terminus or C-terminus of the collagen-binding agent by the therapeutic agent linker. Furthermore, either the same of different therapeutic agents may be linked to both the N-terminus and C-terminus of the collagen-binding agent by two or more therapeutic agent linkers.

Pharmaceutical compositions including any of the collagen-binding agents described herein are provided. The pharmaceutical compositions may include a pharmaceutical carrier, excipient, or diluent (i.e., agents), which are nontoxic to the cell or animal being exposed thereto at the dosages and concentrations employed. Often a pharmaceutical agent is in an aqueous pH buffered solution. Examples of pharmaceutical carriers include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™ brand surfactant, polyethylene glycol (PEG), and PLURONICS™ surfactant.

Methods of treating a condition are also provided. The methods may include administering any of collagen-binding agents or pharmaceutical compositions described herein to a subject in an amount effective to treat the condition. The "condition" may include a wound (chronic and acute), hyperparathyroidism, a hair condition (either excessive hair growth or hair loss), a collagenopathy, and a bone condition. Bone conditions include fractures, osteoporosis, periodontal defects, or other bone defects. Collagenopathies include, without limitation, osteogenesis imperfecta (OI), Stickler's syndrome, Ehlers-Danlos syndrome, Alport's syndrome, Caffey's disease, and localized collagen or cartilage damage. Many of these diseases are caused by genetic defects that result in the collagen in certain tissues being under twisted or partially untwisted.

Bone loss due to, for example, a collagenopathy such as osteogenesis imperfecta, Stickler's syndrome, osteoporosis or others which put an individual at higher risk for a bone fracture due to a collagen defect could be treated by administration of a collagen-binding agent linked to a bone anabolic peptide. The collagen-binding agent may target the bone anabolic agents to sites where the collagen is malformed and thus may prevent fracture.

Vascular fragility due to defects such as Ehlers-Danlos syndrome type IV, Alport's syndrome or other diseases where blood vessel rupture is more likely due to a defect in collagen formation may be administered collagen-binding agents including peptides that stimulate vascular growth or repair. The collagen binding agents will target the peptide to the areas having collagen damage and these areas are likely to have damaged vessels. The therapeutic agents will stimulate growth and repair at the site of damage and prevent vessel rupture.

Skin fragility due to disorders such as Ehlers-Danlos syndrome, Caffey's disease or other diseases where weakening of the skin due to a collagen defect leads to hyperelasticity, easy bruising or poor wound healing. Dermal and epidermal growth factors may serve as therapeutic agents which when linked to collagen-binding agents and delivered to areas of damaged collagen will stimulate growth and repair of the skin, preventin striae and improving healing.

Also provided herein are methods of treating hyperparathyroidism by administering, for example, collagen-binding agents linked to PTH to a subject in need of treatment for hyperparathyroidism. In one embodiment the PTH administered to the subject may be a PTH from a different species. The effects of PTH agonists and antagonists on hair growth have been studied for over almost 15 years. PTH has a common receptor with PTH-related peptide (PTHrP), which is normally produced by dermal fibroblasts. PTHrP affects keratinocyte proliferation/differentiation and modulates the hair cycle. Most of the testing on hair growth effects has been performed with PTH antagonists, as indications from initial testing were that these were the most effective agents. Both injected and topical formulations have been tested in animal models of chemotherapy-induced alopecia and in the SKH-1 hairless mouse. Part of the effect of PTH antagonists on hair growth is to transition the hair follicles into a dystrophic catagen stage, which protects them from chemotherapeutic damage. However, clinical trials of topical PTH antagonists for chemotherapy-induced alopecia by IGI Pharmaceuticals were discontinued in phase 2 because of limited efficacy. Thus new compositions for treating alopecia are needed.

In another aspect, methods of treating a hair condition (excess hair loss or hair growth) The methods may include administering a collagen-binding agent linked to a PTH/PTHrP receptor agonist to a subject in need of treatment to induce hair growth or stop hair loss. The method is applicable to individuals with alopecia, including chemotherapy induced alopecia, but also alopecia areata, alopecia caused by male pattern baldness, polycystic ovarian syndrome or other hair loss. The compositions may be administered locally or topically to treat hair loss.

In another aspect, methods of slowing hair growth or regrowth after a hair removal procedure by administering a collagen-binding agent linked to a PTH/PTHrP receptor antagonist to a subject are provided. In one embodiment, the collagen-binding agent+PTH antagonist composition is applied locally, topically. The collagen-binding agent+PTH antagonist may be applied after a hair removal procedure to prevent or slow hair regrowth.

The subject of the present invention may be any mammal, suitably a human, domesticated animal such as a dog, cat, horse, cow, pig, or a mouse or rat. Treating the condition or treatment includes but is not limited to ameliorating at least one symptom of the condition, reducing or slowing further progression of the condition, reducing or slowing the spread of the condition to unaffected areas. Treating a subject refers to any type of treatment that imparts a benefit to a subject afflicted with a disease or at risk of developing the disease, including improvement in the condition of the subject (e.g., in one or more symptoms), delay in the progression of the disease, delay the onset of symptoms or slow the progression of symptoms, etc.

An effective amount or a therapeutically effective amount as used herein means the amount of a composition that, when administered to a subject for treating a state, disorder or condition is sufficient to effect a treatment (as defined above). The therapeutically effective amount will vary depending on the compound, formulation or composition, the disease and its severity and the age, weight, physical condition and responsiveness of the subject to be treated.

The compositions (i.e. collagen-binding agents and pharmaceutical compositions) described herein may be administered by any means known to those skilled in the art, including, but not limited to, oral, topical, intranasal, intraperitoneal, parenteral, intravenous, intramuscular, subcutaneous, intrathecal, transcutaneous, nasopharyngeal, intralesional, intra-tumoral, intradermal, or transmucosal absorption. Thus the compositions may be formulated as an ingestable, injectable, topical or suppository formulation. The compositions may also be delivered with in a liposomal or time-release vehicle. Administration of the compositions to a subject in accordance with the invention may exhibit beneficial effects in a dose-dependent manner. Thus, within broad limits, administration of larger quantities of the compositions is expected to achieve increased beneficial biological effects than administration of a smaller amount. Moreover, efficacy is also contemplated at dosages below the level at which toxicity is seen.

It will be appreciated that the specific dosage administered in any given case will be adjusted in accordance with the composition or compositions being administered, the disease to be treated or inhibited, the condition of the subject, and other relevant medical factors that may modify the activity of the compositions or the response of the subject, as is well known by those skilled in the art. For example, the specific dose for a particular subject depends on age, body weight, general state of health, diet, the timing and mode of administration, the rate of excretion, medicaments used in combination and the severity of the particular disorder to which the therapy is applied. Dosages for a given patient can be determined using conventional considerations, e.g., by customary comparison of the differential activities of the compositions described herein and of a known agent, such as by means of an appropriate conventional pharmacological protocol.

The maximal dosage for a subject is the highest dosage that does not cause undesirable or intolerable side effects. The number of variables in regard to an individual treatment regimen is large, and a considerable range of doses is expected. The route of administration will also impact the dosage requirements. It is anticipated that dosages of the compositions will improve the condition being treated by at least 10%, 20%, 30%, 40%, 50%, 60%, 70%, 80%, 90%, 100% or more as compared to no treatment.

The effective dosage amounts described herein refer to total amounts administered, that is, if more than one composition is administered, the effective dosage amounts correspond to the total amount administered. The compositions can be administered as a single dose or as divided doses. For example, the composition may be administered two or more times separated by 4 hours, 6 hours, 8 hours, 12 hours, a day, two days, three days, four days, one week, two weeks, or by three or more weeks.

The collagen-binding agents or pharmaceutical compositions described herein may be administered one time or more than one time to the subject to effectively improve the condition being treated. Suitable dosage ranges are of the order of several hundred micrograms effective ingredient with a range from about 0.01 to 10 mg/kg/day, preferably in the range from about 0.1 to 1 mg/kg/day. Precise amounts of effective ingredient required to be administered depend on the judgment of the practitioner and may be peculiar to each subject. It will be apparent to those of skill in the art that the therapeutically effective amount of the collagen-binding agents and pharmaceutical compositions described herein will depend, inter alia, upon the administration schedule, whether the composition is administered in combination with other therapeutic agents, the status and health of the recipient, and the therapeutic activity of the particular composition.

The present disclosure is not limited to the specific details of construction, arrangement of components, or method steps set forth herein. The compositions and methods disclosed herein are capable of being made, practiced, used, carried out and/or formed in various ways that will be apparent to one of skill in the art in light of the disclosure that follows. The phraseology and terminology used herein is for the purpose of description only and should not be regarded as limiting to the scope of the claims. Ordinal indicators, such as first, second, and third, as used in the description and the claims to refer to various structures or method steps, are not meant to be construed to indicate any specific structures or steps, or any particular order or configuration to such structures or steps. All methods described herein can be performed in any suitable order unless otherwise indicated herein or otherwise clearly contradicted by context. The use of any and all examples, or exemplary language (e.g., "such as") provided herein, is intended merely to facilitate the disclosure and does not imply any limitation on the scope of the disclosure unless otherwise claimed. No language in the specification, and no structures shown in the drawings, should be construed as indicating that any non-claimed element is essential to the practice of the disclosed subject matter. The use herein of the terms "including," "comprising," or "having," and variations thereof, is meant to encompass the elements listed thereafter and equivalents thereof, as well as additional elements. Embodiments recited as "including," "comprising," or "having" certain elements are also contemplated as "consisting essentially of" and "consisting of" those certain elements.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure. Use of the word "about" to describe a particular recited amount or range of amounts is meant to indicate that values very near to the recited amount are included in that amount, such as values that could or naturally would be accounted for due to manufacturing tolerances, instrument and human error in forming measurements, and the like. All percentages referring to amounts are by weight unless indicated otherwise.

No admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinence of any of the documents cited herein. All references cited herein are fully incorporated by reference in their entirety, unless explicitly indicated otherwise. The present disclosure shall control in the event there are any disparities between any definitions and/or description found in the cited references.

Unless otherwise specified or indicated by context, the terms "a", "an", and "the" mean "one or more." For example, "a protein" or "an RNA" should be interpreted to mean "one or more proteins" or "one or more RNAs," respectively.

As used herein, "about," "approximately," "substantially," and "significantly" will be understood by persons of ordinary skill in the art and will vary to some extent on the context in which they are used. If there are uses of these terms which are not clear to persons of ordinary skill in the art given the context in which they are used, "about" and "approximately" will mean plus or minus ≤10% of the particular term and "substantially" and "significantly" will mean plus or minus >10% of the particular term.

The following examples are meant only to be illustrative and are not meant as limitations on the scope of the invention or of the appended claims.

EXAMPLES

Example 1—Activation and Binding Mechanism of Tandem Collagen-Binding Domains with Pseudo-Two Fold-Symmetry

*Clostridium histoliticum* secrets virulence factors, including highly active collagenases CollG (class I) and ColH (class II), to penetrate animal tissues. After the multi-domain ColG utilizes its tandem collagen-binding domain (CBD) to anchor itself onto insoluble collagen, subsequent degradation of the hierarchical substrate involves processive cleavage and rearrangement of fibrils. In this work, the structure of the calcium bound tandem CBD is presented at 1.9 Å resolution ($R_{work}$=15.0%; $R_{free}$=19.6%). The pseudo-two-fold arrangement of CBD would allow ColG to wedge between collagen molecules that are 55 Å apart in order to potentially aid in fibril rearrangement and processive cleavage. Indeed, between 0.1:1 and 0.5:1 molar ratios of tandem CBD and collagen, it accelerated collagen fiber formation. At 1:1 molar ratios and above, the tandem CBD retarded fibril formation. To toggle between collagen molecules, a tighter binding C-side CBD, may initiate binding as demonstrated by small angle X-ray scattering (SAXS) of tandem CBD forming a 1:1 complex with $[(Pro-Hyp-Gly)_{10}]_3$. Subsequently, the weaker binding N-side CBD can latch onto a prone collagen molecule to provide the tightest known fibril binding. The conformational change of the tandem CBD is calcium dependent and cooperative as measured by size exclusion chromatography and by SAXS at pCa in the range of 3-6. At pCa >5, the tandem CBD adopts an extended structure that is easier to be secreted from the bacterium. In the host $pCa^{2+}$>3, the compact structure seen in the crystal structure is adopted. The binding and activation mode described here will help guide site-directed drug delivery vehicle development.

Abbreviations used: CBD, collagen binding domain; MALDI-TOF-MS, matrix-assisted laser desorption/ionization-time of flight mass spectrometry; DLS, dynamic light scattering; SAXS, small angle X-ray scattering.

*Clostridium histolyticum*, which was recently proposed to be reclassified as *Hathewaya histolyticum* based on 16S rRNA gene comparison, produces collagenases that cause extensive tissue damage during myonecrosis (Lawson and Rainey 2015). The most significant of these enzymes, ColG (class I) and ColH (class II), are multi-domain enzymes that include a N-terminal collagenase module (Si), one or two polycystic kidney disease (PKD)-like domains, and one to three C-terminal collagen-binding domains (CBDs) (FIG. 1A), and division of roles in collagenolysis were suggested (Fields 2013).

The C-terminal domains of ColG (s3a, s3b), and ColH (s3), are homologs consisting of approximately 120 amino acids. The domains bind to soluble collagenous peptides and insoluble collagen fibril. Their role in binding to collagen fibril is essential in dismantling its hierarchical structure (Matsushita, Jung et al. 1998, Matsushita, Koide et al. 2001). Truncation of CBD from either full-length ColG or ColH incapacitates their abilities to degrade collagen fibril. Such enzymes can only degrade solubilized collagen or denatured collagen (gelatin). Mutagenesis and collagen-binding studies mapped the binding surface of s3b, while NMR and SAXS studies showed that s3b unidirectionally binds to under-twisted regions of mini-collagen collagen (Philominathan, Koide et al. 2009, Philominathan, Koide et al. 2012). High-speed atomic force microscopy has recently revealed ColG's ability to dismantle collagen in real time (Watanabe-Nakayama, Itami et al. 2016). During degradation, ColG moves processively along collagen fibril from C-terminus to N-terminus to dismantle the fibril. ColG also preferentially targeted less ordered region of collagen fibril. Structural insight for ColG's processsivity and preference for disordered region are described.

Bacterial collagenases require calcium to attain both full catalytic activity and collagen-binding function. The activation of bacterial collagenase involves domain rearrangement triggered by the $Ca^{2+}$ binding to the linker from α-helix to β-sheet (Wilson, Matsushita et al. 2003, Philominathan, Matsushita et al. 2009, Spiriti and van der Vaart 2010, Sides, Liyanage et al. 2012, Bauer, Wilson et al. 2013, Bauer, Janowska et al. 2015). The full-length apo-ColG is expected to be relatively flexible inside the bacteria where $Ca^{2+}$ concentration is low ($0.2$-$0.3\times10^{-6}$ M) allowing the enzyme to be secreted more easily (Wilson, Matsushita et al. 2003). Upon secretion, the linker chelates to $Ca^{2+}$ (~1.2 mM) in the ECM to adopt a rigid structure. Though it has not been shown for ColG, $Ca^{2+}$ chelation indeed triggers a full-length ColH to adopt a less flexible and compact structure as demonstrated using SAXS and limited proteolysis (Ohbayashi, Matsumoto et al. 2013).

The clostridial collagenases have been successfully used for years as a wound debridement. Recently the mixture of ColG and ColH was approved for use in the treatment of excessive connective tissue build up found, for example, in Dupuytren's disease (Gaston, Larsen et al. 2015). Furthermore, the enzymes showed potential to treat different types of connective tissue build ups (Duarte, Correia et al. 2014) and to isolate pancreatic islets for transplantation (McCarthy, Breite et al. 2011). In addition to therapeutic use of full-length collagenase for removal of connective tissue, the non-catalytic segments are used for targeted drug-delivery to reduce dosage and to minimize side effects. Initially, Nishi et al. developed fusion proteins of the targeting segment (s2b-s3) and growth factors. When injected, the fusion proteins remained active at the site of injection for up to 10 days (Nishi, Matsushita et al. 1998). A fusion protein of s3 and parathyroid hormone (PTH-CBD) is being developed to treat osteoporosis (Ponnapakkam, Katikaneni et al. 2011, Ponnapakkam, Katikaneni et al. 2011, Ponnapakkam, Katikaneni et al. 2012), to prevent and to treat alopecia (Katikaneni, Ponnapakkam et al. 2012, Katikaneni, Ponnapakkam et al. 2014, Katikaneni, Ponnapakkam et al. 2014, Katikaneni, Seymour et al. 2015). The systemic application is based on the apparent targeting ability of s3 to blood accessible and regenerating collagen (Stratford, Vu et al. 2014). Although the lower affinity s3 is efficacious as a systemic drug delivery vehicle in vivo, the tighter collagen binder s2b-s3 is more efficacious in wound healing applications when it is applied at the site of injury with collagen-based bone graft material (An, Lin et al. 2015, Fujimaki, Inoue et al. 2015, Saito, Uchida et al. 2015, Uchida, Matsushita et al. 2015). Here we report crystal structures of tandem CBD in the presence of calcium. We also propose its mode of binding and interaction with the collagen substrate and the role of calcium based on gel filtration and SAXS results.

Methods and Materials
Production, Purification, Crystallization and Structure Determination Individual s3a, s3b, as well as tandem CBD derived from the *C. histolyticum* ColG were expressed as glutathione S-transferase (GST)-fusion proteins using method as described previously (Matsushita, Jung et al. 1998). Initial conditions suitable to grow crystals of tandem CBD were identified by high-throughput screen (Hampton Research Crystal Screen HT). Subsequent crystallization trials using the initial conditions were carried out using the hanging-drop method. Crystals of tandem CBD, obtained in the presence of 3 mM calcium (21-26% PEG3350, HEPES pH 7.5 at 37° C.), were orthorhombic (space group, $P2_12_12_1$), with cell parameters a=51.5 Å, b=54.7 Å, c=92.0 Å. The crystals grew within 24 hours in 37° C. but not at 4, 16 and 24° C. The crystals were temperature sensitive and could not withstand cryogenic temperatures. Therefore diffraction data were collected by means of in-house X-ray facility at room temperature to 1.9 Å resolution using a Rigaku 007 generator with Cu Kα radiation. The data sets were processed with d*TREK (Pflugrath 1999) (Table 1). The structure was solved with the molecular replacement program MolRep from the CCP4 package, by using s3b (PDB code 2o8o) as the search model (Murshudov, Vagin et al. 1997). One tandem CBD was found in an asymmetric unit; and therefore, $V_M$ was 2.5 Å³/Da and solvent content was 50% (Matthews 1968). Refinement of the tandem CBD was carried out using Refmac_6.1.13 (Murshudov, Vagin et al. 1997). TLS restraints were applied to main chain atoms with each CBD acting as a TLS group. Babinet scaling was used for bulk solvent refinement. Five percent of the data were set aside to monitor $R_{free}$. The models were manually adjusted between each refinement cycle using MIFit (McRee 1999). Alternate confirmations were built for Lys818, Glu945, Tyr970, and Arg1005. The Ramachandran plot for the final structure obtained with the program Procheck (Laskowski, Macarthur et al. 1993) showed 91% of the residues in the core region and 9% in the additionally allowed region, with none in the generously allowed or disallowed regions. The final refinement statistics are shown in Table 1.

TABLE 1

Data collection statistics

| Data collection statistic | |
|---|---|
| Wavelength (Å) | 1.5419 |
| Temperature (K) | 298 |
| Resolution range (Å)$^a$ | 19.7-1.90 (1.97-1.90) |
| Space group | $P2_1 2_1 2_1$ |
| Unit cell dimension (Å) | |
| a (Å) | 51.5 |
| b (Å) | 54.7 |
| c (Å) | 92.0 |
| Unit cell angle (°) | α, β, γ = 90 |
| Total reflections | 89,473 |
| Redundancy | 4.47 (4.27) |
| Completeness (%)$^a$ | 94.8 (94.2) |
| $R_{meas}$ (%)$^{a,\,b}$ | 7.1 (49.2) |
| I/σI$^b$ | 11.2 (2.9) |
| Refinement statistic | |
| Unique reflections | 18,987 |
| Solvent molecules | 211 |
| $R_{work}$ (%) | 15.0 (25.5) |
| $R_{free}$ (%)$^{b,\,c}$ | 19.6 (26.8) |
| Average B value (Å²) | 37.68 |
| Coordinates ESU based on $R_{free}$ (Å) | 0.13 |
| Root mean square deviations | |
| Bond distance (Å) | 0.011 |
| Bond angles (°) | 1.87 |
| Chiral centers (Å³) | 0.17 |
| Planar groups (Å) | 0.01 |
| B-factor restrains | |
| Main-chain bond (Å²) | 3.81 |
| Main-chain angle (Å²) | 4.72 |
| Side-chain bond (Å²) | 6.84 |
| Long range B-factor (Å²) | 12.3 |
| Ramachandran statistic | |
| Most favored region (%) | 90.9 |
| Allowed region (%) | 9.1 |

$^a R_{meas} = \Sigma_{hkl} \{N_{(hkl)}/N_{(hkl)} - 1\}^{1/2} \Sigma_i |I_{i(hkl)} - \langle I_{(hkl)}\rangle|/\Sigma_{(hkl)}\Sigma_i I_{i(hkl)}$
$^b$Data for highest resolution shell are given in parentheses
$^c$5% of data excluded from refinement Small Angle X-Ray Scattering Suitable buffer conditions for small angle X-ray scattering (SAXS) measurements were identified using discontinuous Native-PAGE. For the pCa analysis the tandem CBD was equilibrated into 10 mM HEPES-Na (pH 7.5), 100 mM NaCl, and 2% glycerol. The pCa was maintained with 0.2 mM total EGTA with $CaCl_2$ added to bring pCa values to 3, 4, 5 and 6. The amount of $Ca^{2+}$ needed to reach a given pCa was determined using MAXCHELATOR (Bers, Patton et al. 2010). For the tandem CBD:$[(POG)_{10}]_3$ complex analysis, the complex was equilibrated into 50 mM HEPES-Na (pH 7.5), 100 mM NaCl, and 2 mM $CaCl_2$. $[(POG)_{10}]_3$ was dissolved in 5 mM acetic acid to a concentration of 7.5 mg/mL and stored at 4° C. for 24 h. The peptide was then mixed with tandem CBD in a 1:2 molar ratio of tandem CBD to mini-collagen. Measurements were completed for three concentration series per sample. For the pCa series, the concentration of tandem CBD used at pCa 4 and 5 and 6 was 1, 3, and 5 mg/mL. At pCa 3, the concentration series used was 2, 4, and 6 mg/mL. For the complexes with $[(POG)_{10}]_3$, the concentration series used was 1, 3, and 5 mg/mL. All SAXS data were collected at 10° C. at the Advanced Light Source at Berkley National Lab (SIBYLS beamline, 12.3.1). All data processing was accomplished using primusqt from the ATAS 2.6.1 software package. For CBD at each pCa, exposure data from the concentration gradient that were not affected by either aggregation or detector saturation were extrapolated to infinite dilution. Determination of the radius of gyration ($R_g$), maximum diameter (D) as well as ab initio shape reconstruction of the extrapolated data was carried out using the dammif function in primusqt. The $\chi$ values calculated at the end of each run indicated the agreement between the calculated scattering curve and the experimental scattering curve. For the pCa series, the x values for each shape ranges between 0.8 And 1.2. For the complex with $([POG]_{10})_3$, the x value is 0.8.

Collagen Fibril Formation

The impact of addition of tandem CBD on self-assembly of collagen molecules was monitored by measuring turbidity as an increase in optical density at 450 nm, at 37° C. On ice, a solution of 2 mg/ml of rat collagen was diluted with 40 mM HEPES buffer pH 7.5, with addition of 300 mM NaCl, 2 mM $CaCl_2$, to final concentration of 0.5 mg/ml (2.4 µM). In the next step collagen binding was added in ratios: 0.1 to 1; 0.2 to 1; 0.3:1; 0.5 to 1; 1 to 1; 2 to 1; 3 to 1; 5 to 1 of molar concentration. The turbidity measurement was taken in 96 well plates with 1-minute intervals with spectrophotometer Filter Max F5 (Molecular Devices). From the turbidity curve the following parameters were estimated $t_{lag}$-time at the end of lag phase, maximum turbidity, and V the maximum fibril growth rate.

Analytical Size Exclusion Chromatography

Size exclusion chromatography was performed at room temperature on a HPLC system equipped with a Superdex 75 column (1×30 cm, Pharmacia) at a flow rate of 0.5 ml/min as described (Wilson, Matsushita et al. 2003). The following proteins were used as molecular mass standards: bovine serum albumin, 67.0 kDa; chicken ovalbumin, 43.0 kDa; and ribonuclease A, 13.7 kDa (Pharmacia). The measurement was carried out in triplicate.

Quantitative Analysis of the Binding to a Collagenous Peptide

Binding of various CBD proteins to a collagenous peptide was measured by surface plasmon resonance using a BIA-CORE apparatus (Biacore, Uppsala, Sweden) with a sensor chip (CMS, Biacore) on which a peptide, Gly-(Pro-Hyp-Gly)$_{12}$, was covalently immobilized as described (Wilson, Matsushita et al. 2003).

Collagen Fibril Binding Assay

Binding affinities for three CBDs, s3a, s3b, and s3as3b, to collagen fiber were analyzed. Initially, 10 mg of porcine skin fiber (Nippi, Inc; Japan) was placed on a 0.2 nm spin column and washed with 50 mM Tris-HCl (pH 7.5), supplemented with of 200 mM NaCl and 5 mM $CaCl_2$. Then, 20 µL of a protein mixtures containing 0.5 mg/mL BSA (internal control), and a varied concentration (between 2.5 and 20 mg/mL) of tandem CBD, equilibrated in the buffer above, was added and thoroughly mixed with the fiber. After a 30 min incubation at room temperature, the supernatant containing unbound tandem CBD was collected and quantified using SDS-PAGE. For this step, an equal volume of unused protein mixture was used as a control. After electrophoresis, proteins were stained with Coomassie Brilliant Blue R-250, and their relative amounts were estimated by ImageJ software (version 1.4.2; National Institutes of Health). Based on these estimations a calibration curve was constructed for each CBD and was used to quantify CBD amounts in each supernatant. The results obtained by triplicate assay were analyzed on a Scatchard plot to obtain the dissociation constant ($K_d$) and the number of binding sites ($B_{max}$) for each CBD.

Results and Discussion

Structure Description of Tandem CBD

Crystal structure of tandem CBD consisting of s3a and s3b was solved at 1.9 Å resolution. Although the s3b segment has been described before, the s3a segment is described for the first time in this paper. Both s3a and s3b adopt a very similar β-sandwich 'jelly-roll' composed of ten β-strands. The CBDs are related by a pseudo two-fold rotational symmetry that is stabilized by salt-bridges and hydrogen-bonding interactions. The pseudo symmetry axis, which is perpendicular to the plane of the page in FIG. 1B, positions the collagen-binding pockets in the tandem CBD to be 55 Å apart. Each domain chelates to two $Ca^{2+}$ i.e., one $Ca^{2+}$ is bound with pentagonal bipyramidal geometry and the other is bound with square antiprismatic geometry as described (Bauer, Wilson et al. 2013). The electron density allowed us to observe a prolyl-cis-peptide bond between Glu792 and Pro793 and non-prolyl-cis-peptide bond between Glu899 and Asn992. Overlay based on 110 equivalent $C_\alpha$ atoms shows that the s3a and s3b share r.m.s.d. of 0.9 Å and only significantly deviate at loops (r.m.s.d of 1.1-2.5 Å). Loops in both CBDs exhibited the highest B-factor values, while β-sheet residues exhibited low B-factor values. As expected, B-factor values for residues that interact with $Ca^{2+}$ were amongst the lowest. The average temperature factor for s3a is lower than s3b due to crystal packing. In the previously reported structure of holo-s3b (PDB code 4HPK), the protease sensitive and highly dynamic loop 960-968 was not observed (Philominathan, Koide et al. 2009, Sides, Liyanage et al. 2012. Bauer, Wilson et al. 2013). In the structure presented here, the dynamics of this loop are suppressed by crystal packing contacts. Otherwise the s3b alone and s3b in the tandem CBD are virtually identical to each other ($C_\alpha$ r.m.s.d. 0.6 Å).

$Ca^{2+}$-Induced Transformation of the Tandem CBD

Figure 2A:
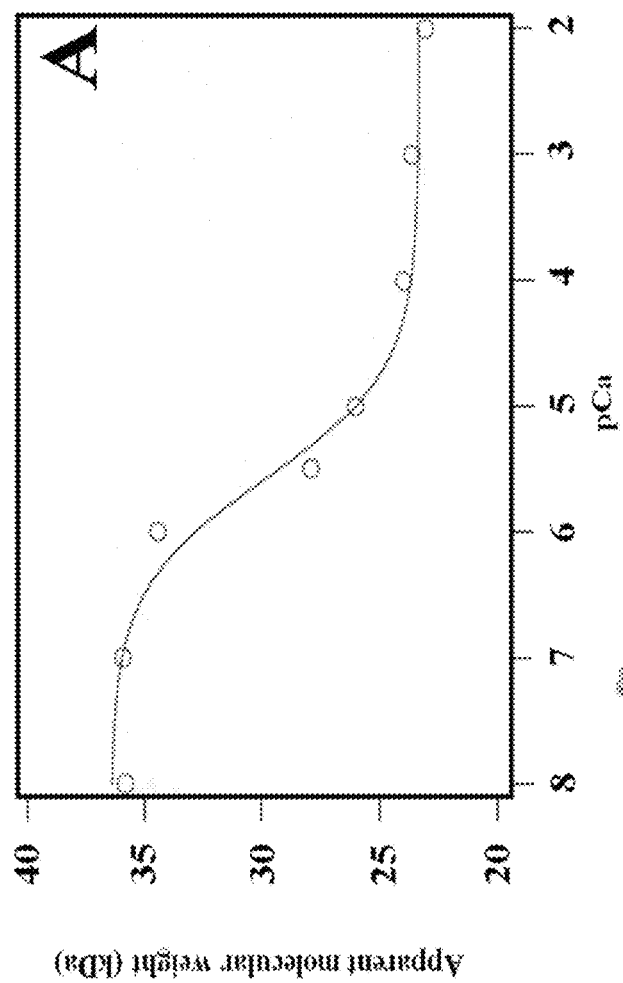
FIG. 2A shows the apparent molecular weights of the tandem CBD as a function of pCa determined by analytical size exclusion chromatography.
Figure 2B:
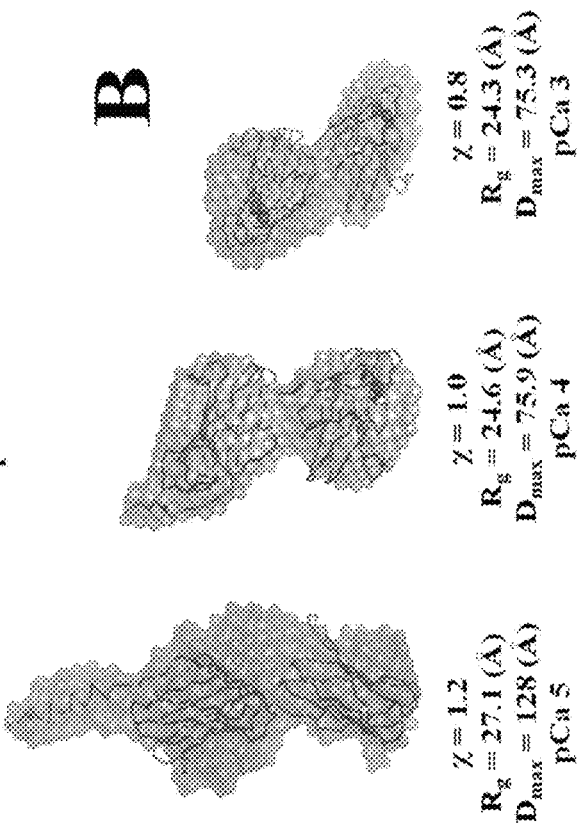
FIG. 2B shows molecular envelopes of the tandem CBD at pCa 3, 4, and 5 based on SAXS scattering profiles.

The difference in $Ca^{2+}$ concentration inside bacterium and ECM in host could be taken advantage of to efficiently secrete bacterial collagenases into the host. The intracellular $Ca^{2+}$ concentration of *Clostridium* is likely to be similar to that of *Escherichia coli* (0.2-0.3×10$^{-6}$M) (Holland, Jones et al. 1999), which is well below the tandem CBD's apparent $K_d$ for $Ca^{2+}$ (FIG. 2A). However, extracellular tissue fluids contain $Ca^{2+}$ concentrations at ~1.2 mM (Maurer and Hohenester, 1997). Monitored by size exclusion chromatography, the domain reorientation of s3a-s3b is a cooperative event induced by $Ca^{2+}$, and SAXS data corroborated the magnitude of the structural change (FIG. 2B). The SAXS derived envelope for tandem CBD at pCa less than or equal to 5 (10 µM) adopts a rod like shape (FIG. 2B). A bump in the envelope resembles how α-helical linker appeared in SAXS (Sides, Liyanage et al. 2012). At pCa=6, the β-strand A' of s3b also unfolds to greatly increase the linker's dynamic (Sides, Liyanage et al. 2012). Upon increasing $Ca^{2+}$ concentrations, the tandem CBD steadily adopts more compact shapes (FIG. 2B). At pCa=4 (100 µM) the shape resembles the crystal structure with the exception of a bulge that suggests the linker of s3a remained dynamic. At pCa=3 (1 mM) it agrees well with the crystal structure of tandem CBD. The domain rearrangement modeled in the SAXS derived envelope is consistent with the observations made for s3b with its 12-residue-long linker. The linker between s3a and s3b has been shown to undergo secondary structure transformation from α-helix to β-sheet that is induced by $Ca^{2+}$ binding and results in tighter contact between the domains (Wilson, Matsushita et al. 2003, Sides, Liyanage et al. 2012). The β-strand A' of s3b also unfolds to greatly increase the linker's dynamic (Sides, Liyanage et al. 2012). Free energy simulations have determined that the calcium ions not only stabilize the cis-peptide bond thermodynamically but also catalyze its formation (Spiriti and van der Vaart 2010). Calcium dependent structural change was monitored for full length ColH by size exclusion chromatography and by SAXS (Ohbayashi, Matsumoto et al. 2013). Expanding upon the findings for tandem CBD, the full length ColG and ColH is also likely to undergo $Ca^{2+}$-induced domain rearrangement. Dynamic ColG and ColH inside bacterium should allow for rapid secretion inducing maximum damage to host.

Mini Collagen-Tandem CBD Interaction

Our results suggest a unique interaction between tandem CBD and either collagen fibril or mini-collagen. Collagen fibril is built by a staggered array of triple-helical tropocollagen, and is insoluble in water. Meanwhile, synthetic collagenous peptide, or mini-collagen, which mimics the structure of native tropocollagen and is soluble in water, has been used to investigate the individual collagen-protein interactions. Use of mini-collagen also allows quantitative analysis of CBD-collagen interaction. The $K_d$ values have been evaluated for various forms of CBDs to insoluble collagen fibril and to mini-collagen, and they come to a good agreement (Matsushita, Koide et al. 2001). Tandem CBD binds to the collagen fibril the tightest ($K_d$~) among CBDs tested and much tighter than the sum of s3a or s3b alone ($K_d$~100 μM). However, tandem CBD binds to mini-collagen only as tightly as s3b does. Tandem CBD did show cooperative binding when the immobilized mini-collagen density was high. SAXS results of tandem CBD:mini-collagen also revealed a 1:1 complex. Given the binding affinities of s3a and s3b to mini-collagen, s3b segment of tandem CBD bound unidirectionally to the C-terminus of $[(POG)_{10}]_3$ (Philominathan, Koide et al. 2009, Philominathan, Koide et al. 2012, Bauer, Wilson et al. 2013), thus it was modeled in the envelope as such (FIG. 2B).

The s3a binds less tightly than s3b to collagen possibly because it is missing one of the conserved tyrosine residues. When CBD sequences were aligned, three Tyr residues (970, 994 and 996 in s3b) are well conserved, and mutagenesis of any of these residues diminished binding to mini-collagen (Wilson, Matsushita et al. 2003). When the sequences of tandem CBDs were aligned instead difference in N-side CBD and C-side CBD emerged. The equivalent to Tyr 996 in the N-side CBD was not well conserved, but all three Tyr residues were well conserved in the C-side CBD (FIG. 2B; FIG. 5). The s3a also lacks conserved Tyr970 equivalent and Ser851 occupies the position instead. Neighboring His848 of s3a does occupy approximately the same space near this residue and could, to a lesser extent, fulfill its role. The gene duplication of CBD apparently required a loss of functionally importance at position 877 in order to prevent the domain form becoming stuck at the surface of the fibril. The CBD domains are positioned by an extra 0-strand (β-strand A') and interdomain interactions. While β-strand A' is present in both s3a and s3b, it is absent in s3, and hence, could be unique to collagenases with multiple CBDs. The extra 0-strand is stabilized by unconserved side-chain interactions, which suggests that gene duplication was a relatively recent event.

The observed 1:1 complex of CBD to mini-collagen indicates that the tighter binding sib initiates binding. This proposed mechanism is supported by the observation that the tandem CBD binds to mini-collagen just as tightly as s3b alone. Nevertheless, the tandem CBD binds tighter to collagen fibril than s3b alone (Toyoshima, Matsushita et al. 2001). While s3b initiates binding and serves the central role, s3a plays an auxiliary, yet pivotal role in intercalating into a space created between collagen molecules that are 55 Å apart. Although it was suggested that CBDs could lie side by side to bind to one tropocollagen molecule (Eckhard and Brandstetter 2011), our structure suggests this mode is less likely.

ColH, unlike ColG, possesses two PKD-like domains (s2a and s2b) but only a single CBD, s3. Though not a collagen-binder by itself, s2b does enhance s3's affinity to collagen (Matsushita, Jung et al. 1998). While s3a is a collagen-binder, it may work similarly to s2b by serving as the source of weak interactions that allows the segment to scan a single tropocollagen for opportunistic binding sites as well as contribute to an overall tighter collagen-binder. Development of the tandem PKD and tandem CBD segments allowed ColG and ColH to potentially seek different niches in collagen fiber.

Collagen Fibril-Tandem CBD Interaction

Figure 1B:
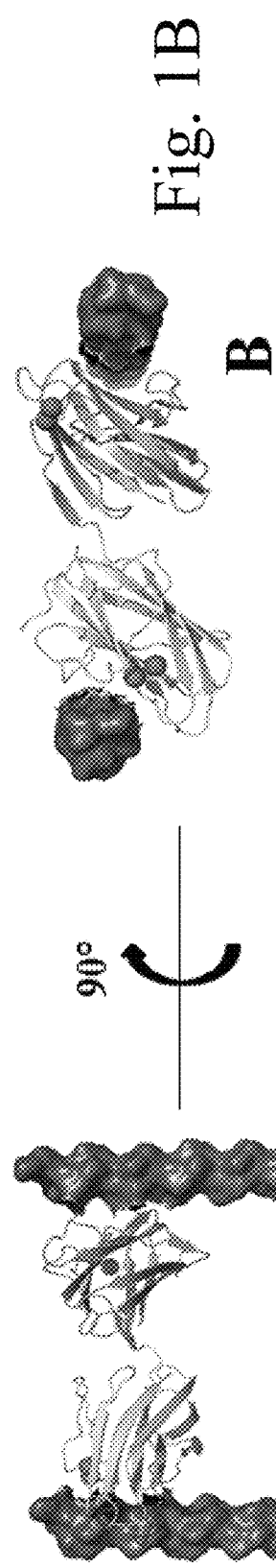
FIG. 1B shows pseudo-twofold symmetry in the structure of the tandem collagen-binding domain.
Figure 1C:
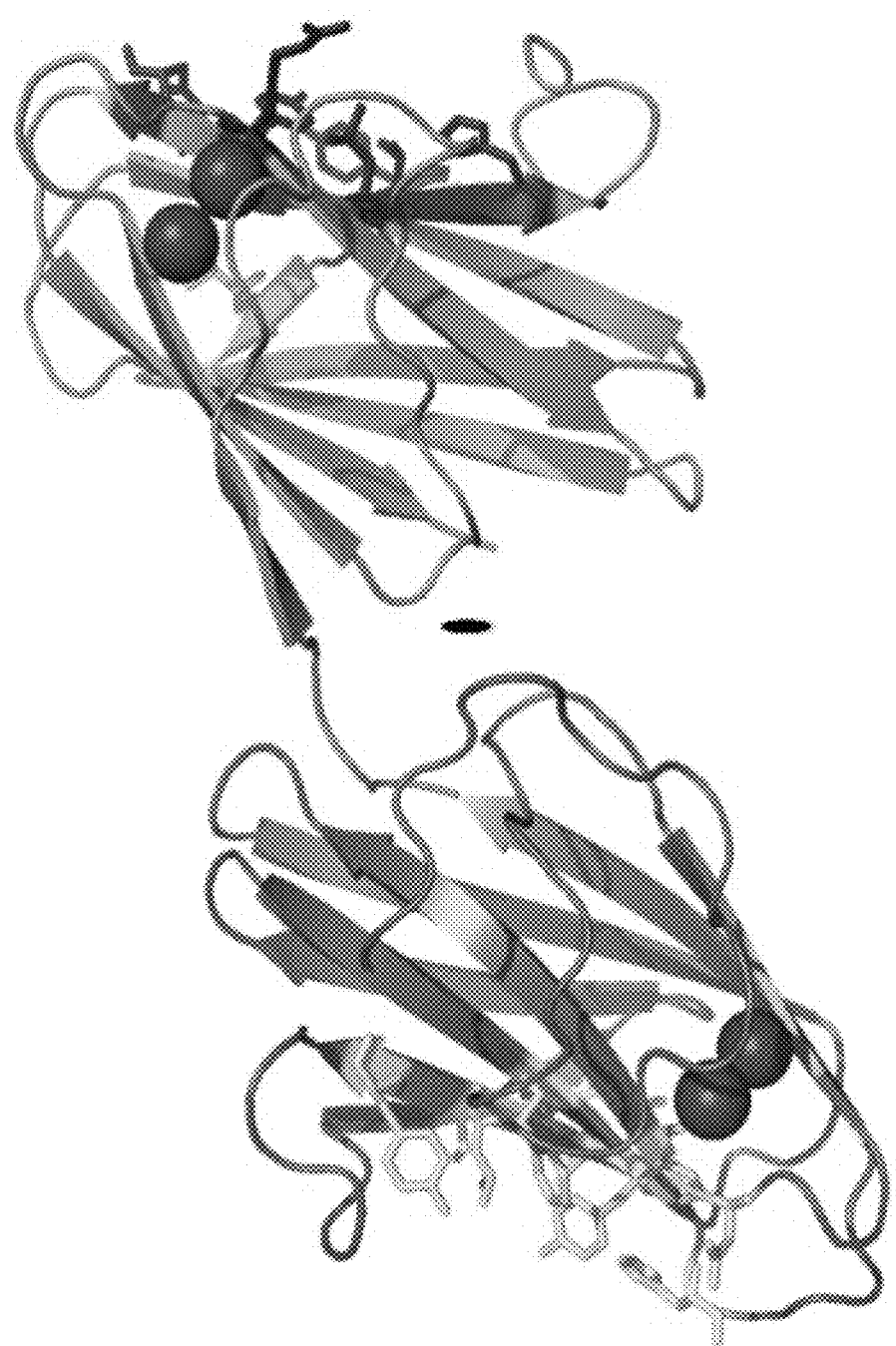
FIG. 1C shows the two-fold axis is perpendicular to the plane of the page. The key residues for binding to collagen are highlighted: yellow for ColGS3a, blue for ColGS3b.

The pseudo-two fold symmetry orients the collagen-binding surface at the opposite ends of the molecule and allows the tandem CBD to bind to parallelly oriented two collagen molecules (FIG. 1B). Collagen self assembles to form collagen fibril in a process that can be monitored by change in absorbance at 450 nm. Collagen-binding molecules, such as s3b, bind to collagen and retard fibril formation (Okano-Kosugi, Matsushita et al. 2009). However, since the tandem CBD appears to be able to wedge itself between two collagen molecules, we tested its ability to promote fibril self-assembly. To investigate the influence tandem CBD has on collagen fibril formation, the turbidity of mixtures of tandem CBD and collagen was monitored (FIG. 3). Remarkably, the ratio of tandem CBD to collagen has contrasting influences on the lag time prior to fiber formation. In the absence of tandem CBD (control), the lag time for fibril formation is 19 min and is consistent with previous observations (Okano-Kosugi, Matsushita et al. 2009). At a 0.1:1 ratio of tandem CBD to collagen, the lag time is reduced to 15 min. When the concentration of tandem CBD is relatively high compared to the ratio of collagen the lag time increases. At a tandem CBD to collagen ratio of 5:1, the lag time is 31 min. The fibril growth for lower ratios of CBD resulted in a much higher absorption of 0.0217 compared to samples with higher ratios of tandem CBD, where the absorption was 0.005. Influence on lag time inversely correlated to collagen fibril thickness. The 0.1:1 and 0.2:1 mixtures of tandem CBD to collagen resulted in fibril that is about 14% thicker than the collagen fibril control. At a 5:1 ratio, the thickness is 2% less than the control. At low concentrations, tandem CBD aids in collagen alignment, and thus accelerates the formation of nuclei for collagen self-assembly. The seemingly opposite effects of this two ratio ranges of CBD to collagen on self-assembly may provide an important clue to understanding how ColG disassemble and breakdown collagen fibril as recently being revealed (Watanabe-Nakayama. Itami et al. 2016).

Collagenolysis by ColG

Hydrolysis of collagen fibril by ColG monitored in real time by high-speed atomic force microscopy revealed as following: (1) the interactions of inter-fibril collagen molecules prevented collagenase molecules from engaging; (2) collagen molecules were rearranged onto other fibrils when subjected to ColG; (3) disordered D-periodicity made the collagen fibril susceptible to degradation by ColG; (4) ColG moves from C-terminus to N-terminus processively; (5) At every pass, ColG evenly trimmed the thickness of the collage fibril. The structure of tandem CBD sheds some light into the ColG's action.

Figure 4A:
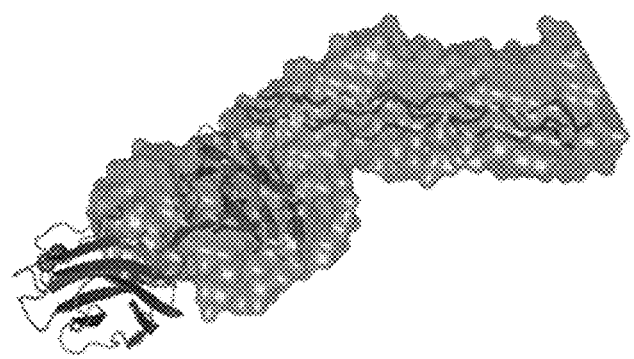
FIG. 4A shows the molecular envelopes of the tandem CBD to mini-collagen based on SAXS scattering profiles.
Figure 4B:
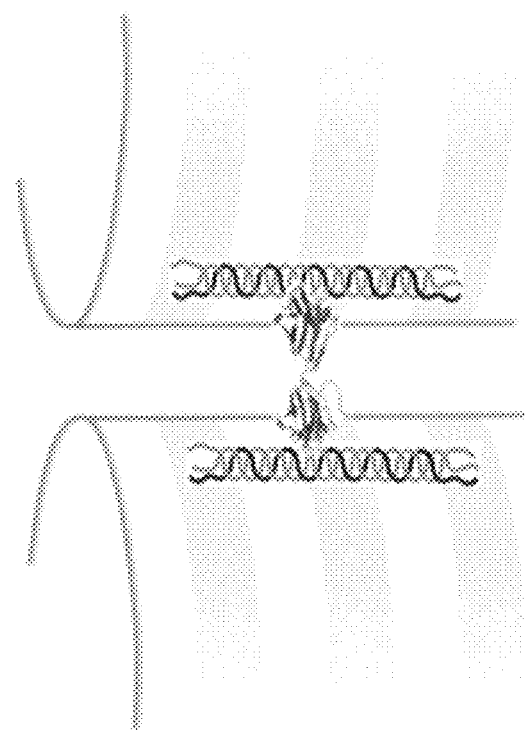
FIGS. 4B and 4C show models of the binding of tandem collagen-binding domain to collagen fibril.
Figure 4C:
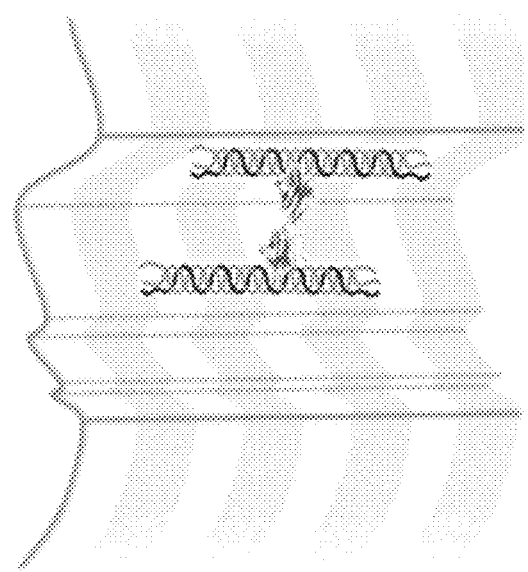

Given the binding clefts' positions on opposite faces of the domain, we propose the following collagen-binding modes: (i) tandem CBD wedges into interfibrous space (FIG. 4B), (ii) tandem CBD wedges into crevices found in damaged or remodeling collagen fiber (FIG. 4C). The effort necessary to toggle into interfibrous space may appear as though ColG was stalled. The tandem CBD's ability to facilitate fibril formation could explain how ColG rearranged collagen fibrils. Mechanically disrupting D-periodicity in collagen fibril may introduce pockets for ColG binding. If the fibril is damaged by removing the outermost tropocollagen, the CBD could wedge itself between the exposed tropocollagen. Such action raises the interesting possibility that the tandem CBD could be used to target drugs to damaged collagen. Alternatively, the tandem CBD could toggle between two fibrils. The median of the surface-to-surface distance of one fibril to another is ~3.2 nm in skin (Kuwaba, Kobayashi et al. 2001). Nearly 15% of the interfibrous space in skin should be in the order of ~6 nm. The results suggest that the tandem CBD could be useful to anchor drugs to damaged tissues. Once toggled between collagen molecules, ColG's processive C→N-terminal movement is likely driven by the collagenase module, and thus, evenly trimmed collagen fibril is produced (Eckhard and Brandstetter 2011, Eckhard, Schonauer et al. 2011).

The high-resolution structure of bacterial tandem collagen binding domain is reported for the first time. The pseudo-symmetrical arrangement of CBD, resulting from gene duplication and fusion, could allow it to recognize unique niche in collagen fibril to facilitate degradation of collagen. The structure of tandem CBD reveals that it could wedge between parallelly oriented collagen molecules. The structure combined with previously identified CBD preference for under-twisted regions of collagen suggest the tandem CBD targets ColG to damaged regions of the collagen fibril. Such targeting also opens new drug targeting avenues in which the tandem CBD tightly anchors drugs to the injury site.

REFERENCES FOR EXAMPLE 1

An, B., Y. S. Lin and B. Brodsky (2015). "Collagen interactions: Drug design and delivery." *Adv Drug Deliv Rev.*

Bauer, R., K. Janowska, K. Taylor, B. Jordan, S. Gann, T. Janowski, E. C. Latimer, O. Matsushita and J. Sakon (2015). "Structures of three polycystic kidney disease-like domains from *Clostridium histolyticum* collagenases ColG and ColH." *Acta Crystallogr D Biol Crystallogr* 71(Pt 3): 565-577.

Bauer, R., J. J. Wilson, S. T. L. Philominathan, D. Davis, O. Matsushita and J. Sakon (2013). "Structural Comparison of ColH and ColG Collagen-Binding Domains from *Clostridium histolyticum*." *Journal of Bacteriology* 195 (2): 318-327.

Bers, D. M., C. W. Patton and R. Nuccitelli (2010). "A Practical Guide to the Preparation of Ca2+ a Buffers." *Calcium in Living Cells* 99: 1-26.

Duarte, A. S., A. Correia and A. C. Esteves (2014). "Bacterial collagenases—A review." *Crit Rev Microbiol.*

Eckhard, U. and H. Brandstetter (2011). "Polycystic kidney disease-like domains of clostridial collagenases and their role in collagen recruitment." *Biol Chem* 392(11): 1039-1045.

Eckhard, U., E. Schonauer, D. Nuss and H. Brandstetter (2011). "Structure of collagenase G reveals a chew-and-digest mechanism of bacterial collagenolysis." *Nat Struct Mol Biol* 18(10): 1109-1114.

Fields, G. B. (2013). "Interstitial collagen catabolism." *J Biol Chem* 288(13): 8785-8793. Fujimaki, H., G. Inoue, K. Uchida, M. Miyagi, W. Saito, A. Sato and M. Takaso (2015). "Elevation of Microglial Basic Fibroblast Growth Factor Contributes to Development of Neuropathic Pain after Spinal Nerve Ligation in Rats." *Spine (Phila Pa. 1976).*

Gaston, R. G., S. E. Larsen, G. M. Pess, S. Coleman, B. Dean, B. M. Cohen, G. J. Kaufman, J. P. Tursi and L. C. Hurst (2015). "The Efficacy and Safety of Concurrent Collagenase *Clostridium Histolyticum* Injections for 2 Dupuytren Contractures in the Same Hand: A Prospective, Multicenter Study." *J Hand Surg Am* 40(10): 1963-1971.

Holland, I. B., H. E. Jones, A. K. Campbell and A. Jacq (1999). "An assessment of the role of intracellular free Ca2+ in *E. coli.*" *Biochimie* 81(8-9): 901-907.

Katikaneni, R., T. Ponnapakkam, O. Matsushita, J. Sakon and R. Gensure (2014). "Treatment and prevention of chemotherapy-induced alopecia with PTH-CBD, a collagen-targeted parathyroid hormone analog, in a non-depilated mouse model." *Anticancer Drugs* 25(1): 30-38.

Katikaneni, R., T. Ponnapakkam, A. Seymour, J. Sakon and R. Gensure (2014). "Parathyroid hormone linked to a collagen binding domain promotes hair growth in a mouse model of chemotherapy-induced alopecia in a dose-dependent manner." *Anticancer Drugs* 25(7): 819-825.

Katikaneni, R., T. Ponnapakkam, H. Suda, S. Miyata, J. Sakon, O. Matsushita and R. C. Gensure (2012). "Treatment for chemotherapy-induced alopecia in mice using parathyroid hormone agonists and antagonists linked to a collagen binding domain." *Int J Cancer* 131(5): E813-821.

Katikaneni, R., A. W. Seymour, R. Gulati, T. Ponnapakkam and R. C. Gensure (2015). "Therapy for Alopecia Areata in Mice by Stimulating the Hair Cycle with Parathyroid Hormone Agonists Linked to a Collagen-Binding Domain." *J Investig Dermatol Symp Proc* 17(2): 13-15.

Kuwaba, K., M. Kobayashi, Y. Nomura, S. Irie and Y. Koyama (2001). "Elongated dermatan sulphate in postinflammatory healing skin distributes among collagen fibrils separated by enlarged interfibrillar gaps." *Biochem J* 358(Pt 1): 157-163.

Laskowski, R. A., M. W. Macarthur, D. S. Moss and J. M. Thornton (1993). "Procheck—a Program to Check the Stereochemical Quality of Protein Structures." *Journal of Applied Crystallography* 26: 283-291.

Lawson, P. A. and F. A. Rainey (2015). "Proposal to restrict the genus *Clostridium* (Prazmowski) to *Clostridium butyricum* and related species." *Int J Syst Evol Microbiol.*

Matsushita, O., C. M. Jung, J. Minami, S. Katayama, N. Nishi and A. Okabe (1998). "A study of the collagen-binding domain of a 116-kDa *Clostridium histolyticum* collagenase." *J Biol Chem* 273(6): 3643-3648.

Matsushita, O., T. Koide, R. Kobayashi, K. Nagata and A. Okabe (2001). "Substrate recognition by the collagen-binding domain of *Clostridium histolyticum* class I collagenase." *J Biol Chem* 276(12): 8761-8770.

Matthews, B. W. (1968). "Solvent content of protein crystals." *J Mol Biol* 33(2): 491-497. McCarthy, R. C., A. G. Breite, M. L. Green and F. E. Dwulet (2011). "Tissue dissociation enzymes for isolating human islets for transplantation: factors to consider in setting enzyme acceptance criteria." *Transplantation* 91(2): 137-145.

McRee, D. E. (1999). "XtalView/Xfit—A versatile program for manipulating atomic coordinates and electron density." *J Struct Biol* 125(2-3): 156-165.

Murshudov, G. N., A. A. Vagin and E. J. Dodson (1997). "Refinement of macromolecular structures by the maximum-likelihood method." *Acta Crystallogr D Biol Crystallogr* 53(Pt 3): 240-255.

Nishi, N., O. Matsushita, K. Yuube, H. Miyanaka, A. Okabe and F. Wada (1998). "Collagen-binding growth factors: production and characterization of functional fusion proteins having a collagen-binding domain." *Proc Natl Acad Sci USA* 95(12): 7018-7023.

Ohbayashi, N., T. Matsumoto, H. Shima, M. Goto, K. Watanabe, A. Yamano, Y. Katoh, K. Igarashi, Y. Yamagata and K. Murayama (2013). "Solution structure of clostridial collagenase h and its calcium-dependent global conformation change." *Biophys J* 104(7): 1538-1545.

Okano-Kosugi, H., O. Matsushita, S. Asada, A. B. Herr, K. Kitagawa and T. Koide (2009). "Development of a high-throughput screening system for the compounds that inhibit collagen-protein interactions." *Anal Biochem* 394(1): 125-131.

Pflugrath, J. W. (1999). "The finer things in X-ray diffraction data collection." *Acta Crystallogr D Biol Crystallogr* 55(Pt 10): 1718-1725.

Philominathan, S. T., O. Matsushita, R. Gensure and J. Sakon (2009). "Ca2+-induced linker transformation leads to a compact and rigid collagen-binding domain of *Clostridium histolyticum* collagenase." *FEBS J* 276(13): 3589-3601.

Philominathan, S. T. L., T. Koide, K. Hamada, H. Yasui, S. Seifert, O. Matsushita and J. Sakon (2009). "Unidirectional Binding of Clostridial Collagenase to Triple Helical Substrates." *Journal of Biological Chemistry* 284(16): 10868-10876.

Philominathan, S. T. L., T. Koide, O. Matsushita and J. Sakon (2012). "Bacterial collagen-binding domain targets undertwisted regions of collagen." *Protein Science* 21(10): 1554-1565.

Ponnapakkam, T., R. Katikaneni, E. Miller, A. Ponnapakkam, S. Hirofumi, S. Miyata, L. J. Suva, J. Sakon, O. Matsushita and R. C. Gensure (2011). "Monthly administration of a novel PTH-collagen binding domain fusion protein is anabolic in mice." *Calcif Tissue Int* 88(6): 511-520.

Ponnapakkam, T., R. Katikaneni, T. Nichols, G. Tobin, J. Sakon, O. Matsushita and R. C. Gensure (2011). "Prevention of chemotherapy-induced osteoporosis by cyclophosphamide with a long-acting form of parathyroid hormone." *J Endocrinol Invest* 34(11): e392-397.

Ponnapakkam, T., R. Katikaneni, H. Suda, S. Miyata, O. Matsushita, J. Sakon and R. C. Gensure (2012). "A single injection of the anabolic bone agent, parathyroid hormone-collagen binding domain (PTH-CBD), results in sustained increases in bone mineral density for up to 12 months in normal female mice." *Calcif Tissue Int* 91(3): 196-203.

Saito, W., K. Uchida, O. Matsushita, G. Inoue, H. Sekiguchi, J. Aikawa, H. Fujimaki and M. Takaso (2015). "Acceleration of callus formation during fracture healing using basic fibroblast growth factor-kidney disease domain-collagen-binding domain fusion protein combined with allogenic demineralized bone powder." *J Orthop Surg Res* 10: 59.

Sides, C. R., R. Liyanage, J. O. Lay, S. T. L. Philominathan, O. Matsushita and J. Sakon (2012). "Probing the 3-D Structure, Dynamics, and Stability of Bacterial Collagenase Collagen Binding Domain (apo-versus holo-) by Limited Proteolysis MALDI-TOF MS." *Journal of the American Society for Mass Spectrometry* 23(3): 505-519.

Spiriti, J. and A. van der Vaart (2010). "Mechanism of the calcium-induced trans-cis isomerization of a non-prolyl peptide bond in *Clostridium histolyticum* collagenase." *Biochemistry* 49(25): 5314-5320.

Stratford, R., Jr., C. Vu, J. Sakon, R. Katikaneni, R. Gensure and T. Ponnapakkam (2014). "Pharmacokinetics in rats of a long-acting human parathyroid hormone-collagen binding domain peptide construct." *J Pharm Sci* 103(2): 768-775.

Toyoshima, T., O. Matsushita, J. Minami, N. Nishi, A. Okabe and T. Itano (2001). "Collagen-binding domain of a *Clostridium histolyticum* collagenase exhibits a broad substrate spectrum both in vitro and in vivo." *Connect Tissue Res* 42(4): 281-290.

Uchida, K., O. Matsushita, N. Nishi, G. Inoue, K. Horikawa and M. Takaso (2015). "Enhancement of periosteal bone formation by basic fibroblast-derived growth factor containing polycystic kidney disease and collagen-binding domains from *Clostridium histolyticum* collagenase." *J Tissue Eng Regen Med.*

Watanabe-Nakayama, T., M. Itami, N. Kodera, T. Ando and H. Konno (2016). "High-speed atomic force microscopy reveals strongly polarized movement of clostridial collagenase along collagen fibrils." *Sci Rep* 6: 28975.

Wilson, J. J., O. Matsushita, A. Okabe and J. Sakon (2003). "A bacterial collagen-binding domain with novel calcium-binding motif controls domain orientation." *Embo Journal* 22(8): 1743-1752.

Example 2—Acceleration of Bone Formation During Fracture Healing by Basic Fibroblast Growth Factor Fused with Tandem Collagen-Binding Domains from *Clostridium histolyticum* Class I Collagenase The increased retention of recombinant basic fibroblast growth factor (bFGF) at fracture sites accelerates bone formation during fracture healing. We previously constructed a fusion protein consisting of bFGF and a polycystic kidney disease domain (PKD; s2b) and a collagen-binding domain (CBD; s3) derived from the *Clostridium histolyticum* class II collagenase (ColH); and reported the combination of the fusion protein and a collagen-like peptide, poly(Pro-Hyp-Gly)$_{10}$ (SEQ ID NO: 59), induced mesenchymal cell proliferation and callus formation at fracture sites. It is known that *C. histolyticum* also produces class I collagenase (ColG), which possesses tandem CBDs (s3a and s3b) at the C-terminus. First, we examined binding affinity of the four collagen anchors derived from two clostridial collagenases to a collagenous peptide, H-Gly-Pro-Arg-Gly-(Pro-Hyp-Gly)$_{12}$-NH$_2$ (SEQ ID NO: 60), by surface plasmon resonance, which revealed that the tandem CBDs (s3a-s3b) shows the highest affinity to a collagenous peptide. Then, we constructed fusion proteins consisting of bFGF and single CBD (bFGF-s3b) or tandem CBDs (bFGF-s3a-s3b) to compare their biological abilities to those of the previous fusion construct (bFGF-s2b-s3). A fracture-model study showed that bFGF-s3a-s3b exhibit the highest abilities to induce mesenchimal cell proliferation and bone formation. Taken together, collagen anchors with higher collagen-binding affinity exert bFGF to show higher biological activities. The poly(Pro-Hyp-Gly)$_{10}$/bFGF-(CBD)$_2$ composite therefore appears to have the potential to promote bone fracture healing in the clinical setting.

Basic fibroblast growth factor (bFGF) is a mitogenic protein with angiogenic properties and is involved in bone remodeling during early bone repair [1;2]. Recombinant human bFGF has demonstrated efficacy in animal models of osteoporosis for regenerating bone fractures and defects [3;4]. In two recent clinical trials, bFGF treatment accelerated bone union at osteotomy and tibial fracture sites [5;6]. Although the findings from these studies strongly indicate that bFGF promotes bone remodeling and regeneration, exogenously added bFGF is rapidly diffused from bone defect sites.

*Clostridium histolyticum*, a pathogenic bacterium of gas gangrene, secretes two classes of collagenase, (class I, ColG and class II, ColH). These enzymes commonly contain a catalytic domain (s1), polycystic kidney disease domain (PKD, s2; SEQ ID NO: 61), and collagen-binding domain (CBD, s3). However copy numbers of PKD and CBD in the C-terminal collagen-anchors are different in ColG and ColH, being s2-s3a-s3b and s2a-s2b-s3 respectively [7;8]. We previously demonstrated that fusion proteins consisting of bFGF and either CBD (bFGF-s3) or PKD-CBD (bFGF-s2b-s3) derived from ColH accelerated bone formation in rat femurs when loaded onto collagen sheets compared to native bFGF [9]. When combined with high-density collagen sheets, bFGF-s2b-s3 promoted greater bone formation than bFGF-s3[10]. The combination of bFGF-s2b-s3 with the collagen-like peptide poly(Pro-Hyp-Gly)$_{10}$ (SEQ ID NO: 59) also induced greater bone formation compared to bFGF alone in mice bone fracture models[11]. In a more recent study, a fusion protein consisting of galectin-9 and tandem CBDs (s3a and s3b) derived from ColG displayed higher collagen-binding activity than the corresponding protein fused with PKD and CBD (s2b and s3) derived from ColH [12]. Based on these findings, we speculated that a bFGF fusion protein containing tandem CBDs from ColG would increase the retention of bFGF at the fracture site through the enhancement of collagen-binding activity, leading to improved bone formation and fracture repair.

Here, we evaluated dissociation constants between various collangen-anchors and mini-collagen in vitro. Following the results, we constructed fusion proteins consisting of bFGF and either single (bFGF-s3b) or tandem CBD(s) (bFGF-s3a-s3b) derived from ColG, and examined the bone formation ability of these fusion proteins with previously constructed two fusion proteins consisting of bFGF and collagen-anchors derived from ColH.

Materials and Methods

A Mini-Collagen Peptide and a Collagen-Like Polypeptide

Figure 11:
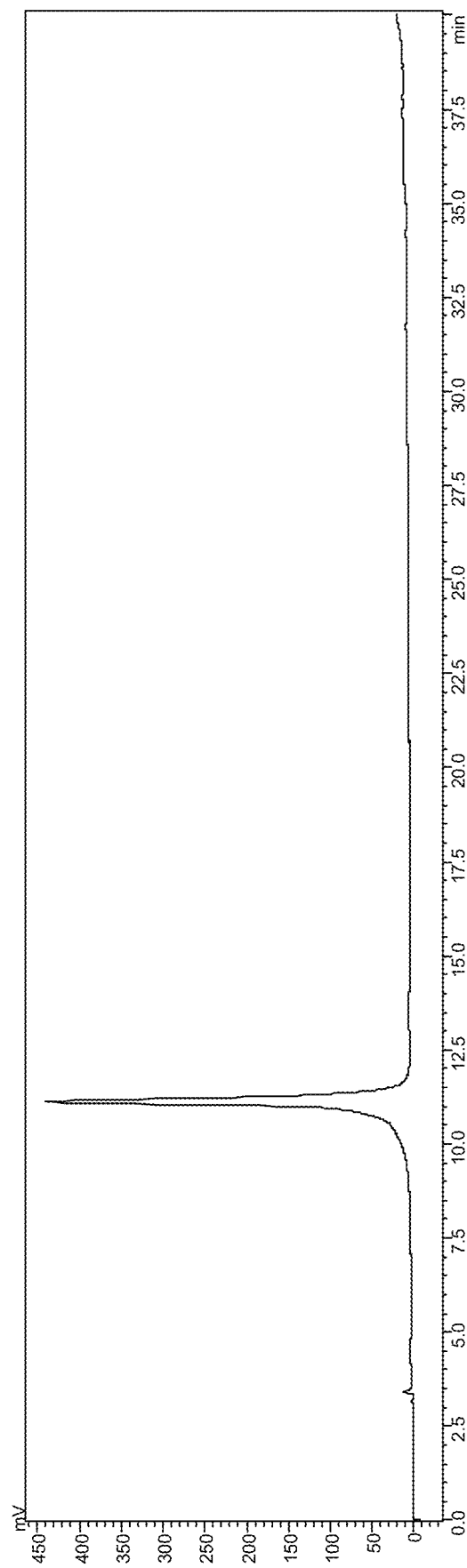
FIG. 11 shows an HPLC profile of H-Gly-Pro-Arg-Gly-(Pro-Hyp-Gly)$_{12}$-NH$_2$ (SEQ ID NO: 60). HPLC gradient: 10-40% CH$_3$CN in 0.05% TFA over 30 min at 60° C.

A mini-collagen peptide, H-Gly-Pro-Arg-Gly-(Pro-Hyp-Gly)$_{12}$-NH$_2$ (SEQ ID NO: 60), was synthesized by a N-(9-fluorenyl) methoxycarbonyl (Fmoc)-based strategy on Rink amide resins (Novabiochem, San Diego, Calif.). In each cycle, Fmoc-amino acids (5 equivalents; Novabiochem) were reacted in the presence of N,N'-diisopropylcarbodiimide (5 equivalents; Wako Pure Chemical, Osaka, Japan) and 1-hydroxybenzotriazole (5 equivalents; Wako Pure Chemical) in N,N-dimethylformamide for 90 min. Fmoc deprotection was performed by 20% (v/v) piperidine in DMF for 20 min. Peptide cleavage and deprotection steps were performed by treatment with a standard trifluoroacetic acid (TFA) scavenger cocktail (TFA: m-cresol:thioanisole:water: ethanedithiol: 82.5:5:5:5:2.5, v/v) for 4 hours at room temperature. The peptides were purified by HPLC on a Cosmosil 5C18-AR-II column (20×250 mm, Nacalai Tesque, Kyoto, Japan) with CH$_3$CN in water, both containing 0.05% (v/v) TFA. Purity of the product was confirmed by RP-HPLC on a Cosmosil 5C18-AR-II (4.6×250 mm, Nacalai Tesque) with a linear gradient of CH$_3$CN in water, both containing 0.05% (v/v) TFA. Mass spectrometric analysis was performed with a Bruker Autoflex III MALDI-TOF MS (Bruker Daltonics, Leipzig, Germany). H-Gly-Pro-Arg-Gly-(Pro-Hyp-Gly)$_{12}$-NH$_2$ (SEQ ID NO: 60): MS (MALDI-TOF) m/z calcd. for C$_{159}$H$_{232}$N$_{44}$O$_{52}$ ([M+H]$^+$): 3590.7 found 3590.6. A HPLC profile of H-Gly-Pro-Arg-Gly-(Pro-Hyp-Gly)$_{12}$-NH$_2$ (SEQ ID NO: 60) is shown in FIG. 11. A collagen-like polypeptide, poly(Pro-Hyp-Gly)$_{10}$ (SEQ ID NO: 59) was obtained from PHG Co., Ltd. (Hyogo, Japan) [13].

Collagen-Anchors Derived from Clostridial Collangenases, ColG and ColH

CBD (s3) and PKD-CBD (s2b-s3) derived from the *C. histolyticum* class II collagenase ColH were purified as described previously[14]. CBD (s3b) and CBD-CBD (s3a-s3b) derived from the *C. histolyticum* class I collagenase ColG were purified as described previously[17].

Quantitative Analysis of Collagen Anchor Binding to a Collagenous Peptide

Binding of collagen-anchors to the mini-collagen peptide was measured by surface plasmon resonance using a BIACORE apparatus (Biacore, Uppsala, Sweden) in the same manner as reported previously [15]. Briefly, the peptide was dissolved in 10 mM sodium acetate (pH 6.0) at a concentration of 0.1 mg/ml, and was covalently immobilized on a CM5 sensor chip (Biacore) using the standard amine coupling procedure recommended by the manufacturer. Resonance was measured in 10 mM sodium HEPES (pH 7.4), 150 mM NaCl, 1 mM CaCl$_2$, and 0.005% Tween-20 at a flow rate of 20 µl/min at 25° C. After each binding step, the chip was regenerated with a 180-s pulse of 0.1 M HCl. Values for the apparent dissociation constant, K$_D$(app), were calculated from equilibrium binding data for eight protein concentrations (100 nM-300 µM) by direct fitting to the following equation by the least squares method, $$cRU = cRU_{max} \times [protein]/(K_D + [protein]) \qquad (Eq.\ 1)$$

where cRU is the response at equilibrium corrected for bulk refractive index errors using a sham-coupled flow cell blocked with ethanolamine, [protein] is the analyte concentration, and K$_D$ is the dissociation constant.

Collagen-Binding bFGF

Figure 6:
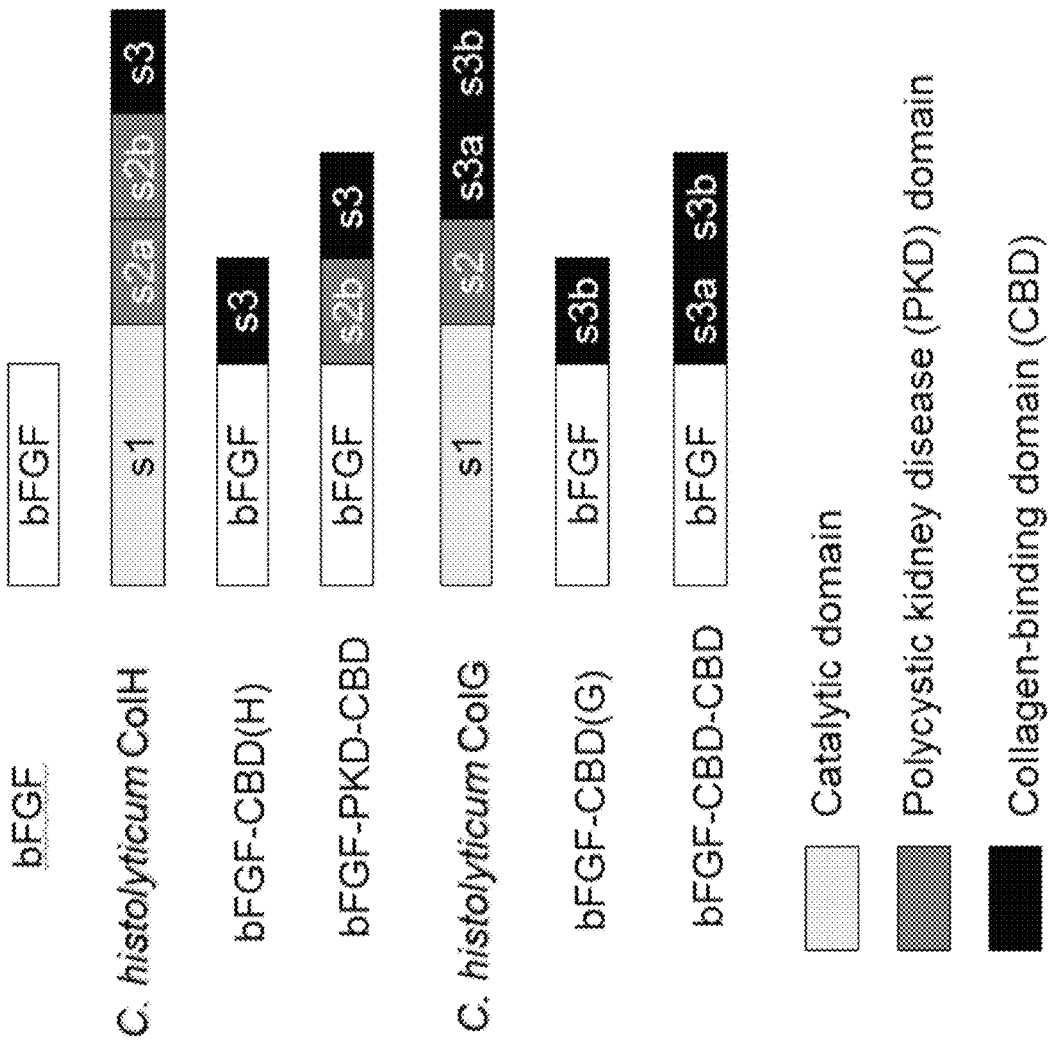
FIG. 6 shows a scheme for the preparation of the four collagen binding-basic fibroblast growth factor constructs used in Example 2.

Four collagen-binding bFGF fusion proteins (CB-bFGFs) were used in this study (FIG. 6). Two fusion proteins, bFGF-s3 and bFGF-s2b-s3, consisting of human bFGF, and CBD or PKD-CBD derived from ColH were prepared as previously described [10]. In order to prepare bFGF-s3b (ColG), an expression plasmid, pCHG115 DNA encoding a fusion protein between GST and a C-terminal collagen-binding domain (s3b, ColG) was digested with BamHI and EcoRI at the linker region, and ligated with a hbFGF-encoding DNA fragment pretreated with BglII and EcoRI. *Escherichia coli* DH5a was transformed with the ligation mixture. to confirm the nucleotide sequence of resultant plasmid (pCHG115-hbFGF) by Sanger sequencing. *E. coli* BL21 CodonPlus RIL (Agilent Technologies, Santa Clara, Calif.) was transformed with the plasmid to express the GST-bFGF-s3b fusion protein. The fusion protein was purified, and the GST moiety was cleaved off as described previously [10]. Another fusion protein consisting of bFGF and tandem CBDs derived from ColG (bFGF-s3a-s3b) was produced in the same manner using another expression plasmid, pCHG112.

Proliferation Assay

Periosteum was collected from the distal femurs of 10-week-old Wistar rats as previously described [9], and was then digested with 0.2% type I collagenase (Wako Pure Chemical Industries, Ltd., Tokyo, Japan) for 2 h at 37° C. The digested sample was passed through a 40-µm filter to obtain single-cell suspensions of nucleated cells, which were then seeded at $1 \times 10^4$ cells/cm$^2$ in 6-well culture plates containing α-minimum essential medium (α-MEM) supplemented with 10% fetal bovine serum, 100 U/ml penicillin, and 100 µg/ml streptomycin. The plates were incubated at 37° C. for 7 days in a 5% $CO_2$ atmosphere and the passage 0 (P0) cells were then detached from the plate surface by treatment with 0.25% trypsin and 1 mM EDTA for 5 min. The cells were collected and seeded at $1.25 \times 10^3$ cells/well in 96-well plates. α-MEM containing either bFGF, bFGF-s3 (ColH), bFGF-s2b-s3 (ColH), bFGF-s3b (ColG), or bFGF-s3a-s3b (ColG) was then added to the culture supernatant at concentrations of 0 (control), 0.1, 1, and 10 pM. Cell proliferation was evaluated after 2 days of treatment using a water-soluble tetrazolium (WST) assay kit (Cell Count Reagent SF; Nacalai Tesque, Kyoto, Japan) following the manufacturer's protocol and a previously described procedure [9].

Fracture Model

A femur fracture model was generated using 9-week-old C57BL/6J mice. The mice were fed standard rodent chow (CRF-1; Oriental Yeast, Tokyo, Japan), and were housed under controlled environmental conditions (temperature, 23±2° C.; humidity, 55±10%; lighting, 12-h light/dark cycle) in a semi-barrier system at Nippon Charles River Laboratories (Kanagawa, Japan). Femur fractures were generated by first making a 4-mm medial parapatellar incision in the left knee under sterile conditions. After drilling a 0.5-mm hole in the intracondylar notch, a 0.2-mm tungsten guide wire was inserted retrograde into the intramedullary canal, and a section of the femur was removed using a wire saw (0.22 mm in diameter) with a lateral approach. To stabilize the fracture, a stainless steel screw (0.5 mm in diameter) was inserted into the intramedullary canal after removing the guide wire. After generating the fracture, PBS (control), poly(Pro-Hyp-Gly)$_{10}$ (SEQ ID NO: 59) gel containing 0.058 nmoles of bFGF, bFGF-s3, bFGF-s2b-S3, bFGF-s3b, or bFGF-s3a-s3b was immediately injected into the fracture site (n=8, each treatment). The dose of bFGF was determined based on the results of a previous study [11]. All animal procedures followed the guidelines of the Animal Ethics Committee of Kitasato University.

Quantification of New Bone Volume and Bone Mineral Content

To quantify the new bone volume and bone mineral content in the control and treated region, femurs were removed from sacrificed mice four weeks after the fracture treatment, and stored in 4% paraformaldehyde for 48 h at 4° C. The femurs were transferred to PBS and imaged using an inspeXio SMX-90CT microfocus X-ray CT system (Shimadzu, Tokyo, Japan) with the following settings: acceleration voltage, 90 kV; current, 110 mA; voxel size, 20 lm/pixel; and matrix size, 1024×1024. New bone volume and bone mineral content were quantified in the micro-CT images of whole femurs using Tri-3D-Bon three-dimensional (3D) image analysis software (Ratoc System Engineering, Tokyo, Japan) at 10-mm regions of interest (500 slices) of the midfemur, as previously described [14;16]. Bone mineral content was estimated by comparing the measured densities of each femur sample in the micro-CT images to those in a hydroxyapatite (HA) calibration curve, which was constructed by plotting the data generated from phantom images prepared with 200, 300, 400, 500, 600, 700, and 800 mg HA/cm$^3$. New bone was defined as having a threshold density value of ≥300 mg/cm$^3$.

Histological Evaluation

To examine the effects of poly(Pro-Hyp-Gly)$_{10}$/bFGF-53a-s3b (ColG) treatment on bone formation, femurs were excised from control and treated animals 14 days after the creation of fractures. The femur samples were demineralized in a 20% EDTA solution for 28 days, and the remaining tissue was then embedded in paraffin. The femurs were sectioned (3 µm) through the long axis in the coronal plane, and the obtained sections were stained with hematoxylin and eosin (HE) for morphological analysis.

Statistical Analysis

Differences among the PBS (control), bFGF, bFGF-s3, bFGF-s2b-s3, bFGF-s3b and bFGF-s3a-s3b groups were examined using one-way ANOVA with Fisher's least significant difference (LSD) test. The level of significance was set at $p<0.05$. All statistical analyses were conducted using SPSS software (Version 19.0; SPSS Inc., Chicago, Ill.).

Results

Binding Affinity of Collagen-Anchors

Dissociation constants of four collagen-anchors to the mini-collagen peptide, H-Gly-Pro-Arg-Gly-(Pro-Hyp-Gly)$_{12}$-NH$_2$ (SEQ ID NO: 60), were measured by surface plasmon resonance (Table 2). Although s2b-s3 (PKD-CBD, ColH) showed a lower Kd value compared to the s3 alone (CBD, ColH), the values of s3b (CBD, ColG) and s3a-s3b (CBD-CBD, ColG) were spprox. 10-fold lower than those of the ColH anchors. It can be expected that the ColG-derived anchors bind more tightly to collagenous peptides than the ColH-derived anchors.

TABLE 2

Binding affinity of various collagen anchors

| Collagen anchor | $K_D$ ($\times 10^{-5}$M) | Ratio |
| --- | --- | --- |
| ColGS3aS3b | 4.46 ± 0.45 | 0.100 |
| ColGS3b | 4.54 ± 0.15 | 0.102 |
| ColHS2bS3 | 44.5 ± 0.55 | 1.00 |
| ColHS3 | 75.2 ± 0.41 | 1.69 |

Regarding Table 2, anchor proteins were dissolved in HBS-Ca buffer at concentrations ranging from $1 \times 10^{-7}$ M to $3 \times 10^{-4}$ M. Binding to the collagenous peptide, H-Gly-Pro-Arg-Gly-(Pro-Hyp-Gly)$_{12}$-NH$_2$ (SEQ ID NO: 60), was measured by surface plasmon resonance. Data were directly fit to an equation described in Materials and Methods section by least squares method to calculate values for the apparent dissociation constant ($K_D$) and uncertainty.

In-Vitro Biological Activities of Fusion Proteins

Figure 7:
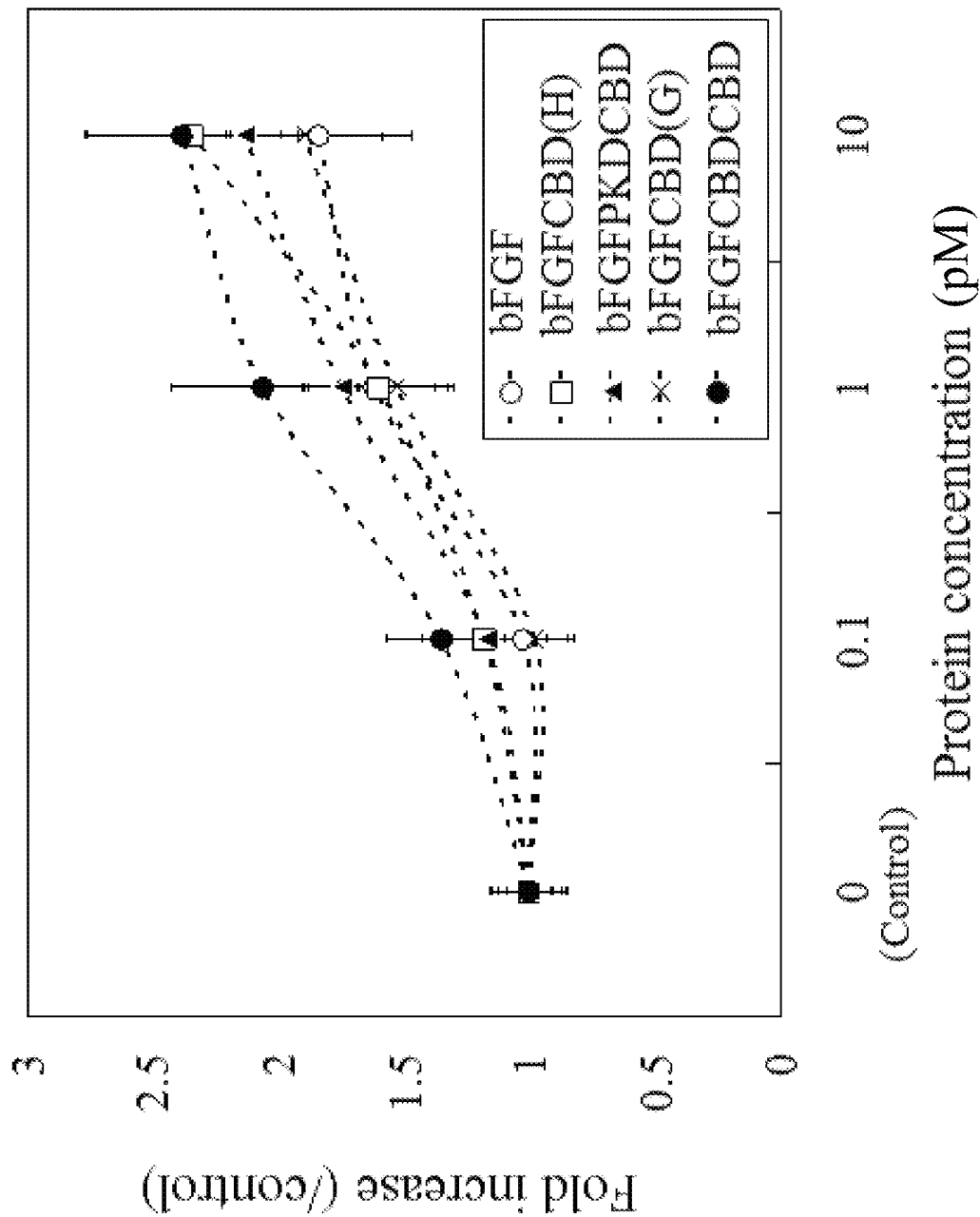
FIG. 7 shows the in-vitro proliferation activity of bFGF and CB-bFGFs. Dose-dependent induction of periosteal mesenchymal cell proliferation by bFGF and CB-bFGFs. Cell numbers were quantified three days after the treatment. Data are presented as the mean±S.E. (n=8).

The biological activities of the four CB-bFGF's were evaluated by measuring the proliferation of rat periosteal mesenchymal cells in vitro (FIG. 7). Two days after treatment with 0.1 pM bFGF-s3a-s3b (ColG), the number of cultured periosteal mesenchymal cells had significantly increased compared to the control (α-MEM) treatment group. In contrast, no significant increase was detected in the bFGF, bFGF-s3 (ColH), bFGF-s2b-s3 (ColH), or bFGF-s3b (ColG)-treated cells. However, when the concentration of the bFGF or CB-bFGF's was increased to 1 or 10 pM, the cell number had increased significantly in all forms of the growth factors compared to α-MEM-treated cells.

Figures 9A, 9B:
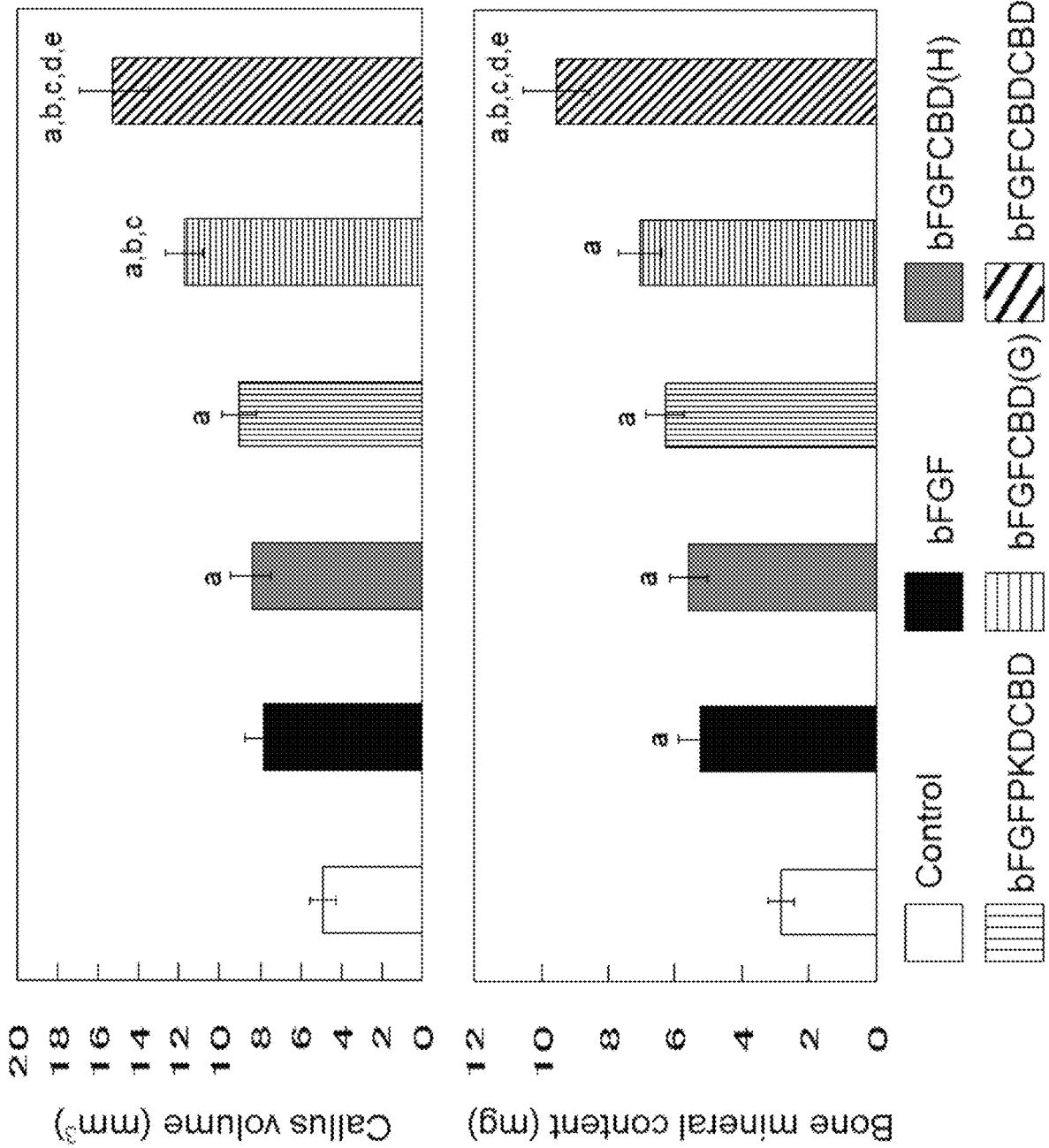
FIGS. 9A-9B shows 3D micro-CT analysis of rat femurs four weeks after the injection of poly(Pro-Hyp-Gly)$_{10}$ loaded with bFGF and CB-bFGFs at femoral fracture sites.

In-Vivo Callus Formation Induced by CB-bFGF/Poly(Pro-Hyp-Gly)$_{10}$ Composite Material Poly(Pro-Hyp-Gly)$_{10}$ gel was mixed with either PBS, bFGF (controls) or one the four prepared CB-bFGF's, and applied at fractured site in mice femurs. After 4 weeks of recovery, callus formation at the fracture sites was evaluated by micro-CT image analysis (FIGS. 8A-8F). Compared with PBS-injected fracture sites, callus volume and bone mineral content was significantly higher at sites treated with poly (Pro-Hyp-Gly)$_{10}$ in combination with bFGF or the CB-bFGF fusion proteins (FIG. 9, P<0.05). Notably, however, bFGF-s2b-s3 (ColH), bFGF-s3b (ColG) and bFGF-s3a-s3b (ColG) resulted in higher callus volume and bone mineral content compared to bFGF (FIG. 9, P<0.05). Among the three fusion proteins, bFGF-s3a-s3b (ColG) exhibited the highest efficacy for bone repair, as the callus volume and bone mineral content were significantly higher than those of all the other groups (FIG. 9, P<0.05).

Histomorphometric Findings

To investigate the mechanism by which poly(Pro-Hyp-Gly)$_{10}$/bFGF-s3a-s3b (ColG) accelerated new bone formation, histological evaluation of the treated fracture sites was performed after 2 weeks when soft callus formation was first detected in the mouse femur fracture model. Compared to the control group, large calluses were observed at the fracture sites treated with either bFGF-s2b-s3 (ColH), bFGF-s3b (ColG) or bFGF-s3a-s3b (FIGS. 10A-10F). Notably, the calluses formed by the bFGF-s3a-s3b-treatment were clearly larger than those observed in the other treatment groups (FIGS. 10A-10F). This finding indicated that poly(Pro-Hyp-Gly)$_{10}$/bFGF-s3a-s3b (ColG) accelerated periosteal cell proliferation in the early stages of fracture healing.

Discussion

Clostridial collagenases possess collagen-anchors at their C-termini. The anchors bind to collagen fibrils and collagenous peptides with triple-helical conformation, but not to denatured collagen (gelatin) [17]. The anchors are made of two types of domains, PKD and CBD, where former enhances the binding of the latter. The enzymes possess collagen anchors made of various copy numbers of PKD(s) and CBD(s). Previously we have shown the callus-inducing potential of composite materials made of collagen-carrier (high density collagen sheet/powder or demineralized bone matrix) and bFGF fused with an anchor made of a single copy each of PKD and CBD (bFGF-PKD-CBD) derived from *Clostridium histolyticum* class II collagenase, ColH [14;16]. Recently we tried to use collagenous-peptide gel instead of collagen-carrier since the former is more easily applicable by injection. In aged mice fracture models, a novel composite material made of poly(Pro-Hyp-Gly)$_{10}$ and bFGF-PKD-CBD induced greater bone formation than one made of poly(Pro-Hyp-Gly)$_{10}$ and bFGF [11]. Hence, we could speculate that efficacies of this composite material can be optimized by switching anchors with various binding affinity to the collagenous peptide carrier.

In order to estimate the binding affinity of various anchors to the peptide carrier, poly(Pro-Hyp-Gly)$_{10}$, we synthesized a longer collagenous peptide, H-Gly-Pro-Arg-Gly-(Pro-Hyp-Gly)$_{12}$-NH$_2$ as a ligand for surface plasmon resonance assay, where the first triplet, Pro-Arg-Gly, was introduced to keep its water-solubility and triple-helical conformation. Since the peptide was immobilized to the sensor chip at the N-terminus, it could be safely expected that the alteration near the N-terminus does not affect the binding significantly. A single CBD (ColG s3b) showed a K$_D$ value (4.54±0.15× 10$^{-5}$ M) to this peptide similar to that (5.72±0.473×10$^{-5}$ M) reported previously to a shorter collagenous peptide, (G(POG)$_8$) [15], indicating that the quantitative analysis performed here is reproducible. Collagen anchors (s3a-s3b and s3b) derived from class I enzyme (ColG) showed significantly higher affinity to this peptide than ones (s2b-s3 and s3) derived from class II enzyme (ColH), suggesting that the formers are more appropriate anchors toward the peptide carrier than the latters. Presence of an additional CBD (s3a) did not significantly enhance binding of ColG s3b to the synthetic peptide, suggesting that the peptide used for this assay is still too short to allow simultaneous binding of the two CBDs. An alternative possibility is that the binding between S3a and the collagen peptide is sufficiently weak to be reflected in the apparent K$_D$ value. Binding assay and/or small-angle X-ray diffraction study using a longer collagenous peptide would be necessary to solve this question.

Provided that the efficacy correlates with the binding affinity, we could expect more callus formation using bFGF fused with the ColG anchors when combined with the collangenous peptide. Hence, we prepared four CB-bFGF's with one of the anchors described above. In order to confirm that bFGF moiety in each CB-bFGF construct is intact, cell proliferation assay was performed in vitro. Four CB-bFGF and bFGF promoted cell proliferation in dose dependent manner, which indicates that bFGF moiety is active regardless to the various anchor moiety. Specific activity of the bFGF-CBD-CBD (s3a-s3b) seems to be slightly higher than the other CB-bFGF's at the lower concentrations (0.1-1.0 pM), which might be due to the binding of this CB-bFGF to collagen produced by the mesenchymal cells.

Then, osteogenic potential of the composite materials made of poly(Pro-Hyp-Gly)$_{10}$ and either of the four CB-bFGF's was compared using a mouse femur fracture model. When combined with the gel-like carrier made of poly(Pro-Hyp-Gly)$_{10}$, bFGF-CBD (ColG) and bFGF-CBD-CBD (ColG) induced large soft callus formation at 2 weeks and significantly more callus during fracture healing compared to bFGF, bFGF-PKD-CBD (ColH), or bFGF-CBD (ColH). Among the examined, bFGF-CBD-CBD (ColG) resulted in the highest callus volume and bone mineral content.

The binding affinity of collagen anchors may affect the osteogenic activity of the corresponding fusion proteins, as the rapid diffusion of target molecules from defect sites would limit their osteogenic potential [10]. We previously demonstrated that bFGF-PKD-CBD (ColH) has higher binding affinity to collagen-carrier and induces greater bone formation compared to bFGF-CBD (ColH) [10]. Among the collagen anchors used in the present study, ColG CBD(s) showed approximately 10-times higher affinity than ColH anchors to a collagenous peptide. This finding is consistent with the in-vivo results, where the treatment with bFGF fused with ColG anchors accelerated osteogenesis more efficiently compared to bFGF fused with ColH anchors when combined with a collagenous peptide carrier.

Taken together, osteogenic potentials seem to correlate with the binding affinity of collagen-anchors at least in the range we examined. It also seems likely that the tandem CBDs (ColG) increase the retention time of bFGF most at fracture sites when introduced together with collagen-like polypeptide poly(Pro-Hyp-Gly)$_{10}$ and thereby accelerate bone formation. These results suggest that bFGF-CBD-CBD (ColG) combined with poly(Pro-Hyp-Gly)$_{10}$ is a promising therapeutic material for stimulating bone repair in the clinical setting.

Previous studies have demonstrated that fusion proteins between growth factors and CBDs have superior biological activity compared to native growth factor [18;19]. For example, Han et al. [18] reported that bone morphogenetic protein containing a CBD derived from von Willebrand factor increased the in-vitro alkaline phosphatase activity of the mouse osteoblastic cell line MC3T3-E1. As bFGF stimulates periosteal mesenchymal cells [9;10;16], here, we examined the proliferation ability of bFGF and several CB-bFGF fusion proteins using rat periosteal mesenchymal cells and demonstrated that bFGF-CBD-CBD stimulated the highest cell proliferation activity of the examined proteins at a concentration as low as 1 pM. Taken together, the findings from this study indicate that bFGF-CBD-CBD possess both high collagen-binding affinity and biological activity, including the ability to stimulate callus formation during fracture healing. A recombinant collagen-binding bFGF fusion protein containing tandem CBDs from *C. histolyticum* class I collagenase ColG strongly induced bone formation when injected in combination with the collagen-like peptide poly(Pro-Hyp-Gly)$_{10}$ into mouse femur fracture sites. The high osteogenic properties of bFGF-CBD-CBD/poly(Pro-Hyp-Gly)$_{10}$ suggest that this composite material has the potential to promote fracture healing in the clinical setting.

REFERENCES FOR EXAMPLE 2

[1] Khan S N, Bostrom M P, Lane J M: Bone growth factors. Orthop Clin North Am 2000; 31:375-388.

[2] Ueno M, Urabe K, Naruse K, Uchida K, Minehara H, Yamamoto T, Steck R, Gregory L, Wullschleger M E, Schuetz M A, Itoman M: Influence of internal fixator stiffness on murine fracture healing: two types of fracture healing lead to two distinct cellular events and FGF-2 expressions. Exp Anim 2011; 60:79-87.

[3] Kato T, Kawaguchi H, Hanada K, Aoyama I, Hiyama Y, Nakamura T, Kuzutani K, Tamura M, Kurokawa T, Nakamura K: Single local injection of recombinant fibroblast growth factor-2 stimulates healing of segmental bone defects in rabbits. J Orthop Res 1998; 16:654-659.

[4] Kawaguchi H, Kurokawa T, Hanada K, Hiyama Y, Tamura M, Ogata E, Matsumoto T: Stimulation of fracture repair by recombinant human basic fibroblast growth factor in normal and streptozotocin-diabetic rats. Endocrinology 1994; 135:774-781.

[5] Kawaguchi H, Jingushi S, Izumi T, Fukunaga M, Matsushita T, Nakamura T, Mizuno K, Nakamura T, Nakamura K: Local application of recombinant human fibroblast growth factor-2 on bone repair: a dose-escalation prospective trial on patients with osteotomy. J Orthop Res 2007; 25:480-487.

[6] Kawaguchi H, Oka H, Jingushi S, Izumi T, Fukunaga M, Sato K, Matsushita T, Nakamura K: A local application of recombinant human fibroblast growth factor 2 for tibial shaft fractures: A randomized, placebo-controlled trial. J Bone Miner Res 2010; 25:2735-2743.

[7] Bauer R, Wilson J J, Philominathan S T, Davis D, Matsushita O, Sakon J: Structural comparison of ColH and ColG collagen-binding domains from *Clostridium histolyticum*. J Bacteriol 2013; 195:318-327.

[8] Bauer R, Janowska K, Taylor K, Jordan B, Gann S, Janowski T, Latimer E C, Matsushita O, Sakon J: Structures of three polycystic kidney disease-like domains from *Clostridium histolyticum* collagenases ColG and ColH. Acta Crystallogr D Biol Crystallogr 2015; 71:565-577.

[9] Uchida K, Matsushita O, Naruse K, Mima T, Nishi N, Hattori S, Ogura T, Inoue G, Tanaka K, Takaso M: Acceleration of periosteal bone formation by human basic fibroblast growth factor containing a collagen-binding domain from *Clostridium histolyticum* collagenase. J Biomed Mater Res A 2014; 102:1737-1743.

[10] Uchida K, Matsushita O, Nishi N, Inoue G, Horikawa K, Takaso M: Enhancement of periosteal bone formation by basic fibroblast-derived growth factor containing polycystic kidney disease and collagen-binding domains from *Clostridium histolyticum* collagenase. J Tissue Eng Regen Med Mar. 18, 2015.

[11] Sekiguchi H, Uchida K, Inoue G, Matsushita O, Saito W, Aikawa J, Tanaka K, Fujimaki H, Miyagi M, Takaso M: Acceleration of bone formation during fracture healing by poly(pro-hyp-gly)$_{10}$ and basic fibroblast growth factor containing polycystic kidney disease and collagen-binding domains from *Clostridium histolyticum* collagenase. J Biomed Mater Res A 2016; 104:1372-1378.

[12] Fukata Y, Itoh A, Nonaka Y, Ogawa T, Nakamura T, Matsushita O, Nishi N: Direct cytocidal effect of galectin-9 localized on collagen matrices on human immune cell lines. Biochim Biophys Acta 2014; 1840:1892-1901.

[13] Kishimoto T, Morihara Y, Osanai M, Ogata S, Kamitakahara M, Ohtsuki C, Tanihara M: Synthesis of poly (Pro-Hyp-Gly)(n) by direct poly-condensation of (Pro-Hyp-Gly)(n), where n=1, 5, and 10, and stability of the triple-helical structure. Biopolymers Oct. 15, 2005; 79:163-172.

[14] Saito W, Uchida K, Matsushita O, Inoue G, Sekiguchi H, Aikawa J, Fujimaki H, Takaso M: Acceleration of callus formation during fracture healing using basic fibroblast growth factor-kidney disease domain-collagen-binding domain fusion protein combined with allogenic demineralized bone powder. J Orthop Surg Res 2015; 10:59.

[15] Wilson J J, Matsushita O, Okabe A, Sakon J: A bacterial collagen-binding domain with novel calcium-binding motif controls domain orientation. EMBO J Apr. 15, 2003; 22:1743-1752.

[16] Saito W, Uchida K, Ueno M, Matsushita O, Inoue G, Nishi N, Ogura T, Hattori S, Fujimaki H, Tanaka K, Takaso M: Acceleration of bone formation during fracture healing by injectable collagen powder and human basic fibroblast growth factor containing a collagen-binding domain from *Clostridium histolyticum* collagenase. J Biomed Mater Res A 2014; 102:3049-3055.

[17] Matsushita O, Koide T, Kobayashi R, Nagata K, Okabe A: Substrate recognition by the collagen-binding domain of *Clostridium histolyticum* class I collagenase. J Biol Chem Mar. 23, 2001; 276:8761-8770.

[18] Han X, Zhang W, Gu J, Zhao H, Ni L, Han J, Zhou Y, Gu Y, Zhu X, Sun J, Hou X, Yang H, Dai J, Shi Q: Accelerated postero-lateral spinal fusion by collagen scaffolds modified with engineered collagen-binding human bone morphogenetic protein-2 in rats. PLoS One 2014; 9:e98480.

[19] Shiozaki Y, Kitajima T, Mazaki T, Yoshida A, Tanaka M, Umezawa A, Nakamura M, Yoshida Y, Ito Y, Ozaki T, Matsukawa A: Enhanced in vivo osteogenesis by nanocarrier-fused bone morphogenetic protein-4. Int J Nanomedicine 2013; 8:1349-1360.

We claim:

1. A collagen-binding agent comprising a first collagen-binding domain and a second collagen-binding domain linked by a domain linker and a therapeutic agent linked to at least one of the collagen-binding domains by a therapeutic agent linker,
    wherein the collagen-binding agent lacks collagenase activity;
    wherein the therapeutic agent is fibroblast growth factor (FGF);
    wherein the two collagen-binding domains bind to collagen with a $K_D$ of between 100 µM and 0.1 nM;
    wherein the first collagen-binding domain is selected from the group consisting of the polypeptides of SEQ ID NOs: 1-14, and the second collagen-binding domain is selected from the group consisting of the polypeptides of SEQ ID NOs: 15-30; and
    wherein the C-terminus of the first collagen-binding domain is linked to the N-terminus of the second collagen-binding domain by the domain linker.

2. The collagen-binding agent of claim 1, wherein the domain linker comprises a polypeptide.

3. The collagen-binding agent of claim 1, wherein the domain linker comprises a polypeptide selected from the group consisting of the polypeptides of SEQ ID NOs: 48-55 or a polypeptide having at least 80% sequence identity to any one of the polypeptides of SEQ ID NOs: 48-55.

4. The collagen-binding agent of claim 1, wherein the therapeutic agent linker comprises a polypeptide.

5. The collagen-binding agent of claim 4, wherein the C-terminus of the therapeutic agent is linked to the N-terminus of the collagen-binding domains by the therapeutic agent linker.

6. A pharmaceutical composition comprising the collagen-binding agent of claim 1 and a pharmaceutical carrier.

7. A method of stimulating bone formation in a subject having a bone condition comprising administering to the subject a therapeutically effective amount of the collagen-binding agent of claim 1.

8. The method of claim 7, wherein the subject is a mammal.

9. The method of claim 8, wherein the mammal is a human.

* * * * *

SEQUENCE LISTING

<160> NUMBER OF SEQ ID NOS: 62

<210> SEQ ID NO 1
<211> LENGTH: 113
<212> TYPE: PRT
<213> ORGANISM: Clostridium histolyticum
<220> FEATURE:
<221> NAME/KEY: misc_feature
<222> LOCATION: (1)..(113)
<223> OTHER INFORMATION: ColG s3a domain

<400> SEQUENCE: 1

Thr Lys Glu Met Glu Pro Asn Asp Asp Ile Lys Glu Ala Asn Gly Pro
1               5                   10                  15

Ile Val Glu Gly Val Thr Val Lys Gly Asp Leu Asn Gly Ser Asp Asp
            20                  25                  30

Ala Asp Thr Phe Tyr Phe Asp Val Lys Glu Asp Gly Asp Val Thr Ile
        35                  40                  45

Glu Leu Pro Tyr Ser Gly Ser Ser Asn Phe Thr Trp Leu Val Tyr Lys
    50                  55                  60

Glu Gly Asp Asp Gln Asn His Ile Ala Ser Gly Ile Asp Lys Asn Asn
65                  70                  75                  80

Ser Lys Val Gly Thr Phe Lys Ser Thr Lys Gly Arg His Tyr Val Phe
                85                  90                  95

Ile Tyr Lys His Asp Ser Ala Ser Asn Ile Ser Tyr Ser Leu Asn Ile
            100                 105                 110

Lys

<210> SEQ ID NO 2
<211> LENGTH: 111
<212> TYPE: PRT
<213> ORGANISM: B. brevis
<220> FEATURE:
<221> NAME/KEY: misc_feature
<222> LOCATION: (1)..(111)
<223> OTHER INFORMATION: ColG s3a domain

<400> SEQUENCE: 2

Glu Lys Glu Gln Glu Pro Asn Asn Ser Phe Ser Glu Ala Asn Pro Leu
1               5                   10                  15

Lys Ser Asn Val Glu Leu Ser Gly Gln Thr Ser Lys Gln Asp Asp Lys
            20                  25                  30

Asp Ile Phe Ala Leu Lys Val Leu Gly Asn Gly Thr Val Lys Ile Asn
        35                  40                  45

Val Thr Ser Glu His Asp Thr Gly Leu Asn Trp Val Val His His Glu
    50                  55                  60

Asp Asp Leu Asn Asn Tyr Leu Ala Tyr Pro Lys Thr Ser Gly Lys Thr
65                  70                  75                  80

Leu Ser Gly Glu Phe Glu Ala Thr Pro Gly Tyr Tyr Leu Ser Val
                85                  90                  95

Tyr Asn Phe Asn Gly Glu Thr Ile Pro Tyr Lys Val Thr Ala Glu
            100                 105                 110

<210> SEQ ID NO 3
<211> LENGTH: 115
<212> TYPE: PRT
<213> ORGANISM: C. sporogenes
<220> FEATURE:
<221> NAME/KEY: misc_feature
<222> LOCATION: (1)..(115)
<223> OTHER INFORMATION: ColG s3a domain

<400> SEQUENCE: 3

```
Val Ser Glu Lys Glu Asp Asn Asn Asp Phe Thr Thr Ala Asn Pro Val
1               5                   10                  15

Tyr Tyr Lys Asp Leu Val Asn Gly Ser Val Ser Ser Asp Asn Lys
            20                  25                  30

Asp Thr Phe Tyr Phe Thr Val Thr Lys Pro Ser Asp Ile Thr Ile Thr
            35                  40                  45

Val Glu Lys Thr Asn Asn Asp Lys Ser Glu Phe Asn Trp Leu Leu Phe
50                  55                  60

Ser Asp Glu Asp Lys Ser Asn Tyr Met Ala Phe Pro Asn Lys Glu Leu
65                  70                  75                  80

Gly Asn Gln Leu Ser Asn Thr Val Lys Ile Asn Lys Pro Gly Lys Tyr
                85                  90                  95

Tyr Leu Val Ile Tyr Lys Thr Leu Gly Glu Lys Val Asp Tyr Lys Phe
                100                 105                 110

Ser Ile Glu
        115
```

<210> SEQ ID NO 4
<211> LENGTH: 115
<212> TYPE: PRT
<213> ORGANISM: C. botulinum
<220> FEATURE:
<221> NAME/KEY: misc_feature
<222> LOCATION: (1)..(115)
<223> OTHER INFORMATION: C. botulinumA3 ColG s3a domain

<400> SEQUENCE: 4

```
Val Ser Glu Lys Glu Asn Asn Asn Asp Tyr Val Asn Ala Asn Pro Val
1               5                   10                  15

Tyr Ser Lys Asp Leu Val Asn Gly Ser Val Ser Ser Asp Asp Arg
            20                  25                  30

Asp Ile Phe Tyr Phe Asn Val Thr Lys Pro Ser Asp Ile Thr Ile Asn
            35                  40                  45

Val Glu Lys Ile Asn Lys Asp Lys Ser Glu Phe Ser Trp Leu Leu Phe
50                  55                  60

Ser Glu Glu Asp Lys Ser Asn Tyr Ile Thr Tyr Pro Asn Lys Glu Leu
65                  70                  75                  80

Glu Asn Leu Phe Tyr Ser Thr Val Lys Ile Asp Lys Pro Gly Lys Tyr
                85                  90                  95

Tyr Leu Val Ile Tyr Lys Val Ser Gly Glu Lys Ser Asp Tyr Arg Phe
                100                 105                 110

Asn Ile Glu
        115
```

<210> SEQ ID NO 5
<211> LENGTH: 113
<212> TYPE: PRT
<213> ORGANISM: C. perfringens
<220> FEATURE:
<221> NAME/KEY: misc_feature
<222> LOCATION: (1)..(113)
<223> OTHER INFORMATION: ColG s3a domain

<400> SEQUENCE: 5

```
Ile Asn Glu Ser Glu Pro Asn Asn Asp Phe Glu Lys Ala Asn Gln Ile
1               5                   10                  15

Ala Lys Ser Asn Met Leu Val Lys Gly Thr Leu Ser Glu Glu Asp Tyr
```

```
            20                  25                  30

Ser Asp Lys Tyr Tyr Phe Asp Val Ala Lys Lys Gly Asn Val Lys Ile
        35                  40                  45

Thr Leu Asn Asn Leu Asn Ser Val Gly Ile Thr Trp Thr Leu Tyr Lys
    50                  55                  60

Glu Gly Asp Leu Asn Asn Tyr Val Leu Tyr Ala Thr Gly Asn Glu Gly
65                  70                  75                  80

Thr Val Leu Lys Gly Glu Lys Thr Leu Glu Pro Gly Arg Tyr Tyr Leu
                85                  90                  95

Ser Val Tyr Thr Tyr Asp Asn Gln Ser Gly Ala Tyr Thr Val Asn Val
            100                 105                 110

Lys

<210> SEQ ID NO 6
<211> LENGTH: 113
<212> TYPE: PRT
<213> ORGANISM: C. sordellii
<220> FEATURE:
<221> NAME/KEY: misc_feature
<222> LOCATION: (1)..(113)
<223> OTHER INFORMATION: ColG s3a domain

<400> SEQUENCE: 6

Ser Gln Glu Val Gly Asn Asp Asp Thr Phe Glu Thr Ala Asn Gly Pro
1               5                   10                  15

Ile Lys Ile Asn Thr Asn Tyr Ser Gly Asp Leu Ser Asp Thr Asp Asn
            20                  25                  30

Lys Asp Tyr Tyr Tyr Phe Asn Leu Asp Asn Pro Ser Asn Ile Asn Ile
        35                  40                  45

Thr Leu Glu Asn Leu Asp Asn Lys Gly Ile Ser Trp Gln Leu Phe His
    50                  55                  60

Glu Ser Asp Leu Asn Asn Tyr Val Ala Tyr Pro Thr Thr Ser Gly Ala
65                  70                  75                  80

Ile Leu Asn Gly Asp Tyr Asn Ala Thr Lys Pro Gly Lys Tyr Tyr Ile
                85                  90                  95

Leu Val Tyr Asn His Asp Lys Ser Ile Ala Asn Tyr Asn Leu Lys Val
            100                 105                 110

Asn

<210> SEQ ID NO 7
<211> LENGTH: 116
<212> TYPE: PRT
<213> ORGANISM: C. histolyticum
<220> FEATURE:
<221> NAME/KEY: misc_feature
<222> LOCATION: (1)..(116)
<223> OTHER INFORMATION: ColG s3a domain

<400> SEQUENCE: 7

Thr Pro Ile Thr Lys Glu Met Glu Pro Asn Asp Asp Ile Lys Glu Ala
1               5                   10                  15

Asn Gly Pro Ile Val Glu Gly Val Thr Val Lys Gly Asp Leu Asn Gly
            20                  25                  30

Ser Asp Asp Ala Asp Thr Phe Tyr Phe Asp Val Lys Glu Asp Gly Asp
        35                  40                  45

Val Thr Ile Glu Leu Pro Tyr Ser Gly Ser Ser Asn Phe Thr Trp Leu
    50                  55                  60

Val Tyr Lys Glu Gly Asp Asp Gln Asn His Ile Ala Ser Gly Ile Asp
```

```
                65                  70                  75                  80
Lys Asn Asn Ser Lys Val Gly Thr Phe Lys Ser Thr Lys Gly Arg His
                    85                  90                  95

Tyr Val Phe Ile Tyr Lys His Asp Ser Ala Ser Asn Ile Ser Tyr Ser
                100                 105                 110

Leu Asn Ile Lys
        115

<210> SEQ ID NO 8
<211> LENGTH: 117
<212> TYPE: PRT
<213> ORGANISM: C. sporogenes
<220> FEATURE:
<221> NAME/KEY: misc_feature
<222> LOCATION: (1)..(117)
<223> OTHER INFORMATION: ColG s3a domain

<400> SEQUENCE: 8

Leu Val Ile Ser Glu Lys Glu Asp Asn Asp Ser Phe Asp Lys Ala Asn
1               5                   10                  15

Arg Val Cys Lys Asn Gln Ser Val Leu Ala Thr Leu Asp Thr Asn Asp
                20                  25                  30

Asn Arg Asp Thr Tyr Tyr Phe Asp Ala Leu Thr Ala Gly Thr Ile Asp
                35                  40                  45

Val Ile Met Glu Asn Thr Asp Asn Asn Ser Asn Ile Phe Asn Trp Leu
            50                  55                  60

Ala Tyr Ser Ser Asp Asn Thr Asn Asn Tyr Ile Gly Tyr Ser Thr Lys
65                  70                  75                  80

Lys Glu Gly Asn Lys Leu Leu Gly Ser Phe Lys Val Pro Lys Pro Gly
                85                  90                  95

Arg Tyr Tyr Ile Leu Ala Tyr Lys Asn Ser Ser Asn Lys Ile Asn Tyr
                100                 105                 110

Lys Leu Thr Ile Asn
        115

<210> SEQ ID NO 9
<211> LENGTH: 117
<212> TYPE: PRT
<213> ORGANISM: C. botulinum
<220> FEATURE:
<221> NAME/KEY: misc_feature
<222> LOCATION: (1)..(117)
<223> OTHER INFORMATION: C. botulinumB ColG s3a domain

<400> SEQUENCE: 9

Ile Asn Val Asp Glu Glu Tyr Asn Asp Asp Phe Glu Cys Ala Asn
1               5                   10                  15

Asn Ile Phe Lys Asn Gln Ile Met Ser Gly Asn Leu Asp Ser Ser Asp
                20                  25                  30

Lys Cys Asp Thr Phe Ser Phe Asn Ala Leu Ser Ala Gly Thr Ile Asn
                35                  40                  45

Val Thr Leu Glu Asn Ser Asn Ser Asp Ser Ser Thr Val Asn Trp Leu
            50                  55                  60

Ala Tyr Ser Ser Glu Asp Thr Asn Tyr Ile Gly Tyr Ala Ser Glu
65                  70                  75                  80

Asn Asp Gly Asn Lys Phe Ser Gly Lys Phe Lys Val Asn Lys Pro Gly
                85                  90                  95

Lys Tyr Tyr Ile Val Ala Tyr Glu Val Asn Gly Ala Asp Ser Lys Tyr
                100                 105                 110
```

```
Lys Leu Lys Val Asp
        115

<210> SEQ ID NO 10
<211> LENGTH: 117
<212> TYPE: PRT
<213> ORGANISM: C. tetani E88
<220> FEATURE:
<221> NAME/KEY: misc_feature
<222> LOCATION: (1)..(117)
<223> OTHER INFORMATION: ColG s3a domain

<400> SEQUENCE: 10

Asn Val Ile Tyr Glu Lys Glu Asn Asn Asp Ser Phe Asp Lys Ala Asn
1               5                   10                  15

Lys Ile His Lys Asn Gln Ile Val Met Ala Thr Leu Asp Thr Glu Asp
            20                  25                  30

Tyr Arg Asp Thr Phe Tyr Phe Asp Ala Leu Thr Ser Gly Ser Ile Asp
        35                  40                  45

Ile Thr Ile Glu Asn Ile His Gly Asn Ser Asp Ala Phe Asn Trp Leu
    50                  55                  60

Val Tyr Asn Asp Glu Asp Leu Asn Asn Tyr Ile Ala Tyr Pro Thr Lys
65                  70                  75                  80

Lys Glu Asp Asn Lys Leu Met Gly Ser Phe Lys Val His Lys Pro Gly
                85                  90                  95

Arg Tyr Tyr Ile Leu Val Tyr Lys Thr Ser Leu Asn Lys Val Asn Tyr
            100                 105                 110

Lys Leu Asn Ile Ser
        115

<210> SEQ ID NO 11
<211> LENGTH: 115
<212> TYPE: PRT
<213> ORGANISM: C. perfringens
<220> FEATURE:
<221> NAME/KEY: misc_feature
<222> LOCATION: (1)..(115)
<223> OTHER INFORMATION: ColG s3a domain

<400> SEQUENCE: 11

Glu Val Ile Asn Glu Ser Glu Pro Asn Asn Asp Phe Glu Lys Ala Asn
1               5                   10                  15

Gln Ile Ala Lys Ser Asn Met Leu Val Lys Gly Thr Leu Ser Glu Glu
            20                  25                  30

Asp Tyr Ser Asp Lys Tyr Tyr Phe Asp Val Ala Lys Lys Gly Asn Val
        35                  40                  45

Lys Ile Thr Leu Asn Asn Leu Asn Ser Val Gly Ile Thr Trp Thr Leu
    50                  55                  60

Tyr Lys Glu Gly Asp Leu Asn Asn Tyr Val Leu Tyr Ala Thr Gly Asn
65                  70                  75                  80

Asp Gly Thr Val Leu Lys Gly Glu Lys Thr Leu Glu Pro Gly Arg Tyr
                85                  90                  95

Tyr Leu Ser Val Tyr Thr Tyr Asp Asn Gln Ser Gly Thr Tyr Thr Val
            100                 105                 110

Asn Val Lys
        115

<210> SEQ ID NO 12
<211> LENGTH: 115
```

```
<212> TYPE: PRT
<213> ORGANISM: B. brevis
<220> FEATURE:
<221> NAME/KEY: misc_feature
<222> LOCATION: (1)..(115)
<223> OTHER INFORMATION: ColG s3a domain

<400> SEQUENCE: 12

Asp Gly Ser Glu Thr Glu Gln Pro Asn Pro Asn Pro Glu Ser Ser
1               5                   10                  15

Leu Ser Leu Gly Lys Pro Ile Thr Gly Ile Ile His Pro Gln Lys Pro
            20                  25                  30

Ser Gln Glu Phe Arg Leu Asp Val Lys Ser Ala Gln Gln Leu Gln Val
        35                  40                  45

Glu Met Glu Thr Lys Gln Gly Asp Gly Val Ala Trp Leu Val Phe His
50                  55                  60

Glu Ala Asp Arg Glu Asn Tyr Ile Ser Tyr Pro Thr Lys Arg Glu Gly
65                  70                  75                  80

Asn Lys Leu Ile Gly Ser Phe Asp Ala Lys Pro Gly Thr Tyr Tyr Val
                85                  90                  95

Thr Ala Tyr Thr Tyr Arg Thr Glu Gln Glu Asp Gln Pro Phe Arg Leu
            100                 105                 110

Leu Val Thr
        115

<210> SEQ ID NO 13
<211> LENGTH: 114
<212> TYPE: PRT
<213> ORGANISM: P. dendritiformis
<220> FEATURE:
<221> NAME/KEY: misc_feature
<222> LOCATION: (1)..(114)
<223> OTHER INFORMATION: ColG s3a domain

<400> SEQUENCE: 13

Pro Asn Ala Asp His Glu Pro Asn Asp Ser Trp Glu Gln Ala Val Pro
1               5                   10                  15

Leu Asp Gly Thr Gly Val Pro Val Ser Gly Lys Leu Ser Asp Thr Asp
            20                  25                  30

Arg Val Asp Val Tyr Arg Phe Asp Ala Gly Lys Ala Glu Gln Trp Thr
        35                  40                  45

Ile Glu Leu Glu Thr Glu Gln Ala Gln Ser Val Ala Trp Val Val His
50                  55                  60

His Glu Ser Asp Leu Asn Asn Tyr Ala Ala Tyr Pro Thr Gln Val Glu
65                  70                  75                  80

Gly Thr Ser Val Ala Gly Ser Val Asp Ala Val Pro Gly Thr Tyr Tyr
                85                  90                  95

Val Tyr Val Tyr Ser Val Gly Asn Gly Glu Gln Ser Tyr Arg Leu Val
            100                 105                 110

Val Gln

<210> SEQ ID NO 14
<211> LENGTH: 116
<212> TYPE: PRT
<213> ORGANISM: C. sordellii
<220> FEATURE:
<221> NAME/KEY: misc_feature
<222> LOCATION: (1)..(116)
<223> OTHER INFORMATION: ColG s3a domain

<400> SEQUENCE: 14
```

```
Pro Lys Gly Ser Gln Glu Val Gly Asn Asp Asp Thr Phe Glu Thr Ala
1               5                   10                  15

Asn Gly Pro Ile Lys Ile Asn Thr Asn Tyr Ser Gly Asp Leu Ser Asp
            20                  25                  30

Thr Asp Asn Lys Asp Tyr Tyr Tyr Phe Asn Leu Asp Asn Pro Ser Asn
        35                  40                  45

Ile Asn Ile Thr Leu Glu Asn Leu Asp Asn Lys Gly Ile Ser Trp Gln
    50                  55                  60

Leu Phe His Glu Ser Asp Leu Asn Asn Tyr Val Ala Tyr Pro Thr Thr
65                  70                  75                  80

Ser Gly Ala Ile Leu Asn Gly Asp Tyr Asn Ala Thr Lys Pro Gly Lys
                85                  90                  95

Tyr Tyr Ile Leu Val Tyr Asn His Asp Lys Ser Ile Ala Asn Tyr Asn
            100                 105                 110

Leu Lys Val Asn
        115
```

<210> SEQ ID NO 15
<211> LENGTH: 111
<212> TYPE: PRT
<213> ORGANISM: Clostridium histolyticum
<220> FEATURE:
<221> NAME/KEY: misc_feature
<222> LOCATION: (1)..(111)
<223> OTHER INFORMATION: ColG s3b domain

<400> SEQUENCE: 15

```
Leu Lys Glu Lys Glu Asn Asn Asp Ser Ser Asp Lys Ala Thr Val Ile
1               5                   10                  15

Pro Asn Phe Asn Thr Thr Met Gln Gly Ser Leu Leu Gly Asp Asp Ser
            20                  25                  30

Arg Asp Tyr Tyr Ser Phe Glu Val Lys Glu Glu Gly Glu Val Asn Ile
        35                  40                  45

Glu Leu Asp Lys Lys Asp Glu Phe Gly Val Thr Trp Thr Leu His Pro
    50                  55                  60

Glu Ser Asn Ile Asn Asp Arg Ile Thr Tyr Gly Gln Val Asp Gly Asn
65                  70                  75                  80

Lys Val Ser Asn Lys Val Lys Leu Arg Pro Gly Lys Tyr Tyr Leu Leu
                85                  90                  95

Val Tyr Lys Tyr Ser Gly Ser Gly Asn Tyr Glu Leu Arg Val Asn
            100                 105                 110
```

<210> SEQ ID NO 16
<211> LENGTH: 111
<212> TYPE: PRT
<213> ORGANISM: Bacillus sp.
<220> FEATURE:
<221> NAME/KEY: misc_feature
<222> LOCATION: (1)..(111)
<223> OTHER INFORMATION: ColG s3b domain

<400> SEQUENCE: 16

```
Lys Thr Glu Ile Glu Pro Asn Asn Arg Pro Glu Glu Ala Thr Met Leu
1               5                   10                  15

Pro Phe Asn Thr Pro Leu Ser Gly Ser Leu Met Glu Asp Asp His Thr
            20                  25                  30

Asp Val Tyr Glu Phe Asn Val Thr Ser Pro Lys Glu Ile Asp Ile Ser
        35                  40                  45
```

```
Val Leu Asn Glu Asn Gln Ile Gly Met Thr Trp Val Leu Tyr His Glu
    50                  55                  60

Ser Asp Ser Gln Asn Tyr Ala Ser Phe Gly Gln Glu Asp Gly Asn Met
65                  70                  75                  80

Ile Asn Gly Lys Trp Asn Ala Lys Pro Gly Lys Tyr Tyr Leu Tyr Val
                85                  90                  95

Tyr Lys Phe Glu Asn Glu Asn Gly Thr Tyr Thr Val His Val Gln
            100                 105                 110

<210> SEQ ID NO 17
<211> LENGTH: 111
<212> TYPE: PRT
<213> ORGANISM: L. sphaericus
<220> FEATURE:
<221> NAME/KEY: misc_feature
<222> LOCATION: (1)..(111)
<223> OTHER INFORMATION: ColG s3b domain

<400> SEQUENCE: 17

Lys Ala Glu Ile Glu Pro Asn Asn Arg Pro Glu Glu Ala Thr Ile Leu
1               5                   10                  15

Pro Phe Asn Thr Pro Leu Lys Gly Arg Leu Met Asp Asp Asp His Thr
            20                  25                  30

Asp Val Tyr Glu Phe Asn Val Thr Ser Pro Lys Glu Leu Asp Ile Ser
        35                  40                  45

Val Leu Asn Glu Asn Arg Ile Gly Met Thr Trp Val Leu Tyr His Glu
    50                  55                  60

Ser Asp Ser Gln Asn Tyr Ala Ser Phe Gly Gln Glu Glu Gly Asn Met
65                  70                  75                  80

Ile Asn Gly Lys Leu His Ala Glu Pro Gly Lys Tyr Tyr Leu Tyr Val
                85                  90                  95

Tyr Lys Phe Glu Asn Glu Asn Gly Thr Tyr Thr Val Gln Val Gln
            100                 105                 110

<210> SEQ ID NO 18
<211> LENGTH: 111
<212> TYPE: PRT
<213> ORGANISM: B. brevis
<220> FEATURE:
<221> NAME/KEY: misc_feature
<222> LOCATION: (1)..(111)
<223> OTHER INFORMATION: ColG s3b domain

<400> SEQUENCE: 18

Pro Thr Glu Val Glu Pro Asn Asn Ser Phe Asp Asp Ala Asn Thr Leu
1               5                   10                  15

Gln Leu Gly Lys Glu Ile Ser Gly Gln Thr Asp Arg Thr Asp Asp Lys
            20                  25                  30

Asp Thr Tyr Met Ile Gln Val Glu Glu Glu Gly Val Ile Gln Val Thr
        35                  40                  45

Val Ser Ser Glu Lys Asp Glu Gly Leu Asn Trp Val Val Phe His Glu
    50                  55                  60

Asp Asp Leu Lys Thr Tyr Phe Ala Tyr Pro Lys Thr Thr Gly Lys Lys
65                  70                  75                  80

Leu Thr Gly Glu Phe Glu Ala Lys Pro Gly Lys Tyr Tyr Leu Leu Val
                85                  90                  95

Tyr Asn Thr Asn Asn Thr Lys Ile Pro Tyr Lys Ala Ile Val Asn
            100                 105                 110
```

```
<210> SEQ ID NO 19
<211> LENGTH: 112
<212> TYPE: PRT
<213> ORGANISM: C. perfringens
<220> FEATURE:
<221> NAME/KEY: misc_feature
<222> LOCATION: (1)..(112)
<223> OTHER INFORMATION: ColG s3b domain

<400> SEQUENCE: 19

Ile Lys Glu Val Glu Asn Asn Asp Phe Asp Lys Ala Met Lys Val
1               5                   10                  15

Asp Ser Asn Ser Lys Ile Val Gly Thr Leu Ser Asn Asp Leu Lys
                20                  25                  30

Asp Ile Tyr Ser Ile Asp Ile Lys Asn Pro Ser Asp Leu Asn Ile Val
        35                  40                  45

Val Glu Asn Leu Asp Asn Ile Lys Met Asn Trp Leu Leu Tyr Ser Ala
    50                  55                  60

Asp Asp Leu Ser Asn Tyr Val Asp Tyr Ala Asn Ala Asp Gly Asn Lys
65                  70                  75                  80

Leu Ser Asn Thr Cys Lys Leu Asn Pro Gly Lys Tyr Tyr Leu Cys Val
                85                  90                  95

Tyr Gln Phe Glu Asn Ser Gly Thr Gly Asn Tyr Thr Val Asn Leu Gln
            100                 105                 110

<210> SEQ ID NO 20
<211> LENGTH: 115
<212> TYPE: PRT
<213> ORGANISM: C. sporogenes
<220> FEATURE:
<221> NAME/KEY: misc_feature
<222> LOCATION: (1)..(115)
<223> OTHER INFORMATION: ColG s3b domain

<400> SEQUENCE: 20

Ile Ser Glu Lys Glu Asp Asn Asp Ser Phe Lys Ala Asn Arg Val
1               5                   10                  15

Gly Lys Asn Gln Thr Val Leu Ala Thr Leu Asp Thr Lys Asp Asn Arg
                20                  25                  30

Asp Thr Tyr Tyr Phe Asp Ala Leu Ala Ala Arg Thr Ile Asp Ile Val
        35                  40                  45

Met Glu Asn Thr Asp Asn Asn Ser Thr Ile Phe Asn Trp Leu Ala Tyr
    50                  55                  60

Ser Ser Asp Asn Thr Asn Asn Tyr Ile Gly Tyr Pro Thr Lys Lys Glu
65                  70                  75                  80

Gly Asn Lys Leu Met Gly Ser Phe Lys Val Pro Lys Pro Gly Arg Tyr
                85                  90                  95

Tyr Ile Leu Ala Tyr Lys Asn Ser Ser Asn Lys Ile Asn Tyr Lys Leu
            100                 105                 110

Thr Ile Asn
        115

<210> SEQ ID NO 21
<211> LENGTH: 115
<212> TYPE: PRT
<213> ORGANISM: C. botulinum
<220> FEATURE:
<221> NAME/KEY: misc_feature
<222> LOCATION: (1)..(115)
<223> OTHER INFORMATION: C. botulinumA3 ColG s3b domain

<400> SEQUENCE: 21
```

Ile Ser Glu Lys Glu Asp Asn Ser Phe Asp Lys Ala Asn Arg Val
1               5                   10                  15

Cys Lys Asn Gln Ser Val Ile Ala Thr Leu Asp Thr Asn Asp Pro Arg
                20                  25                  30

Asp Thr Tyr Tyr Phe Asp Ala Leu Thr Ala Gly Asn Ile Glu Val Thr
            35                  40                  45

Met Gly Asn Thr Asp Asn Ser Ser Asn Glu Phe Asn Trp Leu Ala Tyr
    50                  55                  60

Ser Ser Asp Asn Thr Asn Asn Tyr Ile Gly Tyr Ala Thr Lys Arg Glu
65                  70                  75                  80

Gly Asn Lys Ile Thr Gly Asn Phe Lys Val Asp Lys Pro Gly Arg Tyr
                85                  90                  95

Tyr Ile Val Ala Tyr Lys Thr Ser Ser Asn Lys Ile Asn Tyr Lys Leu
                100                 105                 110

Asn Ile Lys
        115

<210> SEQ ID NO 22
<211> LENGTH: 113
<212> TYPE: PRT
<213> ORGANISM: C. sordellii
<220> FEATURE:
<221> NAME/KEY: mis

```
                    35                  40                  45

Glu Leu Asp Lys Lys Asp Glu Phe Gly Val Thr Trp Thr Leu His Pro
 50                  55                  60

Glu Ser Asn Ile Asn Asp Arg Ile Thr Tyr Gly Gln Val Asp Gly Asn
 65                  70                  75                  80

Lys Val Ser Asn Lys Val Lys Leu Arg Pro Gly Lys Tyr Tyr Leu Leu
                 85                  90                  95

Val Tyr Lys Tyr Ser Gly Ser Gly Asn Tyr Glu Leu Arg Val Asn Lys
            100                 105                 110

<210> SEQ ID NO 24
<211> LENGTH: 111
<212> TYPE: PRT
<213> ORGANISM: C. sporogenes
<220> FEATURE:
<221> NAME/KEY: misc_feature
<222> LOCATION: (1)..(111)
<223> OTHER INFORMATION: ColG s3b domain

<400> SEQUENCE: 24

Ile His Glu Lys Glu Asn Asn Asp Ser Phe Glu Ser Ala Asn Lys Ile
  1               5                  10                  15

Val Pro Asp Ala Pro Val Leu Gly Ser Leu Asn Gly Glu Asp Leu Arg
                 20                  25                  30

Asp Ile Tyr Ser Phe Asp Ile Lys Glu Thr Lys Asp Leu Asn Ile Lys
             35                  40                  45

Leu Thr Asn Leu Asn Asn Leu Gly Leu Thr Trp Thr Leu Tyr Lys Glu
 50                  55                  60

Ser Asp Leu Thr Asn Tyr Ile Ala Tyr Gly Ser Lys Leu Gly Asn Thr
 65                  70                  75                  80

Ile Val Gly Asn Cys His Val Thr Pro Gly Lys Tyr Tyr Leu Tyr Val
                 85                  90                  95

Tyr Lys Tyr Ser Gly Asn Ser Gly Asn Tyr Ser Leu Ile Ile Lys
            100                 105                 110

<210> SEQ ID NO 25
<211> LENGTH: 111
<212> TYPE: PRT
<213> ORGANISM: C. botulinum
<220> FEATURE:
<221> NAME/KEY: misc_feature
<222> LOCATION: (1)..(111)
<223> OTHER INFORMATION: C. botulinumB ColG s3b domain

<400> SEQUENCE: 25

Ile Lys Glu Glu Ile Asn Asp Asp Ser Phe Asp Ser Ala Thr Lys Ile
  1               5                  10                  15

Lys Ala Asn Ser Thr Ile Thr Asp Thr Leu Asn Gly Glu Asp Asn Lys
                 20                  25                  30

Asp Ile Cys Tyr Phe Asn Val Asn Asn Ser Asp Leu Asn Ile Glu
             35                  40                  45

Leu Asn Ser Leu Thr Asn Leu Gly Val Ala Trp Gln Leu Phe Ser Glu
 50                  55                  60

Glu Asp Leu Asp Asn Tyr Ile Ala Tyr Gly Ser Gln Ser Gly Asp Ser
 65                  70                  75                  80

Ile Val Gly Thr Ala Asn Val Gln Pro Gly Lys Tyr Tyr Leu Leu Ile
                 85                  90                  95

Tyr Lys Tyr Thr Gln Ala Asp Gly Ser Tyr Thr Phe Thr Ile Lys
            100                 105                 110
```

<210> SEQ ID NO 26
<211> LENGTH: 111
<212> TYPE: PRT
<213> ORGANISM: C. tetani E88
<220> FEATURE:
<221> NAME/KEY: misc_feature
<222> LOCATION: (1)..(111)
<223> OTHER INFORMATION: ColG s3b domain

<400> SEQUENCE: 26

Ile His Glu Lys Glu Asn Asn Asp Ser Phe Glu Thr Ala Asn Lys Ile
1               5                   10                  15

Thr Leu Asp Thr Leu Val Leu Gly Asn Leu Asp Tyr Lys Asp Val Ser
            20                  25                  30

Asp Ile Tyr Ser Phe Asp Ile Glu Asn Thr Lys Asp Leu Asn Ile Lys
        35                  40                  45

Leu Thr Asn Leu Asn Asn Leu Gly Ile Ala Trp Asn Leu Tyr Lys Glu
    50                  55                  60

Ser Asp Leu Asn Asn Tyr Ile Ala Tyr Gly Ala Lys Ser Asp Asn Ala
65                  70                  75                  80

Ile Val Gly Lys Cys Asn Leu Ser Pro Gly Lys Tyr Tyr Leu Tyr Val
                85                  90                  95

Tyr Lys Tyr Ser Gly Asp Lys Gly Asn Tyr Ser Val Ile Ile Asn
            100                 105                 110

<210> SEQ ID NO 27
<211> LENGTH: 114
<212> TYPE: PRT
<213> ORGANISM: C. perfringens
<220> FEATURE:
<221> NAME/KEY: misc_feature
<222> LOCATION: (1)..(114)
<223> OTHER INFORMATION: ColG s3b domain

<400> SEQUENCE: 27

```
Ile Lys Glu Val Glu Asn Asn Asn Asp Phe Asp Lys Ala Met Lys Val
1               5                   10                  15

Asp Ser Asn Ser Lys Ile Val Gly Thr Leu Ser Asn Asp Asp Leu Lys
            20                  25                  30

Asp Ile Tyr Ser Ile Asp Ile Gln Asn Pro Ser Asp Leu Asn Ile Val
        35                  40                  45

Val Glu Asn Leu Asp Asn Ile Lys Met Asn Trp Leu Leu Tyr Ser Ala
    50                  55                  60

Asp Asp Leu Ser Asn Tyr Val Asp Tyr Ala Asn Ala Asp Gly Asn Lys
65                  70                  75                  80

Leu Ser Asn Thr Cys Lys Leu Asn Pro Gly Lys Tyr Tyr Leu Cys Val
                85                  90                  95

Tyr Gln Phe Glu Asn Ser Gly Thr Gly Asn Tyr Ile Val Asn Leu Gln
            100                 105                 110

Asn Lys
```

<210> SEQ ID NO 28
<211> LENGTH: 115
<212> TYPE: PRT
<213> ORGANISM: B. brevis
<220> FEATURE:
<221> NAME/KEY: misc_feature
<222> LOCATION: (1)..(115)
<223> OTHER INFORMATION: ColG s3b domain

```
<400> SEQUENCE: 28

Tyr Gln Glu Asn Glu Ser Asn Asp Ser Thr Glu Gln Ala Asn Gly Pro
1 5 10 15

Leu Lys Ile Gly Thr Thr Val Ser Gly Asp Met Lys Gly Asn Asp Trp
20 25 30

Gln Asp Ile Phe Ala Phe Gln Val Asp Lys Pro Glu Glu Ile Arg Ile
35 40 45

Ser Leu Asn Pro Gln Glu Gly Gln Gly Val Thr Trp Met Leu Phe His
50 55 60

Glu Gly Asn Leu Asp Gln Pro Val Thr Tyr Pro Gln Glu Arg Glu Gly
65 70 75 80

Asn Leu Gln Ser Ala His Tyr Gln Val Lys Pro Gly Arg Tyr Phe Leu
85 90 95

Tyr Val Tyr Lys Tyr Gln Asn Glu Asp Ile Val Tyr Thr Val Glu Thr
100 105 110

Lys Gln Arg
115

<210> SEQ ID NO 29
<211> LENGTH: 114
<212> TYPE: PRT
<213> ORGANISM: P. dendritiformis
<220> FEATURE:
<221> NAME/KEY: misc_feature
<222> LOCATION: (1)..(114)
<223> OTHER INFORMATION: ColG s3b domain

<400> SEQUENCE: 29

Phe Glu Glu Thr Glu Pro Asn Asp Thr Pro Glu Thr Ala Asn Gly Pro
1 5 10 15

Ile Pro Ala Gly Arg Pro Val Val Gly Thr Leu Asn Gly Ser Asp Lys
20 25 30

Gln Asp Val Phe Ile Ile Asp Val Asp Gln Pro Ala Glu Leu Gln Ile
35 40 45

Glu Leu Glu Arg Arg Leu Gly Ser Gly Val Asn Trp Ile Leu Tyr Arg
50 55 60

Glu Gly Asp Thr Asp Arg Pro Leu Leu Tyr Pro Ser Glu Val Glu Gly
65 70 75 80

Asn Arg Met Ser Gly Gly Phe Ala Ala Glu Ala Gly Arg Tyr His Leu
85 90 95

Tyr Val Tyr Lys Tyr Thr Asp Glu Asp Ile His Tyr Thr Leu Gln Val
100 105 110

Gln His

<210> SEQ ID NO 30
<211> LENGTH: 115
<212> TYPE: PRT
<213> ORGANISM: C. sordellii
<220> FEATURE:
<221> NAME/KEY: misc_feature
<222> LOCATION: (1)..(115)
<223> OTHER INFORMATION: ColG s3b domain

<400> SEQUENCE: 30

Gly Val Glu Gln Glu Asp Asn Asn Ser Phe Glu Lys Ala Asn Pro Phe
1 5 10 15

Ser Ile Asn Gln Leu Val Lys Gly Glu Leu Asp Asn Asn Lys Asp Thr
20 25 30

```
Ser Asp Tyr Phe Lys Phe Glu Val Lys Glu Asp Ala Gln Leu Asn Ile
            35                  40                  45

Ser Leu Glu Lys Thr Gly Asp Gly Val Asn Trp Leu Leu Phe Lys
 50                  55                  60

Asp Ser Asp Leu Glu Asn Tyr Ile Ala Ser Pro Thr Glu Ser Ile Asp
 65                  70                  75                  80

Asn Lys Leu Asn Gly Lys Val Asp Leu Lys Val Gly Thr Tyr Tyr Leu
                85                  90                  95

Glu Val Tyr Gly Tyr Gly Ser Ser Pro Val Lys Tyr Asn Phe Lys Val
                100                 105                 110

Thr Pro Asn
       115
```

<210> SEQ ID NO 31
<211> LENGTH: 111
<212> TYPE: PRT
<213> ORGANISM: C. sporogenes
<220> FEATURE:
<221> NAME/KEY: misc_feature
<222> LOCATION: (1)..(111)
<223> OTHER INFORMATION: ColG s3c domain

<400> SEQUENCE: 31

```
Ile His Glu Lys Glu Asn Asn Asp Ser Phe Glu Ser Ala Asn Lys Ile
 1                   5                  10                  15

Val Leu Asn Ala Pro Ile Leu Gly Ser Leu Asn Gly Glu Asp Leu Arg
                20                  25                  30

Asp Ile Tyr Ser Phe Glu Ile Lys Glu Thr Lys Asp Leu Asn Ile Lys
            35                  40                  45

Leu Thr Asn Leu Asn Asn Leu Gly Leu Thr Trp Thr Leu Tyr Lys Glu
 50                  55                  60

Ser Asp Leu Asn Asn Tyr Ile Ala Tyr Gly Ser Lys Leu Gly Ser Thr
 65                  70                  75                  80

Ile Val Gly Asn Cys His Val Thr Pro Gly Lys Tyr Tyr Leu Tyr Val
                85                  90                  95

Tyr Lys Tyr Ser Gly Asn Asn Gly Asn Tyr Ser Leu Ile Ile Lys
                100                 105                 110
```

<210> SEQ ID NO 32
<211> LENGTH: 111
<212> TYPE: PRT
<213> ORGANISM: C. botulinum
<220> FEATURE:
<221> NAME/KEY: misc_feature
<222> LOCATION: (1)..(111)
<223> OTHER INFORMATION: C. botulinumA3 ColG s3c domain

<400> SEQUENCE: 32

```
Ile Tyr Glu Lys Glu Asn Asn Asp Ser Phe Glu Thr Ala Asn Lys Ile
 1                   5                  10                  15

Met Leu Asn Thr Thr Val Leu Gly Asn Leu Asn Gly Lys Asp Val Arg
                20                  25                  30

Asp Ile Tyr Ser Phe Asp Ile Lys Glu Ala Lys Asp Leu Asp Ile Lys
            35                  40                  45

Leu Asn Asn Leu Asn Asn Gly Leu Ala Trp Asn Leu Tyr Lys Glu
 50                  55                  60

Ser Asp Leu Asn Asn Tyr Ile Ala Tyr Gly Ser Val Ser Gly Asn Thr
 65                  70                  75                  80

Ile Lys Gly Lys Cys Asn Val Ala Pro Gly Lys Tyr Tyr Leu Tyr Val
```

```
                    85                  90                  95

Tyr Lys Tyr Ser Gly Asp Asn Gly Asn Tyr Ser Leu Ala Ile Lys
                100                 105                 110

<210> SEQ ID NO 33
<211> LENGTH: 111
<212> TYPE: PRT
<213> ORGANISM: B. cereus
<220> FEATURE:
<221> NAME/K
<223> OTHER INFORMATION: G9842 domain

<400> SEQUENCE: 35

Val Thr Glu Asn Glu Pro Asn Asn Glu Pro Arg Gln Ala Asn Lys Val
1               5                   10                  15

Asn Phe His Thr Pro Val Lys Gly Thr Leu His Asn Ser Asp Arg Val
            20                  25                  30

Asp Val Phe Thr Phe Gln Ile Asp Ser Pro Glu Asn Ile Asn Ile Ser
        35                  40                  45

Leu Leu Asn Glu Gln Asn Ile Gly Met Thr Trp Val Leu His His Glu
50                  55                  60

Ser Asp Leu Asn Asn Tyr Val Ala Tyr Gly Glu Asn Glu Gly Asn Val
65                  70                  75                  80

Val Lys Gly Thr Tyr Asn Ala Lys Pro Gly Lys Tyr Tyr Leu Tyr Val
                85                  90                  95

Tyr Lys Tyr Glu Asn Lys Asp Gly Ser Tyr Val Leu Asn Ile Lys
            100                 105                 110

<210> SEQ ID NO 36
<211> LENGTH: 111
<212> TYPE: PRT
<213> ORGANISM: B. mycoides
<220> FEATURE:
<221> NAME/KEY: misc_feature
<222> LOCATION: (1)..(111)
<223> OTHER INFORMATION: ColG domain

<400> SEQUENCE: 36

Ser Val Glu Lys Glu Pro Asn Asn Ser Phe Gln Thr Ala Asn Lys Leu
1               5                   10                  15

Gln Leu Asn Gln Leu Leu Arg Ala Ser Leu Gly Asn Gly Asp Thr Ser
            20                  25                  30

Asp Tyr Phe Glu Ile Asn Val Glu Thr Ala Arg Asn Leu Gln Ile Asn
        35                  40                  45

Val Thr Lys Glu Asn Asn Ile Gly Val Asn Trp Val Leu Tyr Ser Ala
50                  55                  60

Ala Asp Leu Asn Asn Tyr Val Thr Tyr Ala Gln Thr Gln Gly Asn Lys
65                  70                  75                  80

Leu Val Gly Ser Tyr Asn Ala His Pro Gly Lys Tyr Tyr Leu His Val
                85                  90                  95

Tyr Gln Tyr Gly Gly Gly Thr Gly Asn Tyr Thr Val Glu Val Lys
            100                 105                 110

<210> SEQ ID NO 37
<211> LENGTH: 112
<212> TYPE: PRT
<213> ORGANISM: B. weihensteph
<220> FEATURE:
<221> NAME/KEY: misc_feature
<222> LOCATION: (1)..(112)
<223> OTHER INFORMATION: ColG domain

<400> SEQUENCE: 37

Ala Val Glu Lys Glu Pro Asn Asn Ser Phe Asp Ala Ala Asn Pro Leu
1               5                   10                  15

Ser Leu Asn Ala Leu Leu Arg Gly Asn Leu Ser Asp Gln Asp Gln Val
            20                  25                  30

Asp Arg Phe Val Ile Asp Val Lys Asp Pro Lys Asp Leu Gln Ile Thr
        35                  40                  45

Val Thr Asn Glu Gln Asn Leu Gly Leu Asn Trp Val Leu Tyr Ser Glu
 50                  55                  60

Ser Asp Leu Asn Asn Tyr Val Thr Tyr Ala Thr Lys Arg Asp Gly Asn
 65                  70                  75                  80

Lys Leu Leu Gly Asn Tyr Asn Ala Lys Pro Gly Lys Tyr Tyr Leu Ser
                 85                  90                  95

Val Tyr Lys Tyr Gly Gly Gly Thr Gly Asn Phe Thr Val Glu Val Lys
            100                 105                 110

<210> SEQ ID NO 38
<211> LENGTH: 125
<212> TYPE: PRT
<213> ORGANISM: Clostridium histolyticum
<220> FEATURE:
<221> NAME/KEY: misc_feature
<222> LOCATION: (1)..(125)
<223> OTHER INFORMATION: ColH s3 domain

<400> SEQUENCE: 38

Gly Ile Asn Ser Pro Val Tyr Pro Ile Gly Thr Glu Lys Glu Pro Asn
 1                5                  10                  15

Asn Ser Lys Glu Thr Ala Ser Gly Pro Ile Val Pro Gly Ile Pro Val
                 20                  25                  30

Ser Gly Thr Ile Glu Asn Thr Ser Asp Gln Asp Tyr Phe Tyr Phe Asp
             35                  40                  45

Val Ile Thr Pro Gly Glu Val Lys Ile Asp Ile Asn Lys Leu Gly Tyr
 50                  55                  60

Gly Gly Ala Thr Trp Val Val Tyr Asp Glu Asn Asn Asn Ala Val Ser
 65                  70                  75                  80

Tyr Ala Thr Asp Asp Gly Gln Asn Leu Ser Gly Lys Phe Lys Ala Asp
                 85                  90                  95

Lys Pro Gly Arg Tyr Tyr Ile His Leu Tyr Met Phe Asn Gly Ser Tyr
            100                 105                 110

Met Pro Tyr Arg Ile Asn Ile Glu Gly Ser Val Gly Arg
            115                 120                 125

<210> SEQ ID NO 39
<211> LENGTH: 111
<212> TYPE: PRT
<213> ORGANISM: Clostridium histolyticum
<220> FEATURE:
<221> NAME/KEY: misc_feature
<222> LOCATION: (1)..(111)
<223> OTHER INFORMATION: ColH s3 domain

<400> SEQUENCE: 39

Gly Thr Glu Lys Glu Pro Asn Asn Ser Lys Glu Thr Ala Ser Gly Pro
 1                5                  10                  15

Ile Val Pro Gly Ile Pro Val Ser Gly Thr Ile Glu Asn Thr Ser Asp
                 20                  25                  30

Gln Asp Tyr Phe Tyr Phe Asp Val Ile Thr Pro Gly Glu Val Lys Ile
             35                  40                  45

Asp Ile Asn Lys Leu Gly Tyr Gly Gly Ala Thr Trp Val Val Tyr Asp
 50                  55                  60

Glu Asn Asn Asn Ala Val Ser Tyr Ala Thr Asp Asp Gly Gln Asn Leu
 65                  70                  75                  80

Ser Gly Lys Phe Lys Ala Asp Lys Pro Gly Arg Tyr Tyr Ile His Leu
                 85                  90                  95

Tyr Met Phe Asn Gly Ser Tyr Met Pro Tyr Arg Ile Asn Ile Glu

-continued

```
                  100                 105                 110

<210> SEQ ID NO 40
<211> LENGTH: 234
<212> TYPE: PRT
<213> ORGANISM: C. histolyticum
<220> FEATURE:
<221> NAME/KEY: misc_feature
<222> LOCATION: (1)..(234)
<223> OTHER INFORMATION: ColG s3a + s3b domains

<400> SEQUENCE: 40

Thr Pro Ile Thr Lys Glu Met Glu Pro Asn Asp Asp Ile Lys Glu Ala
1               5                   10                  15

Asn Gly Pro Ile Val Glu Gly Val Thr Val Lys Gly Asp Leu Asn Gly
            20                  25                  30

Ser Asp Asp Ala Asp Thr Phe Tyr Phe Asp Val Lys Glu Asp Gly Asp
        35                  40                  45

Val Thr Ile Glu Leu Pro Tyr Ser Gly Ser Ser Asn Phe Thr Trp Leu
50                  55                  60

Val Tyr Lys Glu Gly Asp Asp Gln Asn His Ile Ala Ser Gly Ile Asp
65                  70                  75                  80

Lys Asn Asn Ser Lys Val Gly Thr Phe Lys Ser Thr Lys Gly Arg His
                85                  90                  95

Tyr Val Phe Ile Tyr Lys His Asp Ser Ala Ser Asn Ile Ser Tyr Ser
            100                 105                 110

Leu Asn Ile Lys Gly Leu Gly Asn Glu Lys Leu Lys Glu Lys Glu Asn
        115                 120                 125

Asn Asp Ser Ser Asp Lys Ala Thr Val Ile Pro Asn Phe Asn Thr Thr
    130                 135                 140

Met Gln Gly Ser Leu Leu Gly Asp Asp Ser Arg Asp Tyr Tyr Ser Phe
145                 150                 155                 160

Glu Val Lys Glu Glu Gly Glu Val Asn Ile Glu Leu Asp Lys Lys Asp
                165                 170                 175

Glu Phe Gly Val Thr Trp Thr Leu His Pro Glu Ser Asn Ile Asn Asp
            180                 185                 190

Arg Ile Thr Tyr Gly Gln Val Asp Gly Asn Lys Val Ser Asn Lys Val
        195                 200                 205

Lys Leu Arg Pro Gly Lys Tyr Tyr Leu Leu Val Tyr Lys Tyr Ser Gly
    210                 215                 220

Ser Gly Asn Tyr Glu Leu Arg Val Asn Lys
225                 230

<210> SEQ ID NO 41
<211> LENGTH: 239
<212> TYPE: PRT
<213> ORGANISM: C. sporogenes
<220> FEATURE:
<221> NAME/KEY: misc_feature
<222> LOCATION: (1)..(239)
<223> OTHER INFORMATION: ColG s3a + s3b domains

<400> SEQUENCE: 41

Leu Val Ile Ser Glu Lys Glu Asp Asn Asp Ser Phe Asp Lys Ala Asn
1               5                   10                  15

Arg Val Cys Lys Asn Gln Ser Val Leu Ala Thr Leu Asp Thr Asn Asp
            20                  25                  30

Asn Arg Asp Thr Tyr Tyr Phe Asp Ala Leu Thr Ala Gly Thr Ile Asp
        35                  40                  45
```

```
Val Ile Met Glu Asn Thr Asp Asn Asn Ser Asn Ile Phe Asn Trp Leu
 50                  55                  60

Ala Tyr Ser Ser Asp Asn Thr Asn Asn Tyr Ile Gly Tyr Ser Thr Lys
 65                  70                  75                  80

Lys Glu Gly Asn Lys Leu Leu Gly Ser Phe Lys Val Pro Lys Pro Gly
                 85                  90                  95

Arg Tyr Tyr Ile Leu Ala Tyr Lys Asn Ser Ser Asn Lys Ile Asn Tyr
                100                 105                 110

Lys Leu Thr Ile Asn Gly Asp Ile Asp Lys Ala Pro Leu Lys Asn Glu
                115                 120                 125

Ile His Glu Lys Glu Asn Asn Asp Ser Phe Glu Ser Ala Asn Lys Ile
                130                 135                 140

Val Pro Asp Ala Pro Val Leu Gly Ser Leu Asn Gly Glu Asp Leu Arg
145                 150                 155                 160

Asp Ile Tyr Ser Phe Asp Ile Lys Glu Thr Lys Asp Leu Asn Ile Lys
                165                 170                 175

Leu Thr Asn Leu Asn Asn Leu Gly Leu Thr Trp Thr Leu Tyr Lys Glu
                180                 185                 190

Ser Asp Leu Thr Asn Tyr Ile Ala Tyr Gly Ser Lys Leu Gly Asn Thr
                195                 200                 205

Ile Val Gly Asn Cys His Val Thr Pro Gly Lys Tyr Tyr Leu Tyr Val
210                 215                 220

Tyr Lys Tyr Ser Gly Asn Ser Gly Asn Tyr Ser Leu Ile Ile Lys
225                 230                 235

<210> SEQ ID NO 42
<211> LENGTH: 244
<212> TYPE: PRT
<213> ORGANISM: C. botulinum
<220> FEATURE:
<221> NAME/KEY: misc_feature
<222> LOCATION: (1)..(244)
<223> OTHER INFORMATION: C. botulinumB ColG s3a + s3b domains

<400> SEQUENCE: 42

Ile Asn Val Asp Glu Glu Glu Tyr Asn Asp Asp Phe Glu Cys Ala Asn
 1               5                  10                  15

Asn Ile Phe Lys Asn Gln Ile Met Ser Gly Asn Leu Asp Ser Ser Asp
                20                  25                  30

Lys Cys Asp Thr Phe Ser Phe Asn Ala Leu Ser Ala Gly Thr Ile Asn
                35                  40                  45

Val Thr Leu Glu Asn Ser Asn Ser Asp Ser Ser Thr Val Asn Trp Leu
 50                  55                  60

Ala Tyr Ser Ser Glu Asp Thr Asp Asn Tyr Ile Gly Tyr Ala Ser Glu
 65                  70                  75                  80

Asn Asp Gly Asn Lys Phe Ser Gly Lys Phe Lys Val Asn Lys Pro Gly
                 85                  90                  95

Lys Tyr Tyr Ile Val Ala Tyr Glu Val Asn Gly Ala Asp Ser Lys Tyr
                100                 105                 110

Lys Leu Lys Val Asp Gly Asp Ile Glu Asn Thr Ser Glu Ser Lys Pro
                115                 120                 125

Glu Asp Lys Glu Glu Ile Lys Glu Glu Ile Asn Asp Asp Ser Phe Asp
                130                 135                 140

Ser Ala Thr Lys Ile Lys Ala Asn Ser Thr Ile Thr Asp Thr Leu Asn
145                 150                 155                 160
```

Gly Glu Asp Asn Lys Asp Ile Cys Tyr Phe Asn Val Asn Asn Ser
                165                 170                 175

Asp Leu Asn Ile Glu Leu Asn Ser Leu Thr Asn Leu Gly Val Ala Trp
                180                 185                 190

Gln Leu Phe Ser Glu Glu Asp Leu Asp Asn Tyr Ile Ala Tyr Gly Ser
            195                 200                 205

Gln Ser Gly Asp Ser Ile Val Gly Thr Ala Asn Val Gln Pro Gly Lys
            210                 215                 220

Tyr Tyr Leu Leu Ile Tyr Lys Tyr Thr Gln Ala Asp Gly Ser Tyr Thr
225                 230                 235                 240

Phe Thr Ile Lys

<210> SEQ ID NO 43
<211> LENGTH: 239
<212> TYPE: PRT
<213> ORGANISM: C. tetani E88
<220> FEATURE:
<221> NAME/KEY: misc_feature
<222> LOCATION: (1)..(239)
<223> OTHER INFORMATION: ColG s3a + s3b domains

<400> SEQUENCE: 43

Asn Val Ile Tyr Glu Lys Glu Asn Asn Asp Ser Phe Asp Lys Ala Asn
1               5                   10                  15

Lys Ile His Lys Asn Gln Ile Val Met Ala Thr Leu Asp Thr Glu Asp
                20                  25                  30

Tyr Arg Asp Thr Phe Tyr Phe Asp Ala Leu Thr Ser Gly Ser Ile Asp
            35                  40                  45

Ile Thr Ile Glu Asn Ile His Gly Asn Ser Asp Ala Phe Asn Trp Leu
50                  55                  60

Val Tyr Asn Asp Glu Asp Leu Asn Tyr Ile Ala Tyr Pro Thr Lys
65                  70                  75                  80

Lys Glu Asp Asn Lys Leu Met Gly Ser Phe Lys Val His Lys Pro Gly
                85                  90                  95

Arg Tyr Tyr Ile Leu Val Tyr Lys Thr Ser Leu Asn Lys Val Asn Tyr
            100                 105                 110

Lys Leu Asn Ile Ser Asp Ala Thr Asn Met Ala Pro Val Ile Lys Lys
        115                 120                 125

Ile His Glu Lys Glu Asn Asn Asp Ser Phe Glu Thr Ala Asn Lys Ile
    130                 135                 140

Thr Leu Asp Thr Leu Val Leu Gly Asn Leu Asp Tyr Lys Asp Val Ser
145                 150                 155                 160

Asp Ile Tyr Ser Phe Asp Ile Glu Asn Thr Lys Asp Leu Asn Ile Lys
                165                 170                 175

Leu Thr Asn Leu Asn Asn Leu Gly Ile Ala Trp Asn Leu Tyr Lys Glu
            180                 185                 190

Ser Asp Leu Asn Asn Tyr Ile Ala Tyr Gly Ala Lys Ser Asp Asn Ala
            195                 200                 205

Ile Val Gly Lys Cys Asn Leu Ser Pro Gly Lys Tyr Tyr Leu Tyr Val
        210                 215                 220

Tyr Lys Tyr Ser Gly Asp Lys Gly Asn Tyr Ser Val Ile Ile Asn
225                 230                 235

<210> SEQ ID NO 44
<211> LENGTH: 243
<212> TYPE: PRT
<213> ORGANISM: C. perfringens

```
<220> FEATURE:
<221> NAME/KEY: misc_feature
<222> LOCATION: (1)..(243)
<223> OTHER INFORMATION: ColG s3a + s3b domains

<400> SEQUENCE: 44
```

Glu Val Ile Asn Glu Ser Glu Pro Asn Asn Asp Phe Glu Lys Ala Asn
1               5                   10                  15

Gln Ile Ala Lys Ser Asn Met Leu Val Lys Gly Thr Leu Ser Glu Glu
            20                  25                  30

Asp Tyr Ser Asp Lys Tyr Tyr Phe Asp Val Ala Lys Lys Gly Asn Val
        35                  40                  45

Lys Ile Thr Leu Asn Asn Leu Asn Ser Val Gly Ile Thr Trp Thr Leu
    50                  55                  60

Tyr Lys Glu Gly Asp Leu Asn Asn Tyr Val Leu Tyr Ala Thr Gly Asn
65                  70                  75                  80

Asp Gly Thr Val Leu Lys Gly Glu Lys Thr Leu Glu Pro Gly Arg Tyr
            85                  90                  95

Tyr Leu Ser Val Tyr Thr Tyr Asp Asn Gln Ser Gly Thr Tyr Thr Val
        100                 105                 110

Asn Val Lys Gly Asn Leu Lys Asn Glu Val Lys Glu Thr Ala Lys Asp
    115                 120                 125

Ala Ile Lys Glu Val Glu Asn Asn Asn Asp Phe Asp Lys Ala Met Lys
130                 135                 140

Val Asp Ser Asn Ser Lys Ile Val Gly Thr Leu Ser Asn Asp Asp Leu
145                 150                 155                 160

Lys Asp Ile Tyr Ser Ile Asp Ile Gln Asn Pro Ser Asp Leu Asn Ile
                165                 170                 175

Val Val Glu Asn Leu Asp Asn Ile Lys Met Asn Trp Leu Leu Tyr Ser
            180                 185                 190

Ala Asp Asp Leu Ser Asn Tyr Val Asp Tyr Ala Asn Ala Asp Gly Asn
        195                 200                 205

Lys Leu Ser Asn Thr Cys Lys Leu Asn Pro Gly Lys Tyr Tyr Leu Cys
    210                 215                 220

Val Tyr Gln Phe Glu Asn Ser Gly Thr Gly Asn Tyr Ile Val Asn Leu
225                 230                 235                 240

Gln Asn Lys

```
<210> SEQ ID NO 45
<211> LENGTH: 239
<212> TYPE: PRT
<213> ORGANISM: B. brevis
<220> FEATURE:
<221> NAME/KEY: misc_feature
<222> LOCATION: (1)..(239)
<223> OTHER INFORMATION: ColG s3a + s3b domains

<400> SEQUENCE: 45
```

Asp Gly Ser Glu Thr Glu Gln Pro Asn Pro Asn Pro Glu Glu Ser Ser
1               5                   10                  15

Leu Ser Leu Gly Lys Pro Ile Thr Gly Ile Ile His Pro Gln Lys Pro
            20                  25                  30

Ser Gln Glu Phe Arg Leu Asp Val Lys Ser Ala Gln Gln Leu Gln Val
        35                  40                  45

Glu Met Glu Thr Lys Gln Gly Asp Gly Val Ala Trp Leu Val Phe His
    50                  55                  60

Glu Ala Asp Arg Glu Asn Tyr Ile Ser Tyr Pro Thr Lys Arg Glu Gly

```
            65                  70                  75                  80
        Asn Lys Leu Ile Gly Ser Phe Asp Ala Lys Pro Gly Thr Tyr Tyr Val
                            85                  90                  95

Thr Ala Tyr Thr Tyr Arg Thr Glu Gln Glu Asp Gln Pro Phe Arg Leu
                        100                 105                 110

Leu Val Thr Gly Glu Asp Arg Pro Gln Glu Gln Leu Tyr Gln Glu Asn
                        115                 120                 125

Glu Ser Asn Asp Ser Thr Glu Gln Ala Asn Gly Pro Leu Lys Ile Gly
                    130                 135                 140

Thr Thr Val Ser Gly Asp Met Lys Gly Asn Asp Trp Gln Asp Ile Phe
        145                 150                 155                 160

Ala Phe Gln Val Asp Lys Pro Glu Glu Ile Arg Ile Ser Leu Asn Pro
                        165                 170                 175

Gln Glu Gly Gln Gly Val Thr Trp Met Leu Phe His Glu Gly Asn Leu
                    180                 185                 190

Asp Gln Pro Val Thr Tyr Pro Gln Arg Glu Gly Asn Leu Gln Ser
                    195                 200                 205

Ala His Tyr Gln Val Lys Pro Gly Arg Tyr Phe Leu Tyr Val Tyr Lys
                    210                 215                 220

Tyr Gln Asn Glu Asp Ile Val Tyr Thr Val Glu Thr Lys Gln Arg
        225                 230                 235

<210> SEQ ID NO 46
<211> LENGTH: 242
<212> TYPE: PRT
<213> ORGANISM: P. dendritiformis
<220> FEATURE:
<221> NAME/KEY: misc_feature
<222> LOCATION: (1)..(242)
<223> OTHER INFORMATION: ColG s3a + s3b domains

<400> SEQUENCE: 46

Pro Asn Ala Asp His Glu Pro Asn Asp Ser Trp Glu Gln Ala Val Pro
        1               5                   10                  15

Leu Asp Gly Thr Gly Val Pro Val Ser Gly Lys Leu Ser Asp Thr Asp
                        20                  25                  30

Arg Val Asp Val Tyr Arg Phe Asp Ala Gly Lys Ala Glu Gln Trp Thr
                    35                  40                  45

Ile Glu Leu Glu Thr Glu Gln Ala Gln Ser Val Ala Trp Val Val His
                50                  55                  60

His Glu Ser Asp Leu Asn Asn Tyr Ala Ala Tyr Pro Thr Gln Val Glu
        65                  70                  75                  80

Gly Thr Ser Val Ala Gly Ser Val Asp Ala Val Pro Gly Thr Tyr Tyr
                        85                  90                  95

Val Tyr Val Tyr Ser Val Gly Asn Gly Glu Gln Ser Tyr Arg Leu Val
                        100                 105                 110

Val Gln Pro Gly Thr Thr Gly Gln Glu Gln Glu Pro Glu Leu Pro Pro
                    115                 120                 125

Phe Glu Glu Thr Glu Pro Asn Asp Thr Pro Glu Thr Ala Asn Gly Pro
                    130                 135                 140

Ile Pro Ala Gly Arg Pro Val Val Gly Thr Leu Asn Gly Ser Asp Lys
        145                 150                 155                 160

Gln Asp Val Phe Ile Ile Asp Val Asp Gln Pro Ala Glu Leu Gln Ile
                        165                 170                 175

Glu Leu Glu Arg Arg Leu Gly Ser Gly Val Asn Trp Ile Leu Tyr Arg
                    180                 185                 190
```

Glu Gly Asp Thr Asp Arg Pro Leu Leu Tyr Pro Ser Glu Val Glu Gly
        195                 200                 205

Asn Arg Met Ser Gly Gly Phe Ala Ala Glu Ala Gly Arg Tyr His Leu
    210                 215                 220

Tyr Val Tyr Lys Tyr Thr Asp Glu Asp Ile His Tyr Thr Leu Gln Val
225                 230                 235                 240

Gln His

<210> SEQ ID NO 47
<211> LENGTH: 238
<212> TYPE: PRT
<213> ORGANISM: C. sordellii
<220> FEATURE:
<221> NAME/KEY: misc_feature
<222> LOCATION: (1)..(238)
<223> OTHER INFORMATION: ColG s3a + s3b domains

<400> SEQUENCE: 47

Pro Lys Gly Ser Gln Glu Val Gly Asn Asp Asp Thr Phe Glu Thr Ala
1               5                   10                  15

Asn Gly Pro Ile Lys Ile Asn Thr Asn Tyr Ser Gly Asp Leu Ser Asp
            20                  25                  30

Thr Asp Asn Lys Asp Tyr Tyr Phe Asn Leu Asp Asn Pro Ser Asn
        35                  40                  45

Ile Asn Ile Thr Leu Glu Asn Leu Asp Asn Lys Gly Ile Ser Trp Gln
    50                  55                  60

Leu Phe His Glu Ser Asp Leu Asn Asn Tyr Val Ala Tyr Pro Thr Thr
65                  70                  75                  80

Ser Gly Ala Ile Leu Asn Gly Asp Tyr Asn Ala Thr Lys Pro Gly Lys
                85                  90                  95

Tyr Tyr Ile Leu Val Tyr Asn His Asp Lys Ser Ile Ala Asn Tyr Asn
            100                 105                 110

Leu Lys Val Asn Phe Gly Asn Asn Asn Asp Gly Val Glu Gln Glu
        115                 120                 125

Asp Asn Asn Ser Phe Glu Lys Ala Asn Pro Phe Ser Ile Asn Gln Leu
130                 135                 140

Val Lys Gly Glu Leu Asp Asn Asn Lys Asp Thr Ser Asp Tyr Phe Lys
145                 150                 155                 160

Phe Glu Val Lys Glu Asp Ala Gln Leu Asn Ile Ser Leu Glu Lys Thr
                165                 170                 175

Glu Gly Asp Gly Val Asn Trp Leu Leu Phe Lys Asp Ser Asp Leu Glu
            180                 185                 190

Asn Tyr Ile Ala Ser Pro Thr Glu Ser Ile Asp Asn Lys Leu Asn Gly
        195                 200                 205

Lys Val Asp Leu Lys Val Gly Thr Tyr Tyr Leu Glu Val Tyr Gly Tyr
    210                 215                 220

Gly Ser Ser Pro Val Lys Tyr Asn Phe Lys Val Thr Pro Asn
225                 230                 235

<210> SEQ ID NO 48
<211> LENGTH: 6
<212> TYPE: PRT
<213> ORGANISM: Clostridium histolyticum
<220> FEATURE:
<221> NAME/KEY: misc_feature
<222> LOCATION: (1)..(6)
<223> OTHER INFORMATION: ColG domain linker

```
<400> SEQUENCE: 48

Gly Leu Gly Asn Glu Lys
1               5

<210> SEQ ID NO 49
<211> LENGTH: 11
<212> TYPE: PRT
<213> ORGANISM: C. sporogenes
<220> FEATURE:
<221> NAME/KEY: misc_feature
<222> LOCATION: (1)..(11)
<223> OTHER INFORMATION: ColG domain linker

<400> SEQUENCE: 49

Gly Asp Ile Asp Lys Ala Pro Leu Lys Asn Glu
1               5                   10

<210> SEQ ID NO 50
<211> LENGTH: 16
<212> TYPE: PRT
<213> ORGANISM: C. botulinumB
<220> FEATURE:
<221> NAME/KEY: misc_feature
<222> LOCATION: (1)..(16)
<223> OTHER INFORMATION: C. botulinumB ColG domain linker

<400> SEQUENCE: 50

Gly Asp Ile Glu Asn Thr Ser Glu Ser Lys Pro Glu Asp Lys Glu Glu
1               5                   10                  15

<210> SEQ ID NO 51
<211> LENGTH: 11
<212> TYPE: PRT
<213> ORGANISM: C. tetani E88
<220> FEATURE:
<221> NAME/KEY: misc_feature
<222> LOCATION: (1)..(11)
<223> OTHER INFORMATION: ColG domain linker

<400> SEQUENCE: 51

Asp Ala Thr Asn Met Ala Pro Val Ile Lys Lys
1               5                   10

<210> SEQ ID NO 52
<211> LENGTH: 14
<212> TYPE: PRT
<213> ORGANISM: C. perfringens
<220> FEATURE:
<221> NAME/KEY: misc_feature
<222> LOCATION: (1)..(14)
<223> OTHER INFORMATION: ColG domain linker

<400> SEQUENCE: 52

Gly Asn Leu Lys Asn Glu Val Lys Glu Thr Ala Lys Asp Ala
1               5                   10

<210> SEQ ID NO 53
<211> LENGTH: 9
<212> TYPE: PRT
<213> ORGANISM: B. brevis
<220> FEATURE:
<221> NAME/KEY: misc_feature
<222> LOCATION: (1)..(9)
<223> OTHER INFORMATION: ColG domain linker

<400> SEQUENCE: 53

Gly Glu Asp Arg Pro Gln Glu Gln Leu
1               5
```

<210> SEQ ID NO 54
<211> LENGTH: 14
<212> TYPE: PRT
<213> ORGANISM: P. dendritiformis
<220> FEATURE:
<221> NAME/KEY: misc_feature
<222> LOCATION: (1)..(14)
<223> OTHER INFORMATION: ColG domain linker

<400> SEQUENCE: 54

Pro Gly Thr Thr Gly Gln Glu Gln Glu Pro Glu Leu Pro Pro
1               5                   10

<210> SEQ ID NO 55
<211> LENGTH: 7
<212> TYPE: PRT
<213> ORGANISM: C. sordellii
<220> FEATURE:
<221> NAME/KEY: misc_feature
<222> LOCATION: (1)..(7)
<223> OTHER INFORMATION: ColG domain linker

<400> SEQUENCE: 55

Phe Gly Asn Asn Asn Asp Asp
1               5

<210> SEQ ID NO 56
<211> LENGTH: 288
<212> TYPE: PRT
<213> ORGANISM: Homo sapiens
<220> FEATURE:
<221> NAME/KEY: misc_feature
<222> LOCATION: (1)..(288)
<223> OTHER INFORMATION: Human bFGF protein sequence

<400> SEQUENCE: 56

Met Val Gly Val Gly Gly Gly Asp Val Glu Asp Val Thr Pro Arg Pro
1               5                   10                  15

Gly Gly Cys Gln Ile Ser Gly Arg Gly Ala Arg Gly Cys Asn Gly Ile
            20                  25                  30

Pro Gly Ala Ala Ala Trp Glu Ala Ala Leu Pro Arg Arg Arg Pro Arg
        35                  40                  45

Arg His Pro Ser Val Asn Pro Arg Ser Arg Ala Ala Gly Ser Pro Arg
    50                  55                  60

Thr Arg Gly Arg Arg Thr Glu Glu Arg Pro Ser Gly Ser Arg Leu Gly
65                  70                  75                  80

Asp Arg Gly Arg Gly Arg Ala Leu Pro Gly Gly Arg Leu Gly Gly Arg
                85                  90                  95

Gly Arg Gly Arg Ala Pro Glu Arg Val Gly Gly Arg Gly Arg Gly Arg
            100                 105                 110

Gly Thr Ala Ala Pro Arg Ala Ala Pro Ala Ala Arg Gly Ser Arg Pro
        115                 120                 125

Gly Pro Ala Gly Thr Met Ala Ala Gly Ser Ile Thr Thr Leu Pro Ala
    130                 135                 140

Leu Pro Glu Asp Gly Gly Ser Gly Ala Phe Pro Pro Gly His Phe Lys
145                 150                 155                 160

Asp Pro Lys Arg Leu Tyr Cys Lys Asn Gly Gly Phe Phe Leu Arg Ile
                165                 170                 175

His Pro Asp Gly Arg Val Asp Gly Val Arg Glu Lys Ser Asp Pro His
            180                 185                 190

```
Ile Lys Leu Gln Leu Gln Ala Glu Glu Arg Gly Val Val Ser Ile Lys
        195                 200                 205

Gly Val Cys Ala Asn Arg Tyr Leu Ala Met Lys Glu Asp Gly Arg Leu
        210                 215                 220

Leu Ala Ser Lys Cys Val Thr Asp Glu Cys Phe Phe Phe Glu Arg Leu
225                 230                 235                 240

Glu Ser Asn Asn Tyr Asn Thr Tyr Arg Ser Arg Lys Tyr Thr Ser Trp
                245                 250                 255

Tyr Val Ala Leu Lys Arg Thr Gly Gln Tyr Lys Leu Gly Ser Lys Thr
                260                 265                 270

Gly Pro Gly Gln Lys Ala Ile Leu Phe Leu Pro Met Ser Ala Lys Ser
        275                 280                 285

<210> SEQ ID NO 57
<211> LENGTH: 141
<212> TYPE: PRT
<213> ORGANISM: Homo sapiens
<220> FEATURE:
<221> NAME/KEY: misc_feature
<222> LOCATION: (1)..(141)
<223> OTHER INFORMATION: human PTHrP

<400> SEQUENCE: 57

Ala Val Ser Glu His Gln Leu Leu His Asp Lys Gly Lys Ser Ile Gln
1               5                   10                  15

Asp Leu Arg Arg Arg Phe Phe Leu His His Leu Ile Ala Glu Ile His
                20                  25                  30

Thr Ala Glu Ile Arg Ala Thr Ser Glu Val Ser Pro Asn Ser Lys Pro
            35                  40                  45

Ser Pro Asn Thr Lys Asn His Pro Val Arg Phe Gly Ser Asp Asp Glu
    50                  55                  60

Gly Arg Tyr Leu Thr Gln Glu Thr Asn Lys Val Glu Thr Tyr Lys Glu
65                  70                  75                  80

Gln Pro Leu Lys Thr Pro Gly Lys Lys Lys Gly Lys Pro Gly Lys
                85                  90                  95

Arg Lys Glu Gln Glu Lys Lys Lys Arg Arg Thr Arg Ser Ala Trp Leu
            100                 105                 110

Asp Ser Gly Val Thr Gly Ser Gly Leu Glu Gly Asp His Leu Ser Asp
        115                 120                 125

Thr Ser Thr Thr Ser Leu Glu Leu Asp Ser Arg Arg His
    130                 135                 140

<210> SEQ ID NO 58
<211> LENGTH: 35
<212> TYPE: PRT
<213> ORGANISM: Artificial Sequence
<220> FEATURE:
<223> OTHER INFORMATION: Synthetic: PTH(1-33) with Gly-Ser amino
      terminal extension

<400> SEQUENCE: 58

Gly Ser Ser Val Ser Glu Ile Gln Leu Met His Asn Leu Gly Lys His
1               5                   10                  15

Leu Asn Ser Met Glu Arg Val Glu Trp Leu Arg Lys Lys Leu Gln Asp
                20                  25                  30

Val His Asn
        35

<210> SEQ ID NO 59
```

```
<211> LENGTH: 30
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Xaa is 4-hydroxyproline
<220> FEATURE:
<221> NAME/KEY: misc_feature
<222> LOCATION: (5)..(5)
<223> OTHER INFORMATION: Xaa is 4-hydroxyproline
<220> FEATURE:
<221> NAME/KEY: misc_feature
<222> LOCATION: (8)..(8)
<223> OTHER INFORMATION: Xaa is 4-hydroxyproline
<220> FEATURE:
<221> NAME/KEY: misc_feature
<222> LOCATION: (11)..(11)
<223> OTHER INFORMATION: Xaa is 4-hydroxyproline
<220> FEATURE:
<221> NAME/KEY: misc_feature
<222> LOCATION: (14)..(14)
<223> OTHER INFORMATION: Xaa is 4-hydroxyproline
<220> FEATURE:
<221> NAME/KEY: misc_feature
<222> LOCATION: (17)..(17)
<223> OTHER INFORMATION: Xaa is 4-hydroxyproline
<220> FEATURE:
<221> NAME/KEY: misc_feature
<222> LOCATION: (20)..(20)
<223> OTHER INFORMATION: Xaa is 4-hydroxyproline
<220> FEATURE:
<221> NAME/KEY: misc_feature
<222> LOCATION: (23)..(23)
<223> OTHER INFORMATION: Xaa is 4-hydroxyproline
<220> FEATURE:
<221> NAME/KEY: misc_feature
<222> LOCATION: (26)..(26)
<223> OTHER INFORMATION: Xaa is 4-hydroxyproline
<220> FEATURE:
<221> NAME/KEY: misc_feature
<222> LOCATION: (29)..(29)
<223> OTHER INFORMATION: Xaa is 4-hydroxyproline

<400> SEQUENCE: 59

Pro Xaa Gly Pro Xaa Gly Pro Xaa Gly Pro Xaa Gly Pro Xaa Gly Pro
1               5                   10                  15

Xaa Gly Pro Xaa Gly Pro Xaa Gly Pro Xaa Gly Pro Xaa Gly
            20                  25                  30

<210> SEQ ID NO 60
<211> LENGTH: 40
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: Xaa is 4-hydroxyproline
<220> FEATURE:
<221> NAME/KEY: misc_feature
<222> LOCATION: (9)..(9)
<223> OTHER INFORMATION: Xaa is 4-hydroxyproline
<220> FEATURE:
<221> NAME/KEY: misc_feature
<222> LOCATION: (12)..(12)
<223> OTHER INFORMATION: Xaa is 4-hydroxyproline
<220> FEATURE:
<221> NAME/KEY: misc_feature
<222> LOCATION: (15)..(15)
<223> OTHER INFORMATION: Xaa is 4-hydroxyproline
<220> FEATURE:
<221> NAME/KEY: misc_feature
```

<222> LOCATION: (18)..(18)
<223> OTHER INFORMATION: Xaa is 4-hydroxyproline
<220> FEATURE:
<221> NAME/KEY: misc_feature
<222> LOCATION: (21)..(21)
<223> OTHER INFORMATION: Xaa is 4-hydroxyproline
<220> FEATURE:
<221> NAME/KEY: misc_feature
<222> LOCATION: (24)..(24)
<223> OTHER INFORMATION: Xaa is 4-hydroxyproline
<220> FEATURE:
<221> NAME/KEY: misc_feature
<222> LOCATION: (27)..(27)
<223> OTHER INFORMATION: Xaa is 4-hydroxyproline
<220> FEATURE:
<221> NAME/KEY: misc_feature
<222> LOCATION: (30)..(30)
<223> OTHER INFORMATION: Xaa is 4-hydroxyproline
<220> FEATURE:
<221> NAME/KEY: misc_feature
<222> LOCATION: (33)..(33)
<223> OTHER INFORMATION: Xaa is 4-hydroxyproline
<220> FEATURE:
<221> NAME/KEY: misc_feature
<222> LOCATION: (36)..(36)
<223> OTHER INFORMATION: Xaa is 4-hydroxyproline
<220> FEATURE:
<221> NAME/KEY: misc_feature
<222> LOCATION: (39)..(39)
<223> OTHER INFORMATION: Xaa is 4-hydroxyproline

<400> SEQUENCE: 60

Gly Pro Arg Gly Pro Xaa Gly Pro Xaa Gly Pro Xaa Gly Pro Xaa Gly
1               5                   10                  15

Pro Xaa Gly Pro Xaa Gly Pro Xaa Gly Pro Xaa Gly Pro Xaa Gly Pro
            20                  25                  30

Xaa Gly Pro Xaa Gly Pro Xaa Gly
        35                  40

<210> SEQ ID NO 61
<211> LENGTH: 95
<212> TYPE: PRT
<213> ORGANISM: Artificial Sequence
<220> FEATURE:
<223> OTHER INFORMATION: Synthetic

<400> SEQUENCE: 61

Pro Glu Ile Lys Asp Leu Ser Glu Asn Lys Leu Pro Val Ile Tyr Met
1               5                   10                  15

His Val Pro Lys Ser Gly Ala Leu Asn Gln Lys Val Val Phe Tyr Gly
            20                  25                  30

Lys Gly Thr Tyr Asp Pro Asp Gly Ser Ile Ala Gly Tyr Gln Trp Asp
        35                  40                  45

Phe Gly Asp Gly Ser Asp Phe Ser Ser Glu Gln Asn Pro Ser His Val
    50                  55                  60

Tyr Thr Lys Lys Gly Glu Tyr Thr Val Thr Leu Arg Val Met Asp Ser
65                  70                  75                  80

Ser Gly Gln Met Ser Glu Lys Thr Met Lys Ile Lys Ile Thr Asp
                85                  90                  95

<210> SEQ ID NO 62
<211> LENGTH: 84
<212> TYPE: PRT
<213> ORGANISM: Homo sapiens
<220> FEATURE:
<221> NAME/KEY: misc_feature
<222> LOCATION: (1)..(84)
<223> OTHER INFORMATION: human parathyroid hormone

```
<400> SEQUENCE: 62

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp Ala Gly Ser
        35                  40                  45

Gln Arg Pro Arg Lys Lys Glu Asp Asn Val Leu Val Glu Ser His Glu
    50                  55                  60

Lys Ser Leu Gly Glu Ala Asp Lys Ala Asp Val Asn Val Leu Thr Lys
65                  70                  75                  80

Ala Lys Ser Gln
```